United States Patent
Wisbey et al.

(10) Patent No.: US 10,129,628 B2
(45) Date of Patent: Nov. 13, 2018

(54) SYSTEMS, METHODS AND DEVICES FOR PROVIDING AN EXERTION RECOMMENDATION BASED ON PERFORMANCE CAPACITY

(71) Applicant: LOGITECH EUROPE S.A., Lausanne (CH)

(72) Inventors: Ben Wisbey, Canberra (AU); Judd Armstrong, Parrearra (AU); Hagen Diesterbeck, Coromandel (NZ); David Shepherd, Canberra (AU)

(73) Assignee: LOGITECH EUROPE, S.A., Lausanne (CH)

( * ) Notice: Subject to any disclaimer, the term of this patent is extended or adjusted under 35 U.S.C. 154(b) by 204 days.

(21) Appl. No.: 15/012,776

(22) Filed: Feb. 1, 2016

(65) Prior Publication Data
US 2017/0216672 A1    Aug. 3, 2017

(51) Int. Cl.
*A63F 13/00* (2014.01)
*H04R 1/10* (2006.01)
(Continued)

(52) U.S. Cl.
CPC .......... *H04R 1/1041* (2013.01); *A61B 5/1118* (2013.01); *A61B 5/681* (2013.01);
(Continued)

(58) Field of Classification Search
CPC .............. A61B 5/00; A61B 5/04; G09B 19/00
See application file for complete search history.

(56) References Cited

U.S. PATENT DOCUMENTS 2,189,096 A    2/1940  Alonge
3,543,724 A    12/1970 Kirkpatrick et al.
(Continued)

OTHER PUBLICATIONS

"watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).
(Continued)

*Primary Examiner* — James S McClellan
(74) *Attorney, Agent, or Firm* — Patterson & Sheridan, LLP

(57) ABSTRACT

Systems, methods, and devices are provided for determining an exertion recommendation for an anticipated exercise session. One such system includes a wearable device comprising a biosensor that monitors biometrics (e.g. heart rate); a motion sensor that monitors activity; a processor operatively coupled to the biosensor, the processor configured to process electronic signals periodically generated by the biosensor and the motion sensor; and a non-transitory computer-readable medium operatively coupled to the processor and storing instructions that, when executed, cause the processor to execute specific functions. In particular, the instructions are executed to cause the processor to generate biometric data from the biometrics (e.g. heart rate information in particular). Further, the instructions are executed to generate an exertion recommendation based on an exertion model created from and representing a relationship between prior exertion measures and prior response profile measures.

23 Claims, 27 Drawing Sheets

(51) Int. Cl.
  *G09B 19/00*   (2006.01)
  *A61B 5/11*    (2006.01)
  *A61B 5/00*    (2006.01)

(52) U.S. Cl.
  CPC .......... *A61B 5/6803* (2013.01); *A61B 5/6815* (2013.01); *G09B 19/003* (2013.01); *H04R 1/1016* (2013.01); *H04R 2420/09* (2013.01); *H04R 2430/01* (2013.01)

(56) References Cited

U.S. PATENT DOCUMENTS

| | | |
|---|---|---|
| 3,978,849 A | 9/1976 | Geneen |
| 4,129,124 A | 12/1978 | Thalmann |
| 4,224,984 A | 9/1980 | Cramer et al. |
| 4,307,727 A | 12/1981 | Haynes |
| 4,331,154 A | 5/1982 | Broadwater et al. |
| 4,407,295 A | 10/1983 | Steuer et al. |
| 4,409,983 A | 10/1983 | Albert |
| 4,491,970 A | 1/1985 | Lawhite et al. |
| 5,301,154 A | 4/1994 | Suga |
| 5,392,261 A | 2/1995 | Hsu |
| 5,406,952 A | 4/1995 | Barnes et al. |
| 5,524,637 A | 6/1996 | Erickson |
| 5,734,625 A | 3/1998 | Kondo |
| 5,755,623 A | 5/1998 | Mizenko |
| 5,899,370 A | 5/1999 | Bould |
| 6,151,968 A | 11/2000 | Chou |
| 6,361,503 B1 | 3/2002 | Starobin et al. |
| 6,736,759 B1 | 5/2004 | Stubbs et al. |
| 7,192,401 B2 | 3/2007 | Saalasti et al. |
| 7,717,827 B2 | 5/2010 | Kurunmaki et al. |
| 7,914,425 B2 | 3/2011 | Hanoun |
| 8,992,385 B2 | 3/2015 | Lemos |
| 2002/0151811 A1 | 10/2002 | Starobin et al. |
| 2002/0188210 A1 | 12/2002 | Aizawa |
| 2003/0065269 A1 | 4/2003 | Vetter et al. |
| 2005/0056655 A1 | 3/2005 | Gary |
| 2005/0116811 A1 | 6/2005 | Eros et al. |
| 2005/0256416 A1 | 11/2005 | Chen |
| 2006/0183980 A1 | 8/2006 | Yang |
| 2007/0118043 A1* | 5/2007 | Oliver .................. A61B 5/0245 600/519 |
| 2008/0132383 A1 | 6/2008 | Einav et al. |
| 2008/0228089 A1 | 9/2008 | Cho et al. |
| 2009/0047645 A1* | 2/2009 | Dibenedetto ....... G06F 19/3418 434/258 |
| 2009/0312656 A1 | 12/2009 | Lau et al. |
| 2010/0197463 A1 | 8/2010 | Haughay, Jr. et al. |
| 2011/0021319 A1* | 1/2011 | Nissila .................. A61B 5/222 482/8 |
| 2011/0092790 A1 | 4/2011 | Wilder-Smith et al. |
| 2011/0260870 A1 | 10/2011 | Bailey |
| 2012/0010478 A1* | 1/2012 | Kinnunen .......... A61B 5/02405 600/301 |
| 2012/0022341 A1 | 1/2012 | Zdeblick |
| 2012/0168471 A1 | 7/2012 | Wilson |
| 2012/0253485 A1 | 10/2012 | Weast et al. |
| 2013/0053990 A1* | 2/2013 | Ackland ................ G06Q 30/02 700/91 |
| 2013/0064049 A1 | 3/2013 | Pileri et al. |
| 2013/0237778 A1 | 9/2013 | Rouquette |
| 2014/0032234 A1 | 1/2014 | Anderson |
| 2014/0073486 A1 | 3/2014 | Ahmed et al. |
| 2014/0107493 A1 | 4/2014 | Yuen et al. |
| 2014/0228175 A1 | 8/2014 | Lemos et al. |

OTHER PUBLICATIONS

"Elite Clock Military Style LED Watch" by ledwatchsuk. YouTube [dated May 31, 2011][online][retrieved on Aug. 14, 2015].

* cited by examiner

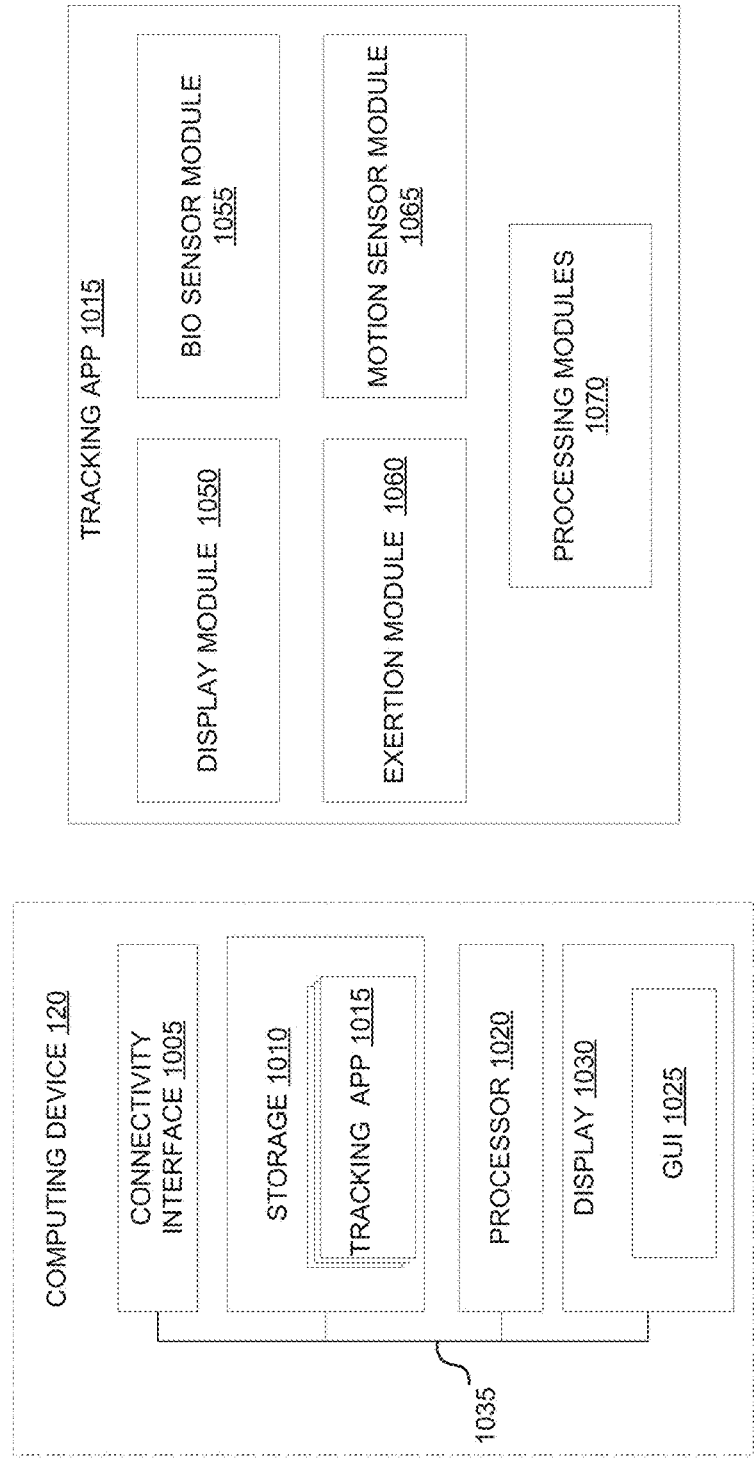

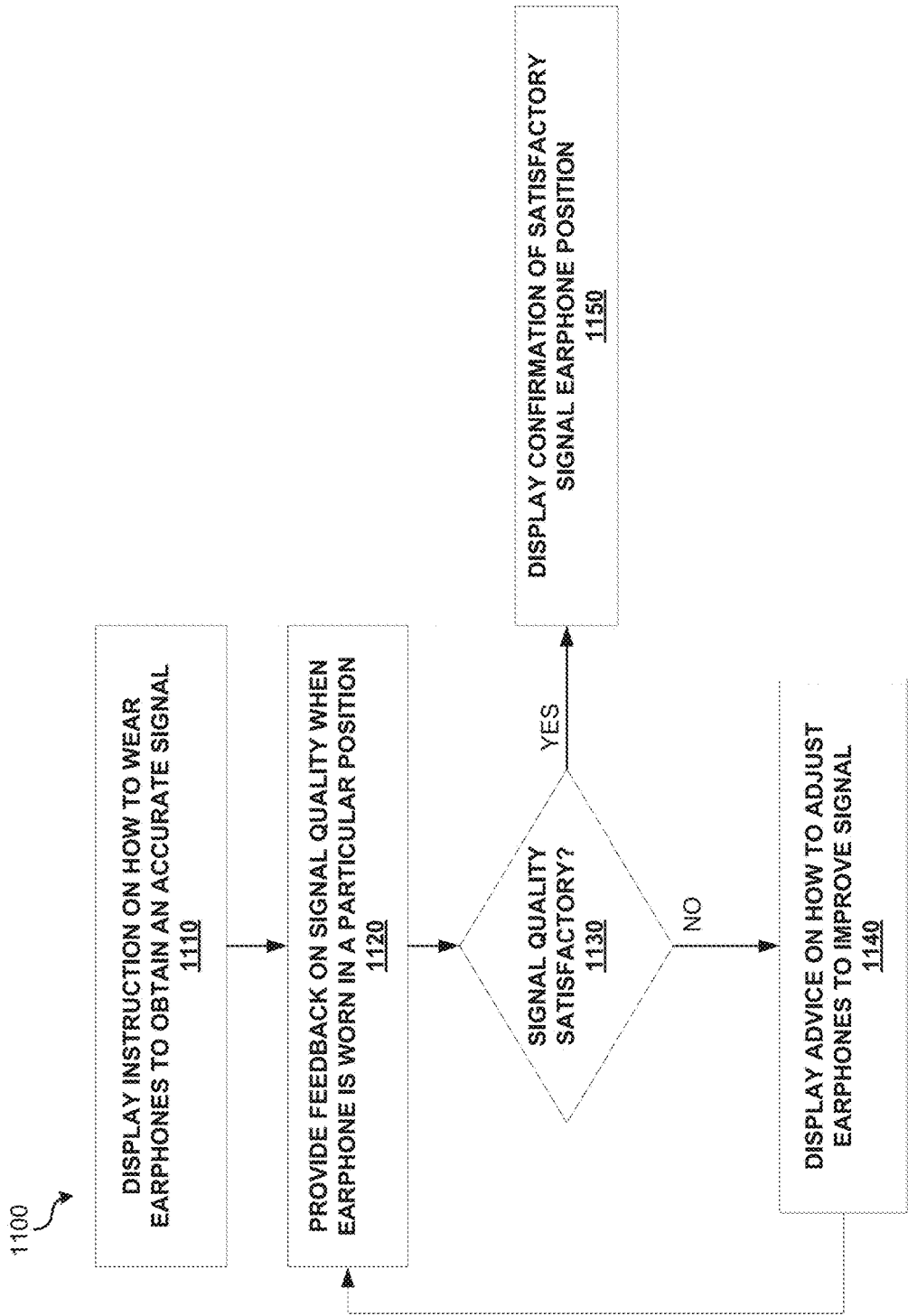

SYSTEMS, METHODS AND DEVICES FOR PROVIDING AN EXERTION RECOMMENDATION BASED ON PERFORMANCE CAPACITY

TECHNICAL FIELD

The present disclosure relates generally to fitness and activity monitoring devices, and more particularly to systems and methods for providing an exertion recommendation based on performance capacity using such devices.

BACKGROUND

Previous generation fitness tracking devices generally only enabled a user to identify their heart rate during an exercise session or other activity. More modern fitness tracking devices now add functionality that monitor and track a user's fitness level, for example, by counting the user's steps, estimating the total calories burned, miles run, etc., and/or by estimating the user's heart rate variability and other biometric data. Nevertheless, currently available fitness monitoring devices do not provide a user with a precise measure of exertion during and throughout a given exercise session, and further do not provide a precise exertion recommendation for a future exercise session based on prior measures. In particular, currently available devices do not provide a personalized and precise exertion recommendation for an upcoming exercise session, as a measure of the user's prior exertion measures, response profile (i.e. performance capacity) measures, and the like.

Because each person has unique physical characteristics and capabilities, the effort required to perform a given activity or task—and the intensity with which the task may be performed—may differ between individuals. For example, a person with short legs may need to exert more effort to run a mile in six minutes than a person with much longer legs, all else being equal. Moreover, each person has unique recovery characteristics that may also change with time—whether in the short term or long term. For example (demonstrating long term changes), in running a marathon a middle-aged person may find that with each mile they experience more fatigue (i.e. slower recovery) than they did when they ran the same marathon as a teenager. In another example (demonstrating short term changes), a weight-lifter wishing to perform 20 reps on a bench press will need to exert more effort to lift the barbell the twentieth time than she did for the nineteenth time; or in other words recovery will gradually slow throughout the set of 20 reps (and therefore greater effort will be required with each consecutive rep) because of the effort already exerted in each previous rep. In other words, the effort required to perform a given activity will differ from one moment to the next for particular individuals—even within the same exercise session—depending on what they have been doing up to that point. Finally, the effort required to perform a given activity may differ depending on how quickly the activity must be performed. For example, a person must exert more energy (i.e. greater intensity) to run a mile in six minutes than to run a mile in ten minutes, and the impact of each scenario will differ accordingly.

In view of the foregoing incongruities, quantifying and providing a precise and personalized measure of exertion, as well as a precise and personalized measure of the user's response profile, can be of great value to athletes seeking to modify, track, or gauge the effectiveness of their training regimen, project the impact of a particular activity on their physical condition at a given moment after a previously performed activity, or to make any other such exertion based assessment. Furthermore, conventional devices do not provide a precise and personalized exertion recommendation to user's for a future exercise session (or other activity or time interval) based on the user's prior exertion measures and/or prior response profile measures. Because currently available devices do not provide such a precise such measures, it can be difficult for a user to meaningfully assess the impact that a particular activity has had, is currently having, or will have on their body (e.g. energy level, capacity, stamina, etc.); and be even more difficult to intelligently evaluate how to approach an anticipated exercise session to achieve their desired goals.

BRIEF SUMMARY OF THE DISCLOSURE

In view of the above drawbacks, there exists a long-felt need for systems, methods, and devices for detecting, computing and providing user's with a precise and personalized measure of exertion based on an accumulated measure of their exercise intensity over the course of a particular exercise session, a given activity, or a predetermined timeframe. Further, there exists a long felt need for systems, methods, and devices for intelligently assessing a user's response profile (i.e. performance capacity) based on biometric and activity data as described herein. Finally, there exists a ling-felt need for systems, methods, and devices for determining and providing an exertion recommendation for anticipated/imminent/future exercise sessions using prior measures of exertion and/or prior response profile measures as described above.

Such systems, methods and devices are the subject of this disclosure, and as one of ordinary skill in the art will appreciate, will in operation enable a user to meaningfully and intelligently assess their exertion levels during and after an exercise session; assess their response profile before, during, and after an exercise session; and receive/evaluate a recommended exertion for a future exercise session based on one or more prior exertion measures and/or response profile measures.

BRIEF DESCRIPTION OF THE DRAWINGS

The present disclosure, in accordance with one or more various embodiments, is described in further detail with reference to the following Figures. The Figures are provided for purposes of illustration only and merely depict typical or example embodiments of the disclosure.

FIG. 10A is a block diagram of an example computing device that may be used in accordance with various embodiments of the present disclosure.

FIG. 10B illustrates an example fitness tracking application and modules in accordance with various embodiments of the present disclosure.

FIG. 11 is an example operational flow diagram illustrating various operations that may be performed to prompt a user to adjust the placement of earphones in the user's ear in accordance with various embodiments of the present disclosure.

Figure 1:
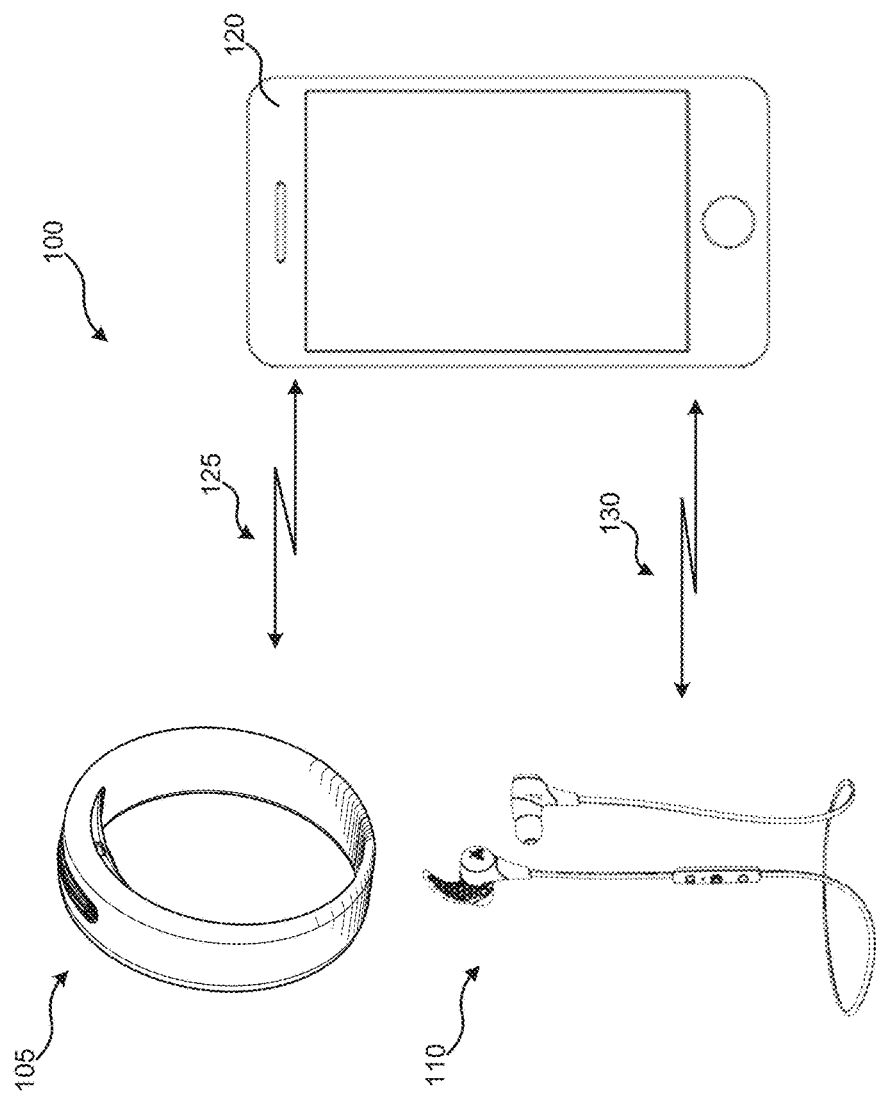
FIG. 1 illustrates an example communications environment in which embodiments of the present disclosure may be implemented.

It should be noted that the figures are provided for purposes of illustration only, and merely depict typical or example embodiments of the present disclosure. The figures are not intended to be exhaustive or to limit the disclosure to the precise form disclosed. Indeed, other features and aspects of the disclosed technology will become apparent to one of ordinary skill in the art upon reviewing the following detailed description in connection with the accompanying drawings. It should also be understood that the disclosure is not intended to limit the scope of any embodiments described herein, which are limited solely by the claims attached hereto.

DETAILED DESCRIPTION

Embodiments of the present disclosure are directed toward systems, methods and devices for providing an exertion recommendation for an anticipated exercise session, the exertion recommendation being based, in whole or in part, on one or more prior measures of exertion and/or response profile during a previous exercise session. The determination of the user's exertion is, in various embodiments, based on biometric data gathered from sensors that may be worn by the user. Similarly, the determination of the user's performance capacity (i.e. response profile) is, in various embodiments, based on biometric data and/or activity data gathered from sensors that may be worn by the user. The details of some example embodiments of the systems, methods, and devices of the present disclosure are set forth in more detail in the description below. Other features, objects, and advantages of the disclosure will be apparent to one of skill in the art upon examination of the present description, figures, examples, and claims. It is intended that all such systems, methods, features, objects and advantages be included within the scope of the present disclosure, and be protected by one or more of the accompanying claims.

In particular embodiments, systems and methods for providing such an exertion recommendation are implemented using activity monitoring devices embodied in one or more of an earphone, a wristband, an electronic capsule, or other computing device or apparatus as described in more detail below with reference to FIGS. 1-16. It should be noted that the activity monitoring devices depicted in these Figures are provided for purposes of illustration only and merely depict typical or example implementations and embodiments of the technology disclosed herein. Prior to introducing details of the exertion recommendation determination, a discussion of the exemplary activity monitoring devices with which this technology may be implemented is appropriate. Although the discussion of each figure should be considered in the context of the entire disclosure, simply for clarity it is noted that FIGS. 1-12 directed more particularly toward a discussion of the structure, architecture, and component features of the activity monitoring devices with which the presently disclosed technology may be implemented, and FIGS. 13A-15B are directed more particularly toward the details surrounding the various operations that may be performed as part of the systems, methods, and devices of the present disclosure to determine and provide exertion as a measure of accumulated exercise intensity.

FIG. 1 depicts an example communications environment 100, which may be used in connection with implementing embodiments of the disclosed systems, methods, and devices. As shown, communications environment 100 may include wristband 105 and/or earphones 110. As will be described in detail herein, wristband 105 and earphones 110 may be used to monitor activity and/or measure biometrics. Additionally, wristband 105 and earphones 110 may be operatively coupled to computing device 120, which in the illustrated example is a mobile device. This coupling may be implemented in some examples using links 125 and 130, which in various instances may be a wired or wireless connection.

Computing device 120 may collect additional information from the user—such as biometrics and activity information—which may be used to supplement or be used in place of information received from wristband 105 or earphones 110. Computing device 120 may include a variety of electronic computing devices, such as, for example, a smartphone, tablet, laptop, and the like. In such cases, computing device 120 may be configured to receive biometrics and/or activity information from one or more of wristband 105 and earphones 110 over one or more of links 125 and 130. Further, in some embodiments, computing device 120 may include a graphical user interface (GUI) for displaying and interacting with one or more of wristband 105 and/or earphones 110, including by interacting with data collected by and received from wristband 105 and/or earphones 110, and by controlling the operation of wristband 105 and/or earphones 110.

Here it will be noted that the GUI of computing device 120 may additionally perform functions such as accepting user input and displaying processed biometric and/or activity data to the user. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, links 125 and 130 may be based on one or more wireless communication protocols such as Bluetooth, ZigBee, 802.11 protocols, Infrared (IR), Radio Frequency (RF), 2G, 3G, 4G, etc.

Figure 2:
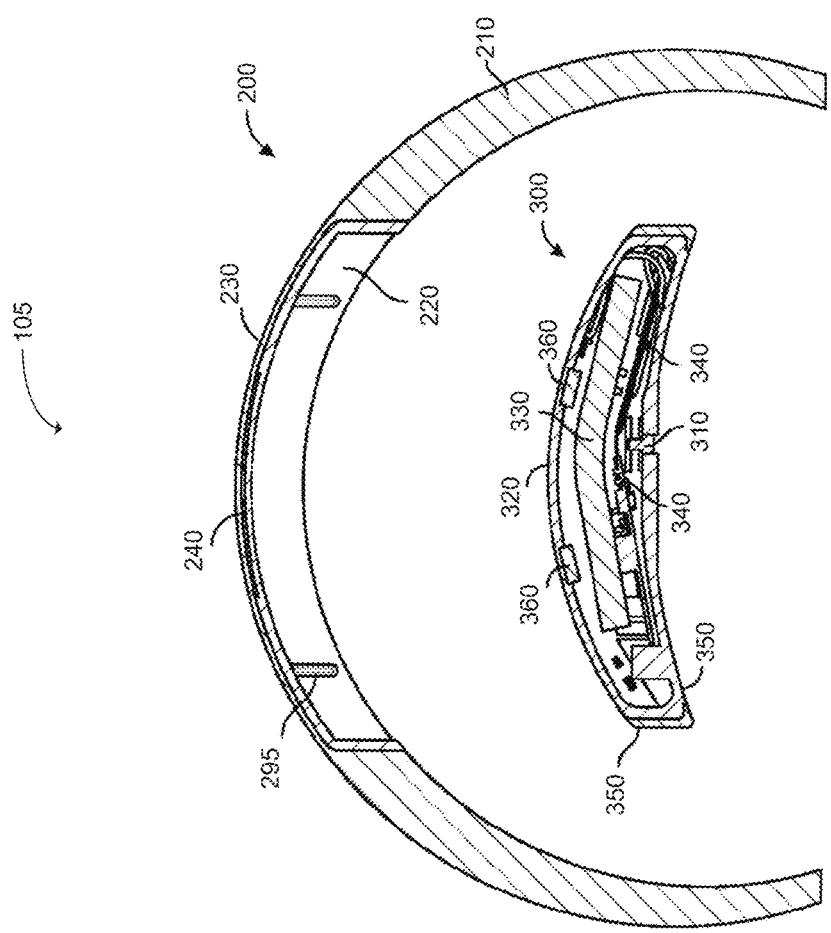
FIG. 2 illustrates a cross-sectional view of an example wristband—depicted with the exemplary electronic capsule decoupled from the exemplary band—in accordance with various embodiments of the present disclosure.
Figure 3:
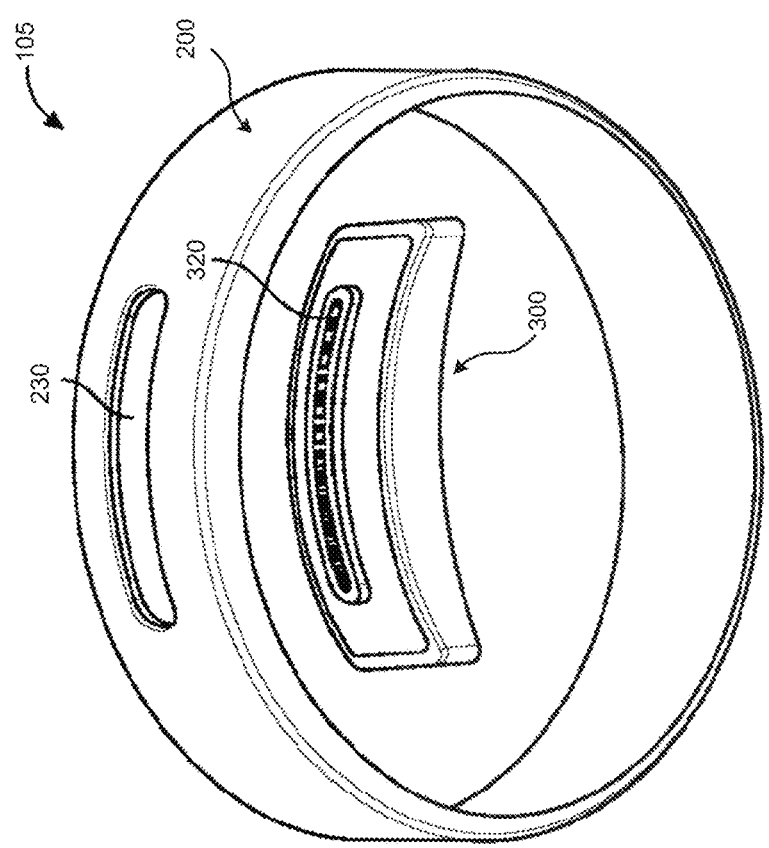
FIG. 3 illustrates a perspective view of the example wristband depicted in FIG. 2—including the electronic capsule and band—in accordance with various embodiments of the present disclosure.

FIG. 2 depicts an exploded cross-sectional view of example embodiments of wristband 105. FIG. 3 illustrates a perspective view of wristband 105. Aspects of FIGS. 2 and 3 will be described together. As depicted, wristband 105 includes band portion 200 and electronic capsule 300. Electronic capsule 300 includes various electronic components, as depicted in a simplified manner in FIG. 2. Further as depicted, electronic capsule 300 may be a removable/detachable component that may be coupled to and removable/detachable from band portion 200. This may be accomplished in a variety of ways, e.g., magnetic attraction forces, snap-fit/friction, etc. In other cases, electronic capsule 300 may be integrally formed with band portion 200.

Electronic capsule 300 may include various components, such as battery 330, logic circuits 340, casing 350, and one or more of a wrist biosensor 310, finger biosensor 320, and/or a motion sensor (e.g., accelerometer, gyroscope, magnetometer, or other inertial measurement unit). Typically, at least one of wrist biosensor 310 and finger biosensor 320 is a heart rate sensor configured to detect the heart rate of a wearer of wristband 105. In some embodiments, finger biosensor 320 protrudes outwardly from a first side (i.e., the top) of casing 350 of electronic capsule 300, and wrist biosensor protrudes outwardly from a second side (i.e., the bottom) of casing 350. As depicted, aperture 230 of band portion 200 substantially matches the dimensional profile of finger biosensor 320, such that finger biosensor 320 may be exposed and accessible to the touch of a user's finger through aperture 230 when wristband 105 is worn by the user. In various embodiments, battery 330, logic circuits 340, and an optional motion sensor are enclosed inside of casing 350. Battery 330 is electronically coupled and supplies power to logic circuits 340. By way of example, logic circuits 340 may by implemented using printed circuit boards (PCBs). Although wristband 105 is shown in FIGS. 2 and 3 as including both wrist biosensor 310 and finger biosensor 320, some embodiments include only one or the other.

Casing 350 may be made of various materials known in the art, including, for example, molded plastic, silicone, rubber, or another moldable material. Additionally, casing 350 may be sealed using an ultrasonic welding process to be substantially water tight, thus protecting electronic capsule 300 from the elements. Further, wristband 105 may be configured to encircle (either partially as in FIG. 2, or entirely as in FIG. 3) a wrist or other limb (e.g., ankle, etc.) of a human, animal, or other object. In one embodiment, wristband 105 is adjustable in size/fit. In some embodiments, a cavity 220 is notched on the radially inward facing side of band 200 and shaped to substantially the same dimensions as the profile of electronic capsule 300. In addition, aperture 230 may be located in the material 210 of band 200 within cavity 220. Aperture 230 may be shaped to substantially the same dimensions as the profile of the finger biosensor 320. As shown, cavity 220 and aperture 230 are in combination designed to detachably couple to electronic capsule 300 such that, when electronic capsule 300 is positioned inside cavity 220, finger biosensor 320 protrudes at least partially into—and sometimes protruding through the top of—aperture 230 such that at least a portion of the electronic capsule 300 may be exposed to the touch of a user's finger. Electronic capsule 300 may further include one or more magnets 360 configured to secure electronic capsule 300 in cavity 220. Magnets 360 may be concealed in casing 350. Alternatively, cavity 220 may be configured to conceal magnets 360 when electronic capsule 300 detachably couples in cavity 220.

Wristband 105 may further include a ferromagnetic metal strip 240 concealed in band portion 200 within cavity 220. In such a case, when electronic capsule 300 is positioned within cavity 220, magnets 360 are attracted to ferromagnetic strip 240 and pull electronic capsule 300 radially outward with respect to band portion 200. The force provided by magnets 360 may detachably secure electronic capsule 300 inside cavity 220. In alternative embodiments, electronic capsule 300 may be positioned inside cavity 220 and be affixed therein using a form-fit, press-fit, snap-fit, friction-fit, VELCRO, or other temporary adhesion or attachment technology.

In some embodiments, logic circuits 340 include an a motion sensor that includes an inertial measurement unit (e.g., one or more of a gyroscope, accelerometer, and magnetometer, etc.), a wireless transmitter, and additional circuitry. Logic circuits 340 may be configured to process electronic signals from biosensors (e.g., finger biosensor 320 and wrist biosensor 310) and/or motion sensors, convert/store the electronic signals as data, and output the data via the transmitter (e.g., using wireless protocols described herein). In other scenarios, this data may be output using a wired connection (e.g., USB, fiber optic, HDMI, or the like).

Referring again to electronic capsule 300, in some embodiments the electronic signals processed by logic circuits 340 include an activation time signal and a recovery time signal. In these embodiments, logic circuits 340 may process the electronic signals to calculate an activation recovery interval equal to the difference between the activation time signal and the recovery time signal. The electronic signals may include heart rate information collected by and received from one or more of the wrist biosensor 310 and finger biosensor 320. Further still the electronic signals may include electro-cardio signals from a user's heart. In these embodiments, logic circuits 340 may process the electro-cardio signals to calculate and store an RR-interval and determine a heart rate. The RR-interval may be the delta in time between two R-waves, where the R-waves are the electro-cardio signals generated by a ventricle contraction in the heart. The RR-interval may further be used to calculate and store a heart rate variability (HRV) value that indicates the variation over time of the time delta between consecutive heartbeats. In some embodiments, logic circuits 340 may convey the electronic signals to, e.g., computing device 120, by a transmitter, such that computing device 120 may perform various calculations (e.g., of HRV, HR, Exercise Intensity, Exertion Value, Exertion Load, Exertion Index etc.).

In some instances, finger biosensor 320 and wrist biosensor 310 may be replaced or supplemented by a single biosensor configured to detect and measure biometric information (e.g. HR, HRV, etc.). In some embodiments, the single biosensor may be an optical biosensor such as a pulse oximeter configured to detect blood oxygen saturation levels. The pulse oximeter may output electronic signal(s) to logic circuits 340 indicating a detected cardiac cycle phase and/or heart rate, and logic circuits 340 may use such information (e.g. the cardiac cycle phase and/or heart rate data) to further calculate an HRV value, or logic circuits 340 may convey the information to, e.g., computing device 120, by a transmitter such that computing device 120 may perform various calculations (e.g., of HRV, HR, etc.). Logic circuits 340, in some embodiments, may further detect and store metrics based on motion detection, such as the amount of physical activity, sleep, or rest, over a period of time, or the amount of time with or without physical activity over a period of time. In other embodiments, logic circuits 340 may detect and store metrics based on heart rate detection, such as the user's exercise intensity and/or exertion over a period of time or during a particular activity (e.g. an exercise session, a 24 hour period, etc.). Providing and determining exercise intensity and exertion will be discussed in further detail in connection with FIGS. 13A-13F.

Figure 4:
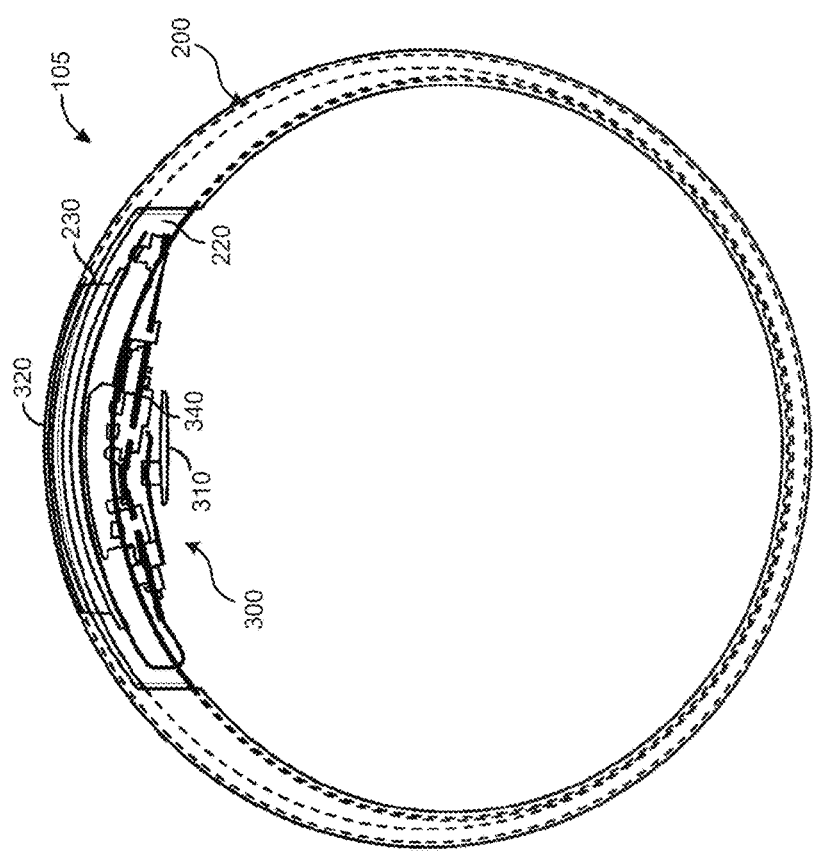
FIG. 4 illustrates a cross-sectional view of another example wristband in accordance with various embodiments of the present disclosure—here depicted with the exemplary electronic capsule in a coupled orientation with the exemplary band.

FIG. 4 illustrates a cross-sectional view of one embodiment of wristband 105 when assembled with electronic capsule 300. In this embodiment, electronic capsule 300 is positioned inside cavity 220 such that finger biosensor 320 is partially disposed in and exposed through aperture 230. Wrist biosensor 310 protrudes from the radially inward facing side band portion 200. In this configuration, wrist biosensor 310 may contact the skin on the wearer's limb (e.g. wrist, ankle, etc.) when the wristband 105 is worn.

Figure 5:
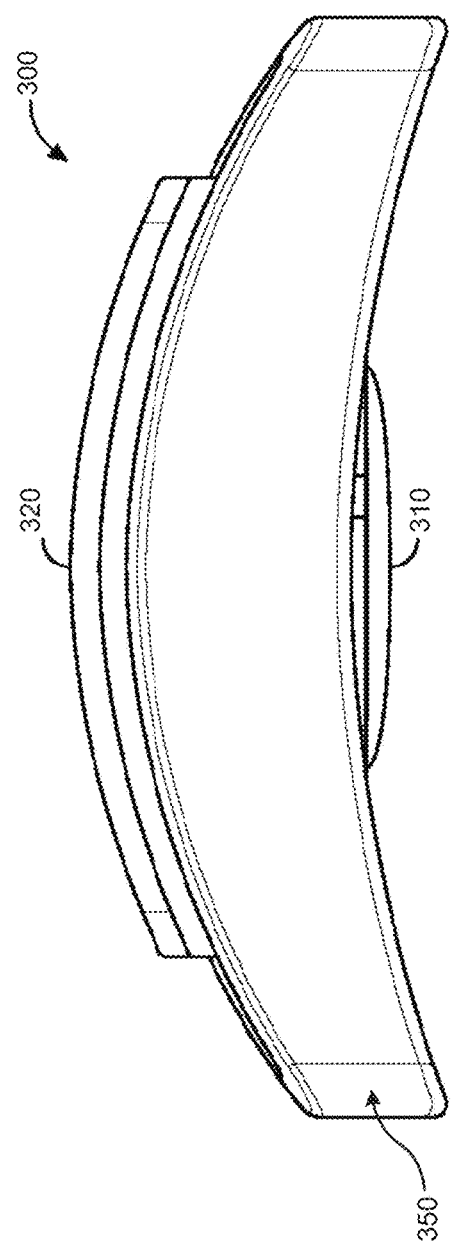
FIG. 5 illustrates a side view of an example electronic capsule that may be used in accordance with various embodiments of the present disclosure.

FIG. 5 illustrates a side view of electronic capsule 300. As depicted, finger biosensor 320 may protrude from a first side of electronic capsule 300, and wrist biosensor 310 may protrude from a second side of electronic capsule 300. Casing 350 encloses components of electronic capsule 300. Casing 350 may include moldable plastic. Alternatively, casing 350 may include metal, rubber, composite material, or another, moldable material. In one embodiment, casing 350 is ultrasonically welded together to make the casing water tight and/or resistant. In alternative embodiments, other methods may be used to make the casing water tight/resistant.

Figure 6:
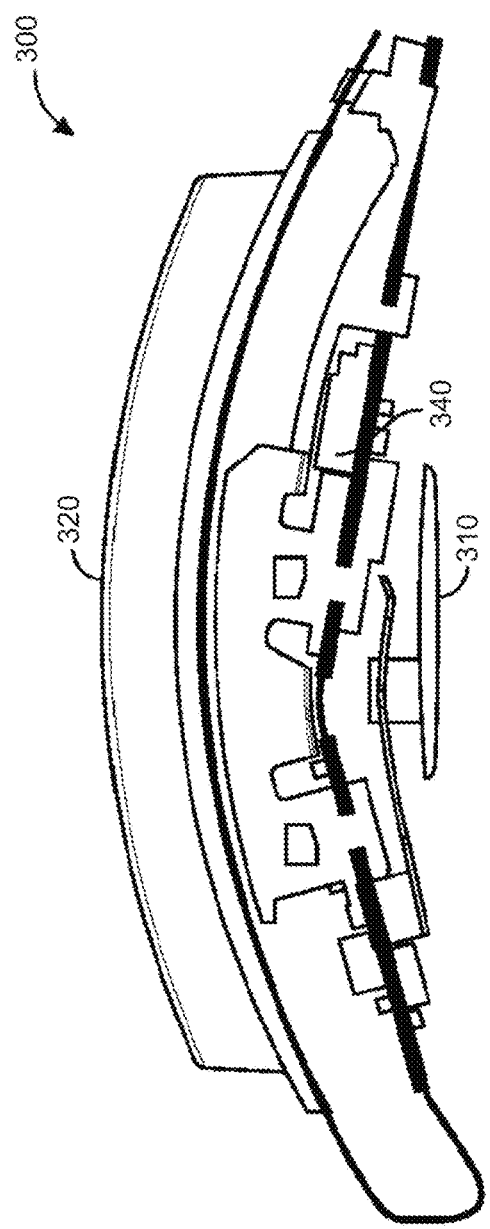
FIG. 6 illustrates a cross-sectional view of an exemplary electronic capsule that may be used in accordance with various embodiments of the present disclosure.

FIG. 6 illustrates another cross-sectional view of electronic capsule 300. In the illustrated embodiment, finger biosensor 320 protrudes from a first side of electronic capsule 300, and wrist biosensor 310 protrudes from a second side of electronic capsule 300. Both finger biosensor 320 and wrist biosensor 310 are electronically coupled to logic circuits 340.

Figure 7:
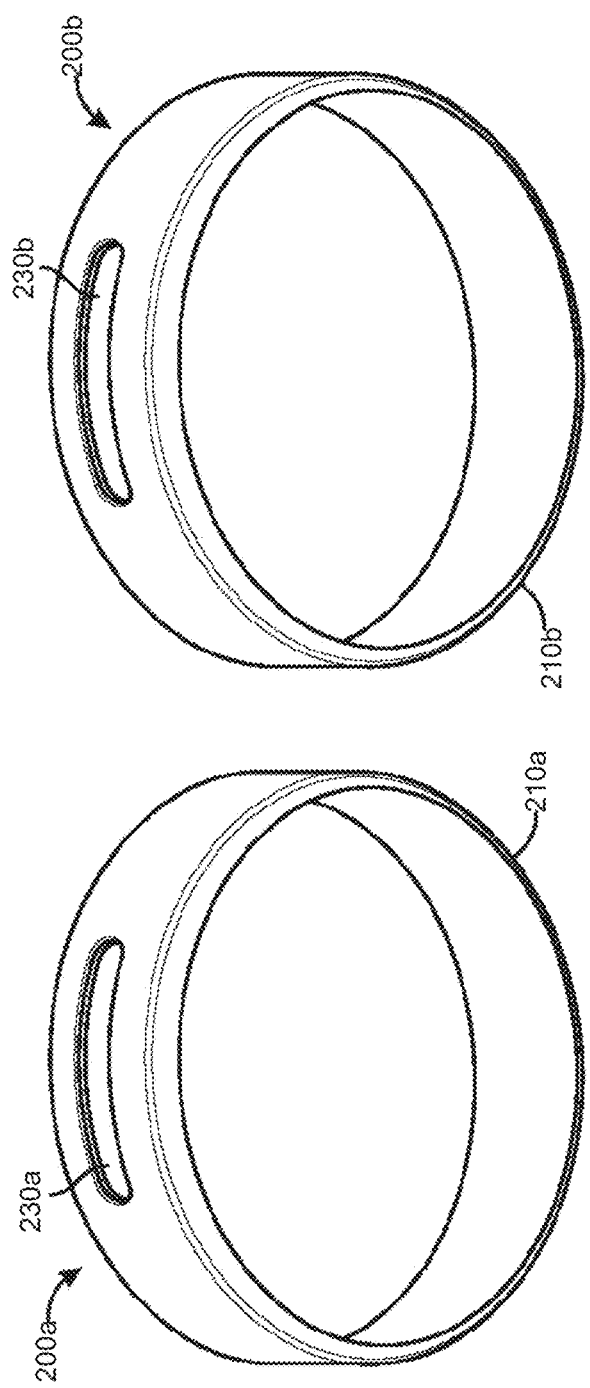
FIG. 7 illustrates a perspective view of example bands according to embodiments of the present disclosure.

FIG. 7 is a perspective view of two possible variants of band 200 that may be used in accordance with embodiments disclosed herein. Each band 200 in this embodiment includes flexible material, an aperture 230 is disposed on/in each band 200. Electronic capsule's 300 depicted in, e.g. FIGS. 2-5, may be sized so as to be easily removed from one band 200a and placed in another band 200b. Bands 200a, 200b may also be constructed with different dimensions, including different diameters, widths, and thicknesses, in order to accommodate different sized/shaped limbs and appendages, as well as wearer preferences. In one embodiment, bands 200a, 200b may be adjustable to accommodate different sizes/shapes of limbs. Further, bands 200a, 200b may be made in different colors, and different flexible materials, such as silicone, plastic, metal chain links, composite material, leather, synthetic leather, fabric, or other flexible materials.

In some embodiments an electronic capsule (e.g. electronic capsule 300 of FIG. 5) may be detachably coupled to various other locations besides band 200. For example, an electronic capsule may be attached to a user's shoe and/or sock, coupled to sports equipment (e.g. the handle of a racket or bicycle) such that one of biosensors 310 or 320 may contact parts of a user's body. In such embodiments, band 200 may be eliminated altogether, and electronic capsule 300 may be used in connection with computing device 120 to implement the technology provided in this disclosure (compute and provide exertion as a measure of accumulated exercise intensity).

Electronic capsules 300 used in accordance with some embodiments of the presently disclosed technology may include one or more optical sensors such as a heart rate sensor or oximeter. In such embodiments, for example, the oximeter may sense heart rate and/or HRV by detecting blood oxygenation level changes as changes in coloration at the surface of a user's skin. The optical sensor may be positioned to face radially inward towards a limb when wristband 105 is worn. Alternatively, the optical sensor may be separate from electronic capsule 300, but still detachably coupled to band 200 and/or electronically coupled to circuit boards that may be enclosed in electronic capsule 300 (e.g., wirelessly coupled or otherwise).

Referring again to FIG. 1, in various embodiments, computing device 120 may receive, process and/or display data collected, determined, and/or processed by logic circuits 340, thereby allowing the user to interact with wristband 105 and/or otherwise monitor the user's activity and/or biometrics, as will be further described herein. Additionally, computing device 120 may itself be used to collect additional activity monitoring and/or biometric data using sensors (e.g. biosensors, motion sensors, etc.) included in computing device 120. Further still, computing device 120 may be bi-directionally communicatively coupled (e.g., by links 125 and 130) with wristband 105 such that computing device 120 may be used to configure the functionality of logic circuits 340. In such cases, logic circuits 340 include a receiver as well as a transmitter, and/or a transceiver.

In other embodiments, computing device 120 may connect to the Internet and receive biometric and/or activity data gathered by wristband 105 (via electronic components in electronic capsule 300) over a web browser. For example, the wristband 105 may gather/process biometric, activity, and other data, and transmit that data to a remote file server, such that computing device 120 may then access the data from the remote file server without directly linking to wristband 105. In yet further embodiments, computing device 120 may be mechanically coupled, electrically coupled, or both mechanically and electrically coupled to wristband 105, such that communication can take place over a wired or near-field connection.

Figure 8A:
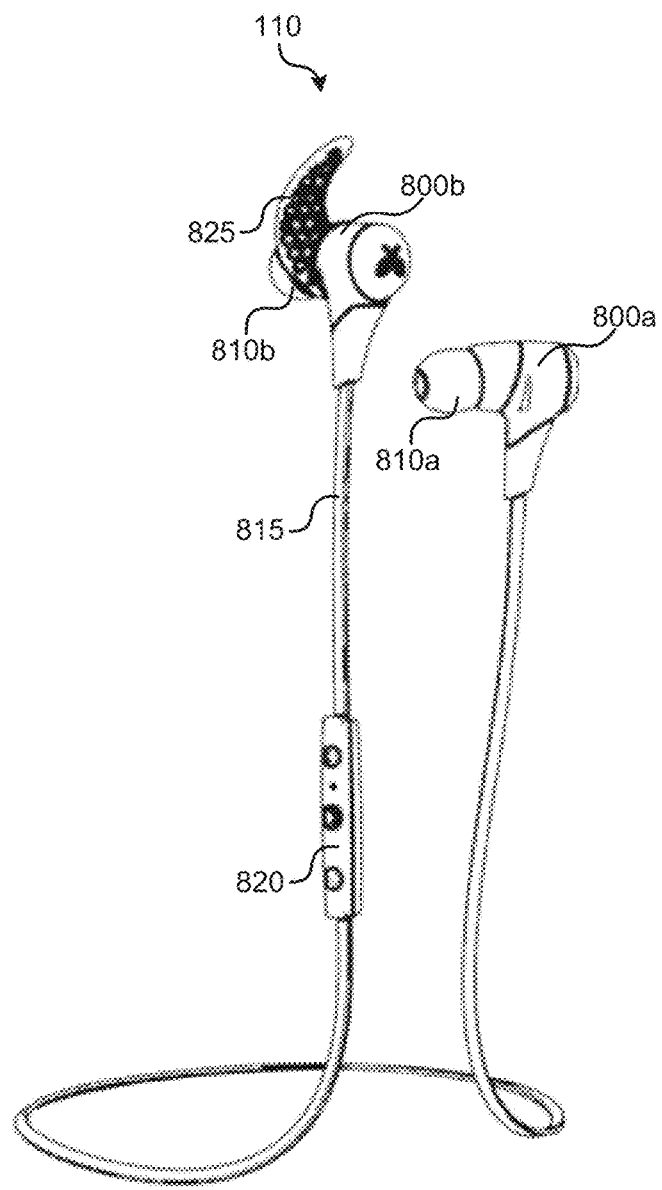
FIG. 8A illustrates a perspective view of example earphones that may be used in accordance with various embodiments of the present disclosure.

FIG. 8A illustrates a perspective view of earphones 110. FIG. 8A will generally be described in conjunction with FIG. 8B, which illustrates an example architecture of circuitry that may be used to implement the disclosed technology with earphones 110. Earphones 110 include earphone 800a, which may correspond to a wearer's left ear, and earphone 800b, which may correspond to a wearer's right ear. Generally, the aspects described herein with respect to earphone 800a may apply equally to earphone 800b, and vice versa. As shown in FIG. 8A, earphones 800a and 800b include respective tips 810a and 810b. Earphones 110 may also include controller 820 and cable 815. Cable 815 electrically couples earphones 800a and 800b to one another, and also couples earphones 800a, 800b to controller 820. Additionally, earphones 800a, 800b may in some cases include fin 825 that contacts folds in the outer ear anatomy of the wearer in order to further secure the earphones 800a and/or 800b to the wearer's ear. Although FIG. 8A only depicts a single fin 825 coupled to earphone 800b, it is noted that a similar fin may be detachably coupled to earphone 800a as well, or no such fins may be used at all. Additionally, although FIG. 8A depicts a pair of wireless earphones (i.e. connected wirelessly to a computing device such as computing device 120), wired earphones may also be used in accordance with the present disclosure to implement the technology presented herein.

Earphones 110 may be constructed to have various dimensions, including different diameters, widths, and thicknesses, in order to accommodate different human or animal ear sizes and different preferences. In some embodiments of earphones 110, the housing of each earphone 800a and 800b is a rigid shell that surrounds electronic components within. In some embodiments, these electronic components may include one or more or all of the components described above with respect to electronic capsule 300 (e.g. biosensors, motion sensors, batteries, logic circuits, wireless transmitters/receivers etc.). In other embodiments, referring now to FIG. 8B, examples of the electronic components include one or more of a motion sensor 835, optical heartrate sensor 830, audio-electronic components such as drivers 870a, 870b and speakers 805a, 805b, and other circuitry (e.g., processors 845, 850, and memories 840, 855). One or more of these components may optionally reside outside of earphones 800a, 800b, for example, in controller 820 or elsewhere. The rigid shell of the housing may be made with plastic, metal, rubber, or other materials known in the art. The housing may be cubic shaped, prism shaped, tubular shaped, cylindrical shaped, or otherwise shaped to house the electronic components or to fit well within a wearer's ear.

Referring back to FIG. 8A, tips 810a, 810b may be rounded, parabolic, and/or semi-spherical, so as to comfortably and securely fit within a wearer's ear, with the distal end of tip 810a, 810b contacting a portion of the wearer's outer ear canal. In some embodiments, tip 810a, 810b is removable so as to be exchanged with alternate tips of varying dimensions, colors, or designs to accommodate a wearer's preference and/or fit more closely match the radial profile of the wearer's outer ear canal. Tip 810a, 810b may be made with softer materials such as rubber, silicone, fabric, or other materials as would be appreciated by one of ordinary skill in the art upon studying the present disclosure.

Controller 820 may provide various controls (e.g., buttons and switches) related to media playback, such as, for example, volume adjustment, track skipping, audio track pausing, and the like. Additionally, controller 820 may include various controls related to the gathering of biometrics and/or activity information, such as, for example, controls for enabling or disabling heart rate and/or motion detection. Controller 820 may be of a simple design having, for example, three buttons to perform various of the controls described herein. The buttons of controller may be used in a variety of patterns to control the function and performance of earphones 110 in a variety of ways. For example, double-clicking the middle button may enable and disable heart rate detection; or holding the top button for two seconds followed by holding the bottom button for one second may cause the earphones to generate an audible readout of a user's current heart rate or other measurement (e.g. exercise intensity, exertion, etc.) via speakers 805a, 805b.

Figure 8B:
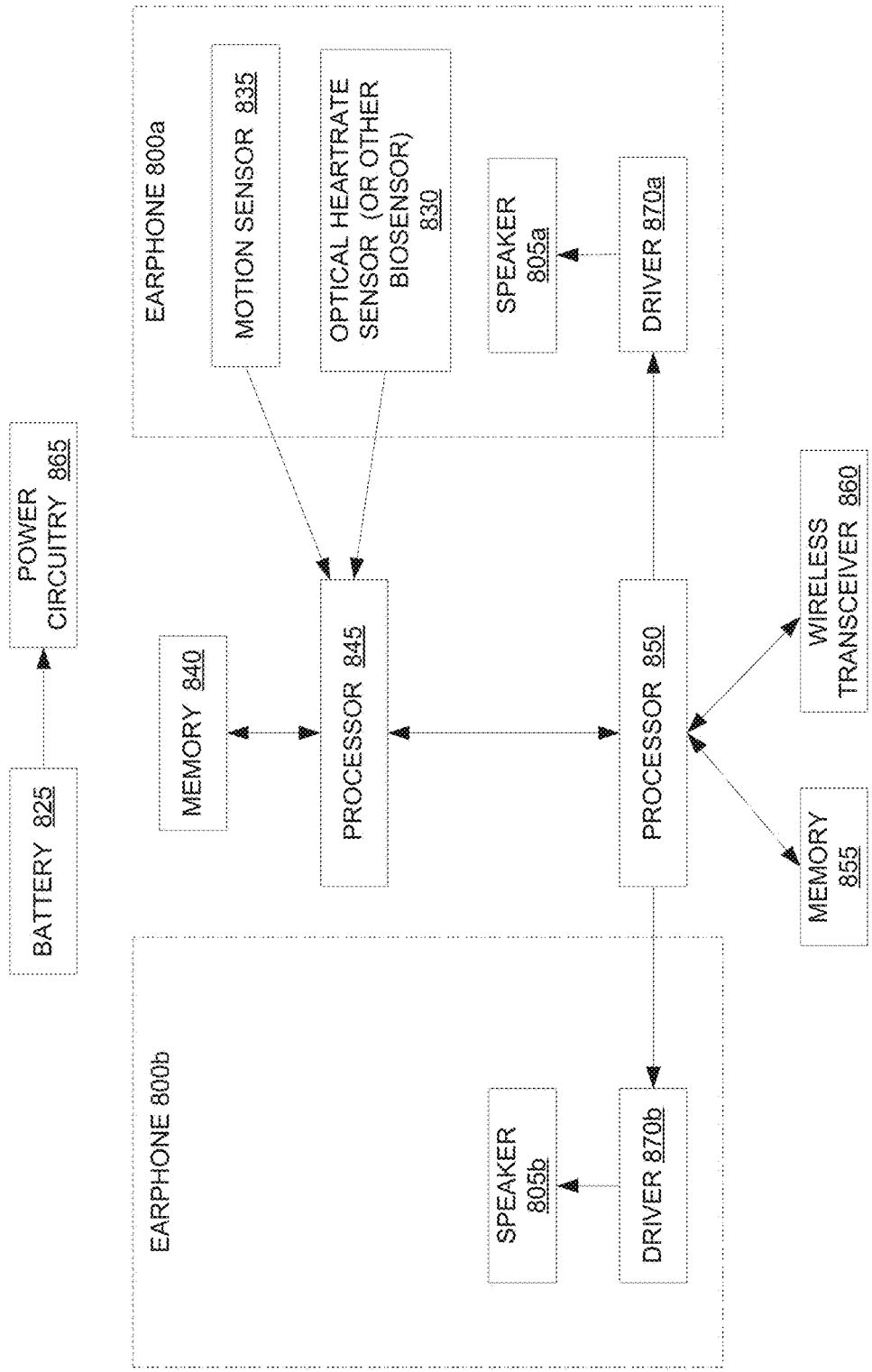
FIG. 8B illustrates an example architecture for circuitry of earphones in accordance with various embodiments of the present disclosure.

With reference to FIG. 8B, the circuitry of earphones 110 may include processors 845, 850 (including, in some instances, logic circuits similar to logic circuits 340), memories 840, 855, wireless transceiver 860, battery 825, power circuitry 865, and other circuitry for earphones 800a, 800b. As further illustrated, earphone 800a may include motion sensor 835, optical heartrate sensor 830 (or other biosensor), speaker 805a, and driver 870a. Earphone 800b may include speaker 805b and driver 870b. Although motion sensor 835 and optical heart rate sensor (or other biosensor) 830 are depicted as being embodied within earphone 800a, it is noted that either one or both of motion sensor 835 and/or optical heart rate sensor (or other biosensor) 830 may be embodied in, distributed throughout, or duplicated within any one or more of earphone 800a, earphone 800b, or controller 820. For example, in some embodiments, earphone 800b may also include a motion sensor (e.g., an accelerometer or gyroscope, generally, similar to motion sensor 835), and/or a biosensor (e.g., optical heartrate sensor 830). In other embodiments, earphone 800a includes the motion sensor 835 and earphone 800b includes the biosensor 830, and so on. In particular, motion sensor 835, including any subcomponents thereof (e.g., as described above), and/ or optical heartrate sensor 830 or other biosensor 830 may be included entirely within a single earphone (e.g., earphone 800a), may be distributed between two earphones 800a, 800b, or may be duplicated within each earphone 800a, 800b in any combination for added precision, such that each earphone 800a, 800b in the pair can detect and activity and biometrics information as desired for particular applications.

Processor 845 may include logic circuits for receiving, processing, and/or storing information gathered by biosensors (e.g., optical heartrate sensor 830) and/or motion sensor 835. More particularly, as illustrated in FIG. 8B, processor 845 may be coupled (e.g., by wired or wireless connection) to motion sensor 835 and/or optical heartrate sensor 830 (or other biosensor), and hence may receive and process electrical signals generated by these sensors 835 and/or 830 in response to the wearer's motion and/or biometrics, respectively. Processor 845 may store such signals or processed versions thereof as biometric data and/or activity data in memory 840, which biometric data and/or activity data may be made available to a computing device 120 using wireless transceiver 860. In some embodiments, memory 840 stores biometric data and/or activity data for transmission by wireless transceiver 860 to computing device 120 for further processing thereby.

During operation, optical heartrate sensor 830 may use a photoplethysmogram (PPG) to optically obtain the user's heart rate. In one embodiment, optical heartrate sensor 830 includes a pulse oximeter that detects blood oxygenation level changes as changes in coloration at the surface of a user's skin. More particularly, in this embodiment, optical heartrate sensor 830 illuminates the skin of the user's ear using a light-emitting diode (LED). Light from the LED penetrates through the epidermal layers of the skin to underlying blood vessels. A portion of the light is absorbed, while a portion of the light is reflected back to optical heartrate sensor 830. The light reflected back through the skin of the user's ear is then obtained with a receiver (e.g., a photodiode) and used to detect changes in the user's blood oxygen saturation ($SpO_2$) and pulse rate, thereby permitting calculation of the user's heart rate using algorithms known in the art (e.g., using processor 840). Optical heartrate sensor 830 may be positioned on one of earphones 800a, 800b such that optical heartrate sensor 830 is proximal to the interior side of a user's tragus when earphones 110 are worn. In other embodiments, optical heartrate sensor 830 may be positioned on one of earphones 800a, 800b so as to be proximal to any other portion of the user's ear (e.g. concha, ear lobe, pinna, antitragus, outer ear canal, etc.) when earphone 800a, 800b is worn by the user.

In this manner, optical heartrate sensor 830 may also be used to generate biometrics that may be used calculate or estimate the wearer's heart rate variability (HRV), i.e. the variation in time interval between consecutive heartbeats. For example, processor 845 or a processor resident in computing device 120 may calculate HRV using the biometrics gathered by optical heartrate sensor 830 based on a time domain methods, frequency domain methods, and/or other methods known in the art that estimate/calculate HRV based on data such as mean heart rate, change in pulse rate over a time interval, and other data used in the art to estimate/calculate HRV. These methods of calculating HRV may also be applied with respect to biometrics gathered using wristband 105 discussed in connection with FIGS. 1-7.

In further embodiments, logic circuits of processor 845 may further detect, calculate, and/or store activity data, based on measured activity of the wearer, such as the wearer's amount of physical activity (e.g., exercise and the like), sleep, or rest over a period of time, or the amount of time without physical activity over a period of time. The logic circuits may use the HRV or HR, the activity data, or some combination of the these to gauge the wearer's response to the activity and other external factors (e.g., temperature, weather, stress, etc.). In various embodiments, the user's response may indicate the user's physical condition and aptitude for further physical activity for the current or next day. In further embodiments, logic circuits may use the HR detected by biosensor 830 (e.g. optical heartrate sensor 830) to compute the user's exercise intensity, and determine/provide the user's exertion value, exertion index, and/or exertion load, as described in further detail herein. These computations and determinations may also be applied with respect to biometrics (e.g. HR) gathered using wristband 105 discussed in connection with FIGS. 1-7.

Referring again to FIG. 8B, during audio playback, earphones 110 may wirelessly receive audio data using wireless transceiver 860. The audio data may then be processed by logic circuits of processor 850, for example, to be converted into electrical signals and delivered to respective drivers 870a, 870b of speakers 805a, 805b, such that the electrical signals may be converted to sound. Drivers 870a, 870b may use various driver technologies known in the art, for example, moving coil drivers, electrostatic drivers, electret drivers, orthodynamic drivers, and other transducer technologies may be used. In some embodiments, the biometrics and other computations and determinations may be provided to the user via an audible sound through one or more of the speakers 805a, 805b. For example, a user's exertion value may be determined by logic circuits to be 9.3 (based on biometrics detected by biosensor 830), and upon request from the user (e.g. via pressing the controller 820 buttons in an appropriate pattern, or otherwise) a programmed voice may recite the words "your exertion at present is nine-point-three," or the like.

Wireless transceiver 860 may be configured to transmit/receive biometric data, and/or activity data, and/or audio data across link 125 and 130, for example using available wireless communications protocols/standards or methods. In some embodiments, wireless transceiver 860 may utilize BLUETOOTH, ZIGBEE, Wi-Fi, GPS, cellular technology, or some combination thereof. Further, although FIG. 8B illustrates a single wireless transceiver 860 for transmitting/receiving biometrics, activity and audio data, in an alternative embodiment, separate transceivers may be dedicated for communicating biometric data to/from computing device 120, for communicating activity data to/from computing device 120, and for communicating audio data to/from computing device 120. In some cases, transceiver 860 may include a low energy transmitter such as a near field communications (NFC) transmitter or a BLUETOOTH low energy (LE) transmitter. In further example implementations, a separate wireless receiver may be provided for receiving high fidelity audio data from an audio source. In yet additional embodiments, a wired interface (e.g., micro-USB) may be used for communicating data stored in memories 840 and/or 855.

FIG. 8B also shows that earphones 110 may be powered by battery 825, which may be coupled to power circuitry 865. Any suitable battery or power supply technologies known in the art may be used. For example, a lithium-ion battery, aluminum-ion battery, piezo or vibration energy harvesters, photovoltaic cells, or other like devices may be used. In some deployments of earphones 110, battery 825 may be enclosed in one or more of earphone 800a or 800b.

Alternatively, battery 825 may be enclosed in controller 820. The circuitry of earphones 110 described herein may be configured to enter a low-power or inactive mode when earphones 110 are not in use, or in other scenarios where low-power operation is appropriate. For example, mechanisms such as an on/off switch, a BLUETOOTH transmission disabling command, or the like may be provided by controller 820, such that a user may manually control the on/off state of one or more power-consuming components or circuits of earphones 110.

It should be noted that in various embodiments, processors 845 and 850, memories 840 and 855, wireless transceiver 860, battery 825, and power circuitry 865 may be enclosed in and/or distributed throughout either or both of earphone 800*a*, earphone 800*b*, and controller 820. For example, processor 845 and memory 840 may be enclosed in earphone 800*a* along with optical heartrate sensor 830 and motion sensor 835. In this particular scenario, these components may be electrically coupled to one or more printed circuit boards (PCBs) enclosed in earphone 800*a*. Additionally, any one or more of these components may be duplicated in each of earphones 800*a*, 800*b*. It should also be noted that although processors 845 and 850 are illustrated as being separate from one another, the functions of processors 845 and 850 may be integrated into a single processor.

Figure 9C:
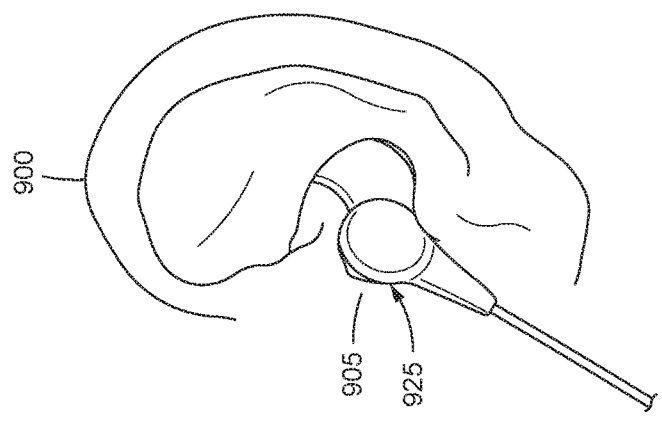
FIG. 9C illustrates a frontal perspective view of embodiments of an example earphone placed in a user's ear in accordance with the present disclosure.
Figure 9B:
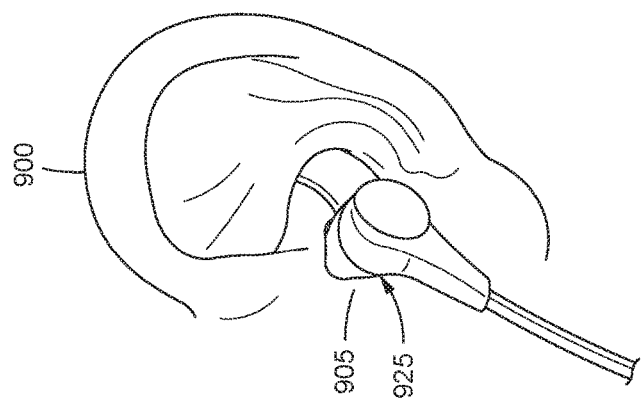
FIG. 9B illustrates a side view of embodiments of an example earphone placed in a user's ear in accordance with the present disclosure.
Figure 9A:
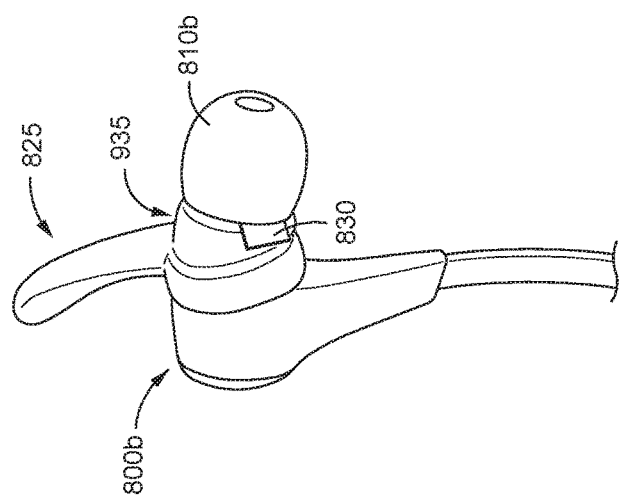
FIG. 9A illustrates a perspective view of embodiments of an example earphone in accordance with the present disclosure.

FIG. 9A illustrates a perspective view of embodiments of earphone 800*b*. As shown, earphone 800*b* may include optical heartrate sensor 830, as generally described above. FIG. 9A will also be described in conjunction with FIGS. 9B and 9C, which show various perspective views illustrating example arrangements/orientations of optical heartrate sensor 830 when earphone 800*b* (or 800*a*) is worn in a user's ear 900. As shown, earphone 800*b* may include housing 935, tip 810*b*, fin 825, and optical heartrate sensor 830. Optical heartrate sensor 830 protrudes from a frontal side of housing 935, proximal to tip 810*b*, and proximal to a nozzle (not shown, but within the hollow of the tip 810*b*) of earphone 800*b*. FIGS. 9B and 9C illustrate interface 925 of optical heartrate sensor 830 and ear 900 when earphone 800*b* is worn in a user's ear 900. In the illustrated embodiments, when earphone 800*b* is worn, optical heartrate sensor 830 is proximal to the interior side of the user's tragus 905. In various embodiments, earphones 800*a*, 800*b* may be dual-fit earphones shaped to be comfortably and securely worn in either an over-the-ear configuration or an under-the-ear configuration. The secure fit provided in such embodiments aids in keeping optical heartrate sensor 830 positioning on the interior side of tragus 860, thereby ensuring accurate and consistent measurements of a user's heart rate and/or other biometric information.

Figure 9F:
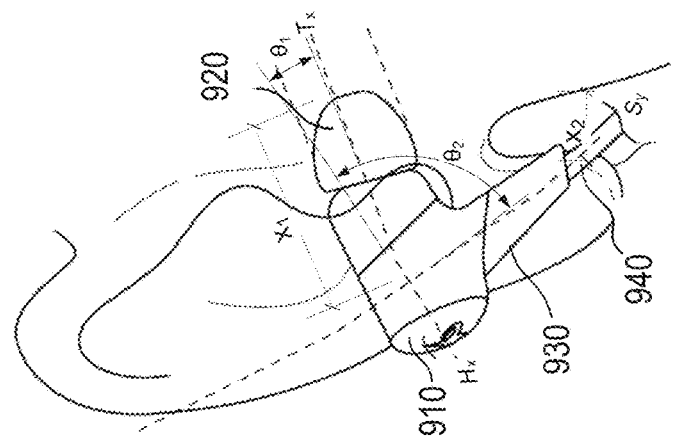
FIG. 9F illustrates a cross-sectional view of an example earphone in accordance with various embodiments of the present disclosure.
Figure 9E:
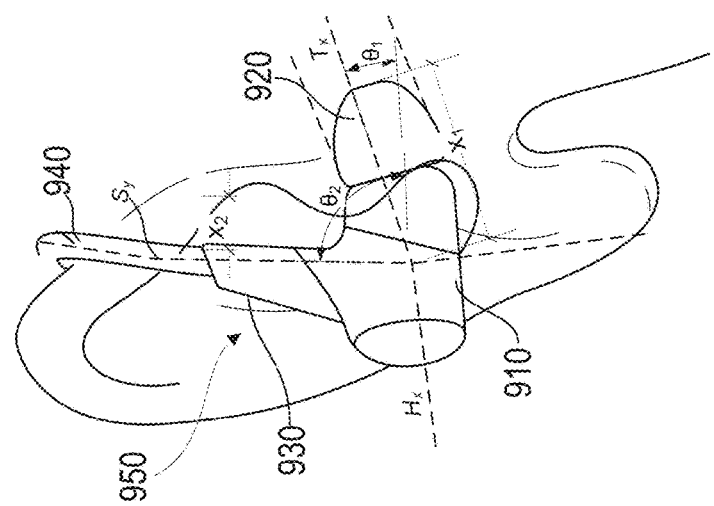
FIG. 9E illustrates a cross-sectional view of an example earphone in accordance with various embodiments of the present disclosure.
Figure 9D:
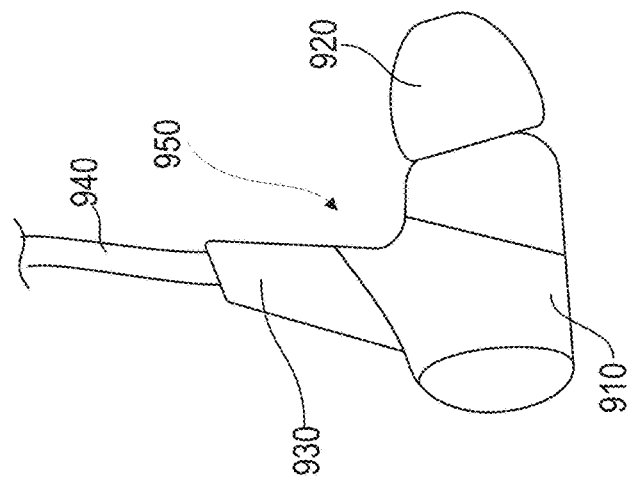
FIG. 9D illustrates a cross-sectional view of an example earphone in accordance with various embodiments of the present disclosure.

FIGS. 9D and 9E illustrate earphones 950 in an over-the-ear configuration, where FIG. 9F illustrates earphones 950 in an under-the-ear configuration. As illustrated, earphone 950 includes housing 910, tip 920, strain relief 930, and cable 940. The proximal end of tip 920 mechanically couples to the housing 910 near the distal end of the housing, often by coupling to an extension of the housing called a nozzle. Similarly, the distal end of strain relief 930 mechanically couples to a side (e.g., the top side) of housing 910. Furthermore, the distal end of cable 940 may be disposed within (or simply coupled to) and secured by the proximal end of strain relief 930.

Referring to FIGS. 9E and 9F, the longitudinal axis of housing 910, $H_x$, forms angle $\theta_1$ with respect to the longitudinal axis of tip 920, $T_x$. The longitudinal axis of strain relief 930, $S_y$, may align with the proximal end of strain relief 930 and form angle $\theta_2$ with respect to the axis $H_x$. In some embodiments, $\theta_1$ is greater than 0 degrees, e.g., $T_x$ extends in at an angle from $H_x$, or in other words, tip 920 may be angled with respect to housing 910. The value of $\theta_1$ may be selected to approximate the ear canal angle of the wearer. For example, $\theta_1$ may range between 5 degrees and 15 degrees, and may extend from 0 degrees 45 degrees. Also, $\theta_2$ may be less than 90 degrees, e.g., such that $S_y$ extends at a non-orthogonal angle from $H_x$, or in other words, strain relief 930 is angled with respect to a perpendicular orientation with housing 910. In some embodiments, $\theta_2$ may be selected to direct the distal end of cable 940 closer to the wearer's ear. For example, $\theta_2$ may range between 75 degrees and 89 degrees, but may extend to as low as 45 degrees in some situations.

As further illustrated in FIGS. 9E and 9F, $X_1$ may represent the distance between the distal end of tip 920, on the one hand, and the intersection of strain relief 930's longitudinal axis $S_y$ and housing longitudinal axis $H_x$, on the other hand. One of skill in the art will appreciate, upon studying the present disclosure, that the dimension $X_1$ may be selected based on several parameters, including, for example, the desired fit to a wearer's ear based on the average human ear anatomical dimensions, the types and dimensions of electronic components (e.g., optical heartrate sensor 830, motion sensor 835, processors 845 and 850, memories 840 and 855, other components described in connection therewith, and so on) that may be disposed within housing 910 and tip 920, and based on the specific placement of optical heartrate sensor 830. In some examples, $X_1$ may be at least 18 mm. However, in other examples, $X_1$ may be smaller or greater based on the parameters discussed above.

Referring again to FIGS. 9E and 9F, $X_2$ may represent the distance between the proximal end of strain relief 930 and the surface of the wearer's ear/neck/head. In the configuration illustrated in FIG. 9E, $\theta_2$ may be selected to reduce $X_2$, as well as to direct cable 940 toward the wearer's ear, such that cable 940 may rest in the crevice formed where the top of the wearer's ear meets the side of the wearer's head. In some embodiments, θ2 may range between 75 degrees and 89 degrees, but may extend to as low as 45 degrees in some situations. In the configuration illustrated in FIG. 9F, $\theta_2$ may be selected to reduce $X_2$, as well as to direct cable 940 near to the profile of the user's head/neck so as to avoid obstructions as nearly as possible while the user performs various activities.

In some examples, strain relief 930 may be made of a flexible material such as rubber, silicone, or soft plastic, so as to enable strain relief 930 to be bent toward the wearer's ear. Similarly, strain relief 930 may include a shape memory material so as to retain the shape thereof after being bent inward. In some examples, strain relief 930 may be shaped to curve inward towards the wearer's ear.

As one having skill in the art will appreciate from the foregoing discussion, that earphones 110 and wristband 105 may in various embodiments gather biometric data and activity data that may be used to track a user's activities and activity level. The biometric data and activity data may then be made available to computing device 120, which may provide a GUI for interacting with the data using a tracking application installed on computing device 120. FIG. 10A is a block diagram illustrating example components of computing device 120, including an installed tracking application (occasionally referred to as an app) 1015.

With continued reference to FIG. 10A, computing device 120 may include connectivity interface 1005, storage 1010 that stores tracking application 1015, processor 1020, graphical user interface (GUI) 1025 that may be provided on display 1030, and bus 1035 for transferring data between the various components of computing device 120. Connectivity interface 1005 connects computing device 120 to earphones 110 and/or wristband 105 through a communication medium (e.g., links 125 and 130). Storage 1010 may include volatile memory (e.g. RAM), non-volatile memory (e.g. flash storage), or some combination/variation thereof. In various embodiments, storage 1010 may store biometric data and/or activity data collected by earphones 110 and/or wristband 105. Additionally, storage 1010 may store tracking application 1015 that, when executed by processor 1020, receives input (e.g., by a conventional hard/soft key or a touch screen, voice detection, or other input mechanism), and allows a user to interact with the collected biometric and/or activity data.

In various embodiments, a user may interact with tracking application 1015 via GUI 1025, which may be provided by display 1030, for example, via a touchscreen display that accepts various hand gestures as inputs. Tracking application 1015 may process the biometric and/or activity data collected by earphones 110 and/or wristband 105, and present the data via display 1030. Before describing tracking application 1015 in further detail, it should be noted that in some embodiments earphones 110 and band 105 may filter and/or preprocess the collected biometric and activity data prior to transmitting the same to computing device 120. Accordingly, although the embodiments disclosed herein are described with reference to tracking application 1015 processing the received data, in various implementations, preprocessing operations, and/or any one or more of the other processing operations disclosed herein, may be performed by processors 845 or 850 of earphones 110, or by logic circuits 340, prior to transmission of the data to computing device 120.

Tracking application 1015 may be initially configured/setup (e.g., after installation on a smartphone or other computing device 120) based on a user's self-reported biological information, sleep information, and activity preference information. For example, during setup, the user may be prompted via display 1030 to enter biological information such as the user's gender, height, age, weight, etc. In other examples, during setup (or at another time thereafter), the user may be prompted via display 1030 to enter known or estimated biometric or other information such as the user's maximum achieved heartrate, the user's resting heart rate, the user's average activity level during a normal day, etc. Further, during setup the user may also be prompted for sleep information, such as the amount of sleep needed by the user and the user's regular bed/wake time. Further still, the user may be prompted during setup for a preferred activity level and/or intensity, as well as their goals for the same, as well as particular types of activities the user desires to be tracked (e.g., running, walking, swimming, dancing, biking, hiking, etc.) In various embodiments of the disclosure, this self-reported information may be used in tandem with the information collected by earphones 110 and/or wristband 105. For example, a user may initially enter an estimate that their resting heart rate is 100 beats per minute (BPM), but as the user uses earphones 110 and/or wristband 105 the biosensors therein detect that the user's resting heart rate is/has become 105 BPM, and thereby may update the biometrics stored for the given user. In some embodiments these updates (i.e. learning) take place automatically, and in other embodiments are only incorporated upon prompting the user (e.g. via display 1030) regarding the change and receiving an approval by the user to make the change. In this way, one or more of computing device 120, earphones 110, and/or wristband 105 may learn—automatically, or in a prompt-by-prompt fashion—details about the user that may be incorporated in providing a more granular view of the user's exercise intensity, exertion, recovery, performance profile, etc.

Following the setup, tracking application 1015 may be used by a user to monitor activity and biometrics of the user (e.g., based on information collected from sensors 835 and 830). As further illustrated in FIG. 10B, tracking application 1015 may include various modules, such as, for example display module 1050, biosensor module 1055, exertion module 1060, and motion sensor module 1065. These modules may be implemented separately or in combination. Each module may include computer-readable media and have computer-executable code stored thereon (or stored on and/or accessible via other storage locations on storage 1010), such that the code may be executed by processor 1020 (e.g., in some cases in conjunction with other processing modules 1070) to perform specific functions and/or transformations (e.g., as described herein with regard to various flow charts, etc.) with respect to biometric and/or activity data available to tracking application 1015 through the various components of computing device 120. As will be further described below, display module 1050 may present (e.g., via display 1030) various screens to a user, with the screens containing graphical representations of information provided by tracking application 1015. In further embodiments, tracking application 1015 may be used to display to the user an instruction for wearing and/or adjusting earphones 110.

FIG. 11 is an operational flow diagram illustrating an example method 1100 that provides an earphone adjustment feedback loop to increase the likelihood of accurate biometric data collection by earphones 110. At operation 1110, tracking application 1015 may be executed, which may in turn result in displaying an instruction to the user on how to wear/adjust earphones 110 to obtain an accurate and reliable signal from optical heartrate sensor 830 and/or motion sensor 835. Operation 1110 may occur only once, upon installation of tracking application 1015, may occur once per day (e.g., when the user first wears earphones 110 in the day), or at any customizable, programmable, and/or predetermined interval. Indeed, method 1100 may automatically prompt the user to adjust the earphones upon detecting a low signal quality (e.g. low S/N ratio).

Operation 1120 involves providing feedback (e.g., by a display such as display 1030 on computing device 120) to the user regarding the quality of the signal received from one or both of optical heartrate sensor 830 and/or motion sensor 835, based on the positioning of earphones 110. For example, a signal quality bar or other graphical elements may be displayed to the user. Alternatively, an audio signal and/or vibration signal may be used to provide the feedback or indicate that adjustments need to be made.

At decision 1130, it is determined if the biosensor signal quality is satisfactory for accurate biometric and activity data to be gathered/used. In various embodiments, this determination may be based on factors such as, for example, the frequency with which optical heartrate sensor 830 is collecting heart rate data and/or with which motion sensor 835 is collecting activity information, the variance in the measurements of optical heartrate sensor 830 and/or activity information (including location-based information), dropouts in heart rate measurements by sensor 830, the signal-to-noise ratio approximation of optical heartrate sensor 830 and/or motion sensor 835, the amplitude of the signals generated by sensors 835 and/or 830, and the like.

If the signal quality is determined (e.g., at decision 1130) to be unsatisfactory, at operation 1040, tracking application 1015 may display instructions for adjusting earphones 110 to improve the signal, and operations 1120 and decision 1130 may subsequently be repeated. For example, instruction on adjusting strain relief 930 of earphone 950 may be displayed. Otherwise, if the signal quality is satisfactory, at operation 1150, tracking application 1015 may display confirmation of good signal quality and/or good position of earphones 110. Subsequently, tracking application 1015 may proceed with normal operation.

As one of ordinary skill in the art will appreciate, method 1100 may similarly be applied in the context of wristband 105—replacing "EARPHONES" with "WRISTBAND" in FIG. 11.) and applying analogous operations to those described above in connection with earphones 110.

Figure 12A:
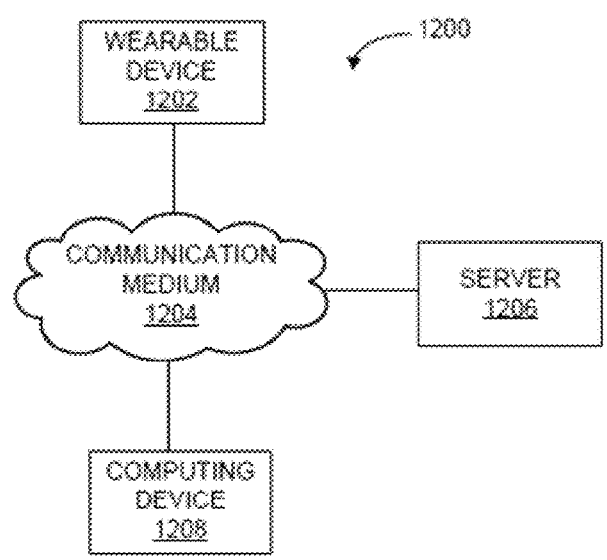
FIG. 12A is an example system in which various embodiments of the disclosure may be implemented.

FIG. 12A illustrates example system 1200 in which various embodiments of the disclosure may be implemented. By way of example, system 1200 may be used to determine exertion of a user. System 1200 includes wearable device 1202 (e.g. wristband 105, earphones 110), communication medium 1204, server 1206, and computing device 1208. Embodiments of system 1200 are capable of capturing and tracking robust information related to a user's activity, including information about the user's activity type, duration, intensity, and so on. Moreover, embodiments of system 1200 are also capable of capturing and tracking robust information related to a user's biometrics. This wealth of information, which may be gathered by various sensors as described herein, may be used to provide user-specific exertion measures and/or exercise intensity measures that are based on biometric data and/or activity data. Being user-specific and time referenced, the exertion provided by system 1200 may be personalized, accurate, and continually updated. Further, in some embodiments, a model may be created based on the user's exercise intensity (which is further based on the biometric data collected), such that the exertion provided by the systems, methods, and devices of the present disclosure represent an accumulated measure of exercise intensities captured during a critical time frame (e.g. a time frame within which a user's prior exercise intensity effects their current level of exertion) of use. A precise and personalized exertion measure of this nature may allow the user to make informed decisions and assessments regarding the user's exercise regimen and/or lifestyle. For example, providing an athlete with a precise and personalized exertion measure, as disclosed herein, enable athletes to more intelligently modify, track, or gauge the effectiveness of their training regimen, project the impact of a particular activity on their physical condition at a given moment after a previously performed activity, or to make other such exertion based assessments.

An accurate and personalized response profile of the above-described nature may allow the user to make informed decisions regarding the user's training load and/or lifestyle, thus achieving maximum performance and balance. For example, the response profile may generally indicate how a user is likely to respond to a given training load or other activity or set of conditions. This indication, in some embodiments, represents the user's performance capacity (e.g., the user's capacity to undertake a given training load, perform a given activity, etc.). Such an indication may be provided to a user in one or more of an audio, visual, numerical, descriptive, or graphical representation (e.g., via display 1030 of computing device 120, etc.). For instance, if the indication is provided on a scale from 0 to 100, and the response profile indicates a 75 on this scale, this indication may be provided to a user in a bar graph, a scale, a numeral, a digital gauge, a textual description, or the like (e.g., a bar graph depicted as being filled ¾ of the way). In some such embodiments, a 0 on the response profile scale may represent little to no capacity to perform the activity (e.g., the user's biometrics reflect that the user has been working or active for 24 hours straight with no sleep, and the user thus needs rest immediately), and a 100 on the response profile scale may represent full capacity (e.g., the user's biometrics reflect that the user is well-rested and otherwise ready for activity). Of course, any scale may be implemented without departing from the scope of the present disclosure, as indicated previously. Thus, the response profile created and provided by the systems, methods, and devices of the present disclosure may enable a user to intelligently assess the user's capacity for activity, whether to be undertaken immediately or sometime in the future.

Referring again to FIG. 12A, wearable device 1202 may include in some embodiments, wristband 105 or earphones 110. Communication medium 1204 may be used to connect or communicatively couple wearable device 1202, server 1206, and/or computing device 1208 to one another or to a network, and communication medium 1204 may be implemented in a variety of forms. For example, communication medium 1204 may include an Internet connection, such as a local area network (LAN), a wide area network (WAN), a fiber optic network, internet over power lines, a hard-wired connection (e.g., a bus), and the like, or any other kind of network connection. Communication medium 1204 may be implemented using any combination of routers, cables, modems, switches, fiber optics, wires, radio (e.g., microwave/RF links), and the like. Further, communication medium 1204 may be implemented using various wireless standards, such as Bluetooth®, Wi-Fi, 3GPP standards (e.g., 2G GSM/GPRS/EDGE, 3G UMTS, or 4G LTE), etc. Upon reading the present disclosure, one of skill in the art will recognize other ways to implement communication medium 1204 for communications purposes.

Server 1206 generally directs communications made over communication medium 1204. Server 1206 may include, for example, an Internet server, a router, a desktop or laptop computer, a smartphone, a tablet, a processor, a module, or the like, and may be implemented in various forms, include, for example, an integrated circuit, a printed circuit board, or in a discrete housing/package. In one embodiment, server 1206 directs communications between communication medium 1204 and computing device 1208. For example, server 1206 may update information stored on computing device 1208, or server 1206 may send/receive information to/from computing device 1208 in real time. Server 1206 may also be used to implement cloud computing capabilities for wearable device 1202 and/or computing device 1208. Indeed, any one or more of the data processing or preprocessing operations discussed herein may be performed at server 1206.

It should be noted that computing device 1208 may take a variety of forms, such as a desktop or laptop computer, a smartphone, a tablet, a smartwatch or other wearable electronic device, a processor, a module, earphones, or the like. By way of illustration, computing device 1208 may include a processor or module embedded in a wearable sensor, a bracelet, a smart-watch, a piece of clothing, an accessory, and so on. Computing device 1208 may be, for example, substantially similar to devices embedded in electronic capsule 200, which may be embedded in and/or removable from wristband 105, as illustrated in FIGS. 2 through 7 and described herein. Computing device 1208 may communicate with other devices over communication medium 1204 with or without the use of server 1206. In one embodiment, wearable device 1202 includes computing device 1208. Further, computing device 1208 may in some cases be computing device 120 or be substantially similar thereto, and in this regard, the description of computing device 120 herein may apply equally to computing device 1208, and vice versa. In various embodiments, wearable device 1202 or computing device 1208 may be used to perform various processes described herein and/or may be used to execute various operations described herein with regard to one or more disclosed systems and methods. Upon studying the present disclosure, one of skill in the art will appreciate that system 1200 may in some embodiments include multiple wearable devices 1202, communication media 1204, servers 1206, and/or computing devices 1208.

Figure 12B:
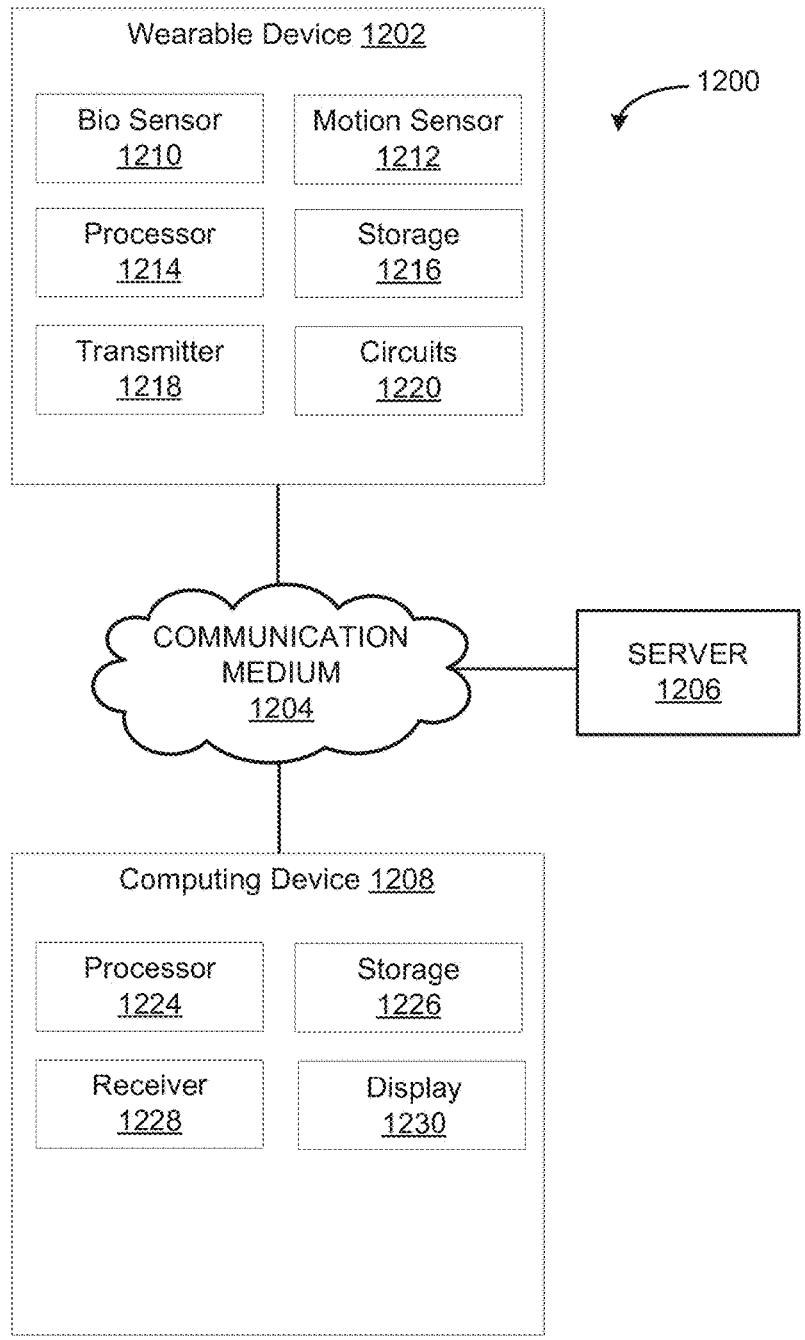
FIG. 12B is an example system in which various embodiments of the disclosure may be implemented.

FIG. 12B illustrates one embodiment of system 1200, and specifically, provides further detail of some example implementations of wearable device 1202 and computing device 1208, in accordance with the present disclosure. In the embodiments of FIG. 12B, wearable device 1202 may include biosensor 1210 and/or motion sensor 1212. In one specific example, wearable device 1202 further includes processor 1214. Processor 1214 may be coupled to biosensor 1210 and/or motion sensor 1212, and may be configured to process electrical signals generated by biosensor 1210 and/or motion sensor 1212. Such signals may be indicative of biometrics and/or activity, as will is described in further detail herein. Biosensor 1210 may be implemented as any of the various sensors described herein for measuring biometrics of a user—e.g., with respect to FIGS. 1 through 11. In this connection, biosensor 1210 may include one or more sensors, e.g., finger biosensor 320, wrist biosensor 310, and optical heartrate sensor 830. Likewise, motion sensor 1212 may be implemented as any of the various motion sensors described herein for detecting motion (e.g., by way of various inertial units), as described, e.g., with reference to FIGS. 1 through 11.

Furthermore, wearable device 1202 may include circuits 1220 that receive and process the electrical signals from biosensor 1210 and/or motion sensor 1212. For example, circuits 1220 may include an analog-to-digital converter, an encoder, modem circuitry, and the like, that receive electrical signals from biosensor 1210 and/or motion sensor 1212 and process the electrical signals into a format that may be acceptable to processor 1214 or that may be transmitted over communication medium 1204 by transmitter 1218. Although not depicted, in some embodiments transmitter 1218 may be a transceiver that can both send and receive such signals over communication medium 1204. Storage 1216 may also be included in embodiments of wearable device 1202, and may be used to store activity data and/or biometric data generated from the electrical signals output by biosensor 1210 and/or motion sensor 1212. This stored data may then be processed by processor 1214 and used locally to wearable device 1202, or be transmitted by transmitter 1218. Additionally, storage 1216 and 1226 may include non-transitory computer-readable media having instructions stored thereon that, when executed, cause processor 1214 and/or 1224 to perform various functions, including, by way of example, any of the operations described with reference to methods 1300 (and FIGS. 13A-13F) and elsewhere herein, and to make various calculations, or control or communicate with any of the other various other hardware components described herein. It should further be noted that storage 1216 may also be used to store/archive such calculations/computations, e.g., exercise intensity measures and exertion measures, determined and provided in accordance with various embodiments of the disclosed technology.

As further depicted in FIG. 12B, system 1200 for determining performance capacity also includes receiver 1228. Receiver 1228 may be part of and/or embedded within computing device 1208 (e.g., may be implement at least in part as an integrated circuit). Receiver 1228 may be a wireless receiver configured to wirelessly receive biometric data and/or activity data. For example, receiver 1228 may receive the biometric and activity data over communications medium 1204 from transmitter 1218. The biometric data may be indicative of biometrics measured by biosensor 1210 in wearable device 1202, and the activity data may be indicative of activity data monitored by motion sensor 1212. Although not depicted in FIG. 12, in some embodiments receiver 1228 may be a transceiver that can both send and receive such data over communication medium 1204.

FIGS. 13A-13F illustrate flow charts depicting various operations of an exemplary computer-implemented method 1300 and accompanying embodiments for determining exertion in accordance with the present disclosure. The operations and sub-operations of method 1300 may be carried out, in some cases, by one or more of the components/elements/devices/modules of communication environment 100, earphones 110, wristband 105, computing device 120, tracking application 1015, and/or system 1200—described above with reference to FIGS. 1 through 12B—as well as sub-components/elements/devices/modules depicted therein or described with respect thereto. In such instances, the description of method 1300 may refer to the corresponding component/element, but in any case, one of skill in the art will recognize when the corresponding component/element may be used, whether or not there is explicit reference thereto. Further, it will be appreciated that such references do not necessarily limit method 1300 to the particular component/element referred to. Thus, it will be appreciated by one of skill in the art that aspects and features described above in connection with (sub-) components/elements/devices/modules, including variations thereof, may be applied to the various operations described in connection with method 1300. It will further be appreciated by one of skill in the art that use of the terms operation and sub-operation may in some instances be used interchangeably. Generally, method 1300 facilitates determining a user's exertion—including an Exertion Value, and/or an Exertion Load and/or an Exertion Index—during or throughout an activity, exercise session, or predetermined time period, and based on one or more of the user's measured biometrics, e.g., heart rate.

Figure 13A:
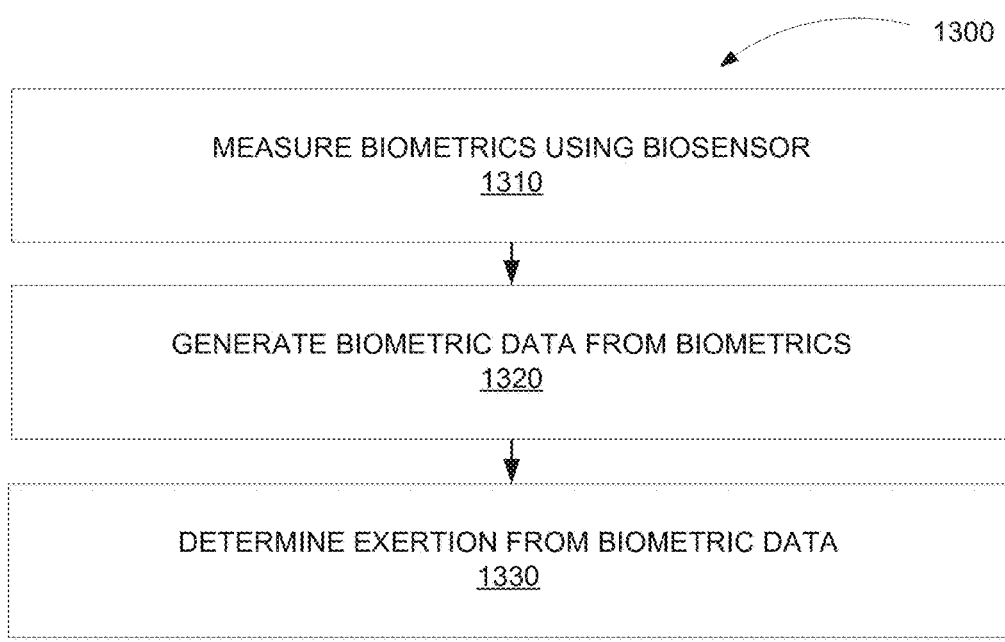
FIG. 13A is an example operational flow diagram illustrating various operations that may be performed to determine exertion in accordance with various embodiments of the present disclosure.

Referring now to FIG. 13A, at operation 1310, method 1300 entails measuring biometrics using a biosensor (e.g. biosensor 1210). The biosensor may be embedded in a wearable device 1202 (e.g. earphones 110, wristband 105, etc.). Measuring biometrics may include measuring a user's heart rate and/or estimating the user's HRV, for example. Biometrics may also include the user's temperature, blood pressure, and other characteristics of the user. Biometrics may be measured continuously or periodically. For example, in some cases, it may be desirable to determine the user's heart rate once every second, once every five seconds. In other cases it may be desirable to continuously monitor the user's heart rate. At operation 1320, method 1300 may include generating biometric data from the biometrics. This may involve circuits 1220 converting electrical signals from biosensor 1210 to a format that processor 1214 may process, store in storage 1216, and/or transmit by transmitter 1218. For example, biometric data may be generated from biometrics through analog-to-digital conversion, filtering of the biometrics, and/or encoding of the biometrics or data indicative thereof. Additionally, operation 1320 may also be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to generate biometric data from the biometrics monitored by biosensor 1210, including using circuits 1220.

At operation 1330, method 1300 determines an exertion measure based on the biometrics and/or biometric data from operations 1310 and/or 1320. As indicated earlier, embodiments of the present disclosure are directed toward systems, methods and devices for determining and providing a user with their exertion (e.g. exertion level/value, exertion load, exertion index) as a measure of accumulated exercise intensity values (i.e. measures) taken over the course of an exercise session, a portion of an exercise session, or other specified activity or timeframe. As explained in more detail in FIGS. 13B-13C, exercise intensity values are based on the biometrics and/or biometric data from operations 1310 and/or 1320. Operation 1330 of method 1300 may then determine and provide an exertion measure (e.g. exertion value, exertion load, exertion index, etc.) to the user. This will be described in more detail with reference to FIGS. 13B-13E, which illustrate, by way of example and not by way of limitation, how operation 1330 of method 1300 may be implemented to provide exertion in accordance with some embodiments of the technology disclosed herein.

Figure 13B:
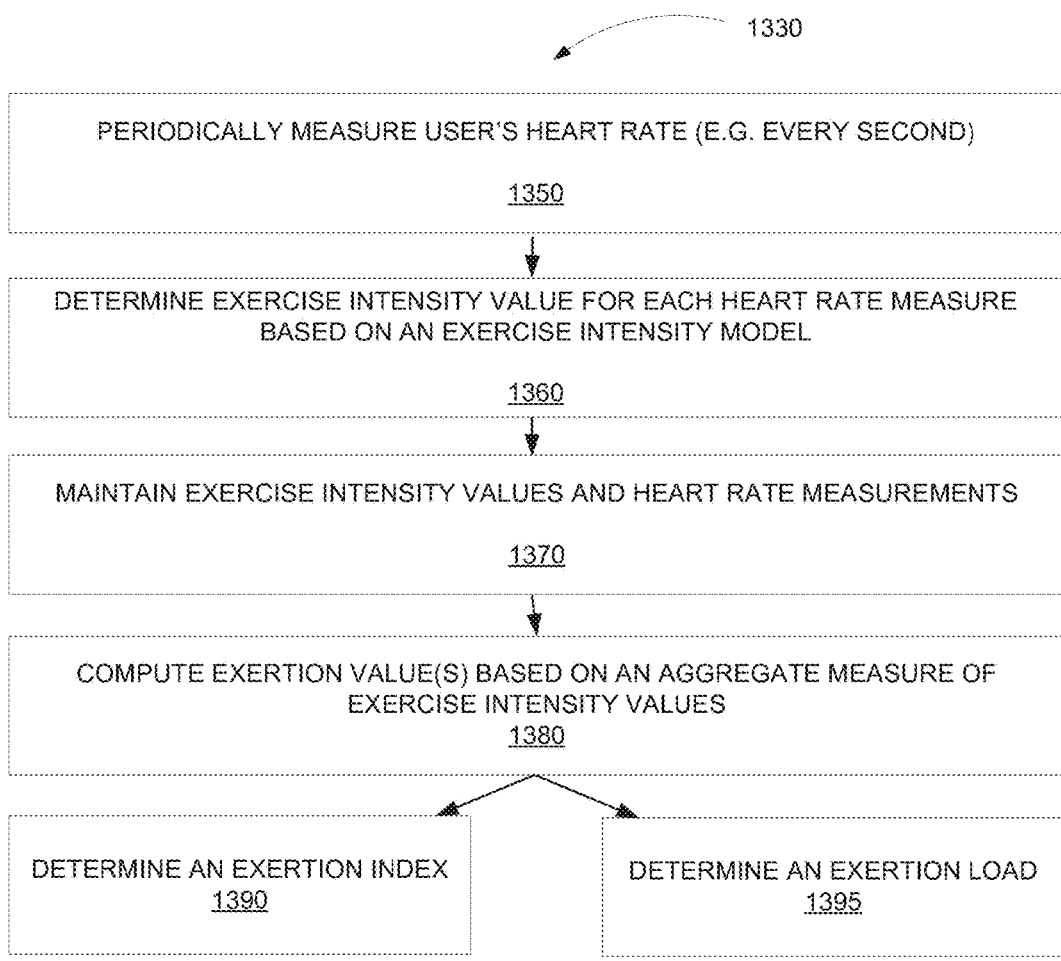
FIG. 13B is an example operational flow diagram illustrating various operations that may be performed to determine exertion in accordance with various embodiments of the present disclosure.

FIG. 13B provides an operation flow diagram of some embodiments of method 1300 and in particular of operation 1330. At operation 1350, method 1300 periodically measures or detects the user's heart rate using, e.g. biosensor 1210. For each heart rate measurement detected, operation 1360 determines an exercise intensity value—based on an exercise intensity model—that corresponds to the heart rate measured for that particular user. At operation 1370, method 1300 may optionally maintain or store one or more of the heart rate measurements detected at operation 1350 and/or one or more of the exercise intensity values determined at operation 1360. At operation 1380, method 1300 computes an exertion value based on one or more of the exercise intensity values determined at operation 1360. The computations at operation 1380 are based on exercise intensity values taken in the aggregate over a particular time frame, and may be weighted according to their proximity in time to the present. For instance, in a user's exercise intensity (and corresponding exercise intensity value) determined from five minutes ago may be weighted less than the exercise intensity value from one minute ago in assessing and computing exertion (because it has less of an impact on the user's present condition), and the resulting exertion measures computed at operations 1380, 1390 and 1395 may reflect this weighting. At operation 1390, method 1300 may use the exertion value(s) computed at operation 1380 to compute/determine an exertion index. At operation 1395, method 1300 may use the exertion value(s) computed at operation 1380 to compute/determine an exertion load. Some operations of method 1300 will be further detailed in connection with some example embodiments discussed below.

Figure 13C:
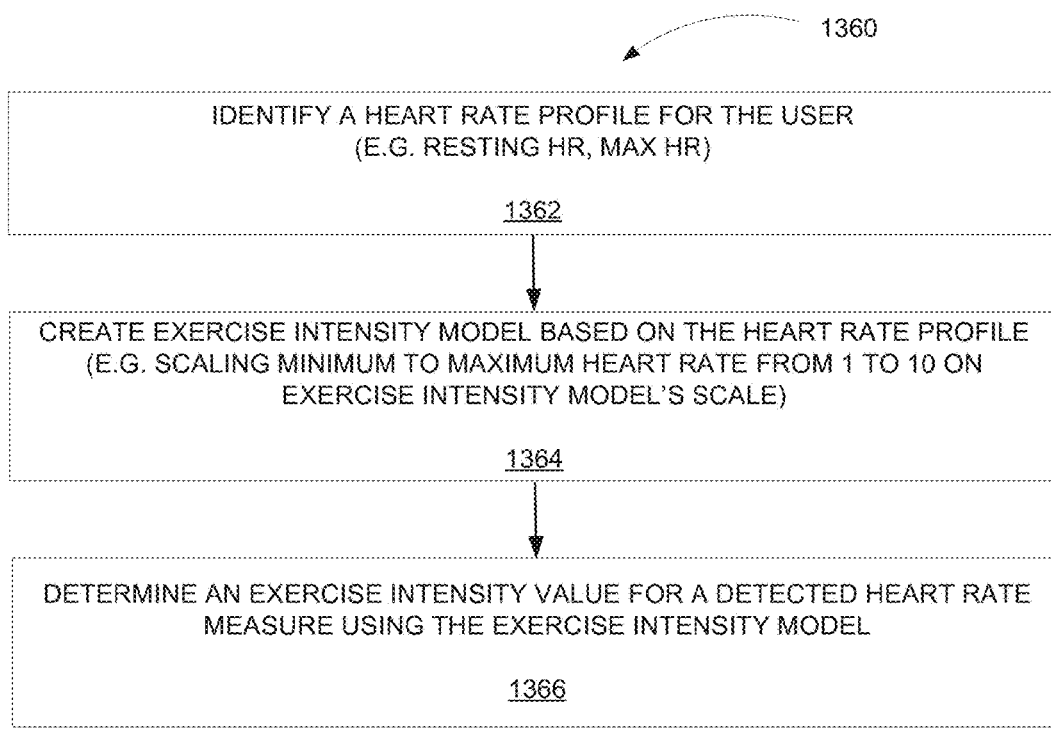
FIG. 13C is an example operational flow diagram illustrating various operations that may be performed to determine exertion in accordance with various embodiments of the present disclosure.
Figure 13D:
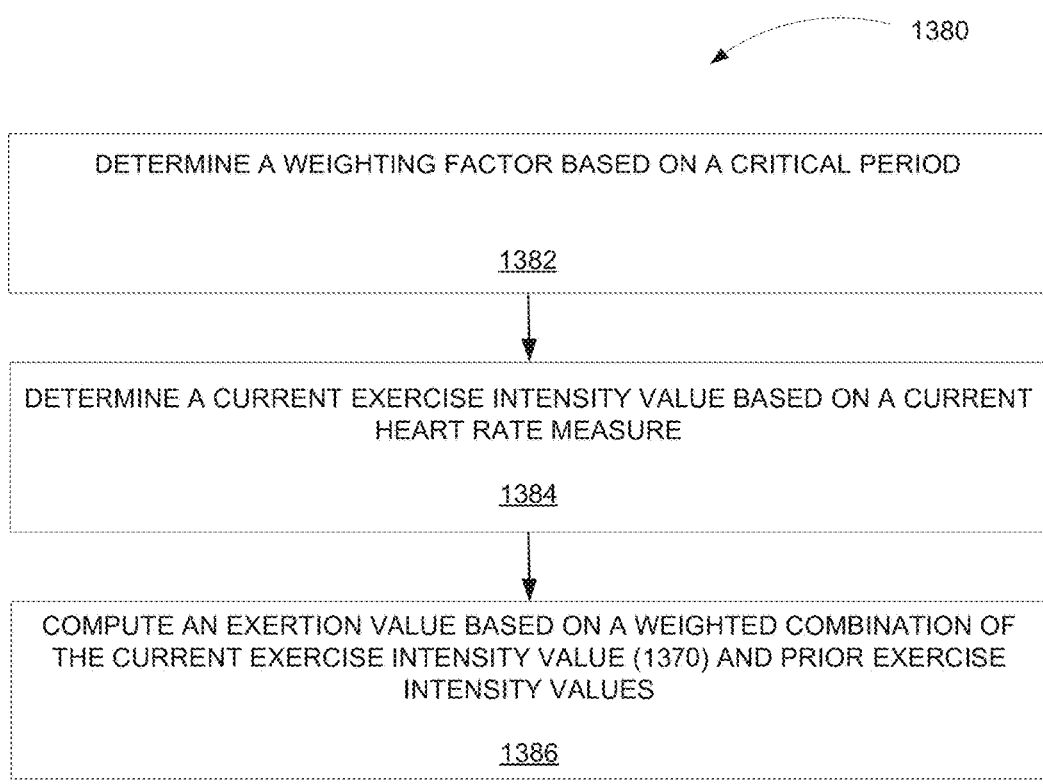
FIG. 13D is an example operational flow diagram illustrating various operations that may be performed to determine exertion in accordance with various embodiments of the present disclosure.
Figure 13E:
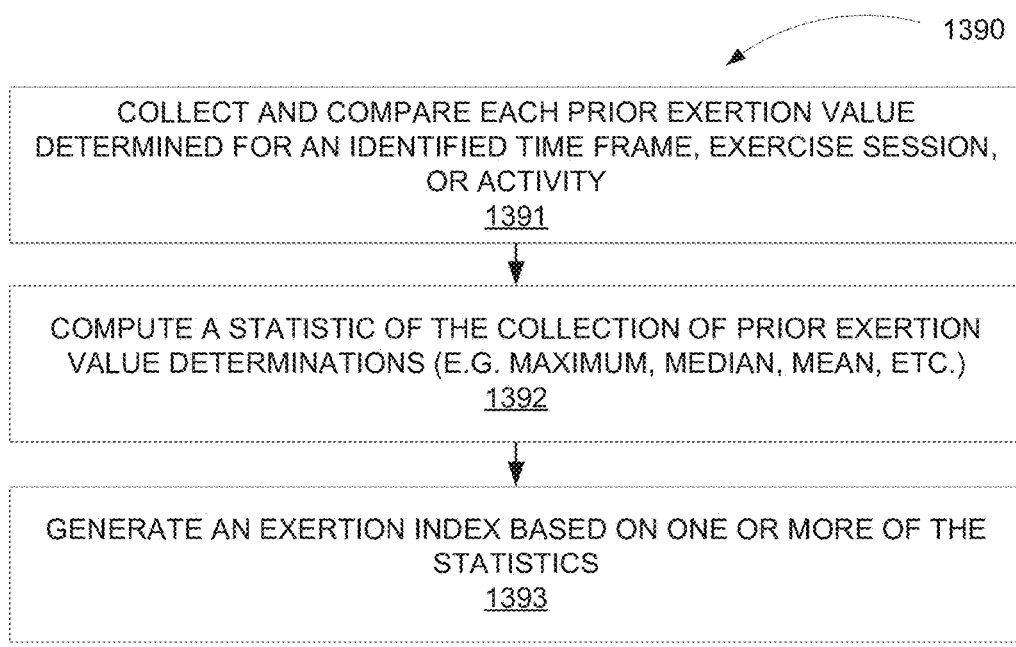
FIG. 13E is an example operational flow diagram illustrating various operations that may be performed to determine exertion in accordance with various embodiments of the present disclosure.
Figure 13F:
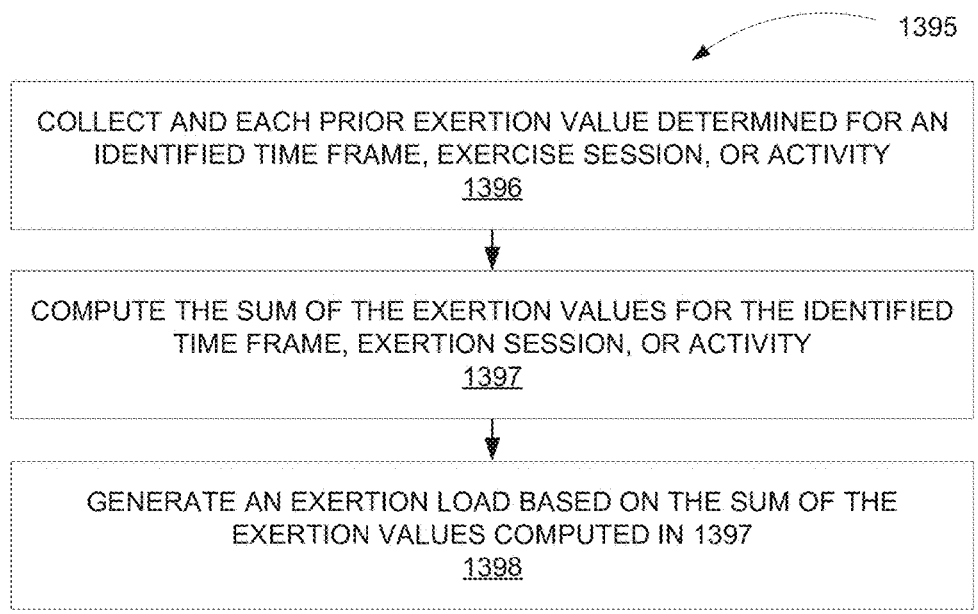
FIG. 13F is an example operational flow diagram illustrating various operations that may be performed to determine exertion in accordance with various embodiments of the present disclosure.

In particular, FIG. 13C provides an operation flow diagram including details of an exemplary implementation of operation 1360, FIG. 13D provides an operation flow diagram including details of an exemplary implementation of operation 1380, FIG. 13E provides an operation flow diagram including details of an exemplary implementation of operation 1390, and FIG. 13F provides an operation flow diagram including details of an exemplary implementation of operation 1395. These exemplary implementations will refer generally to method 1300 of FIG. 13B, and will be discussed together below. It should be noted, however, that some information (e.g. heart rate profile, exercise intensity model, critical period, etc.) and/or sub operations may be predetermined and preprogrammed in one or more of storage 1226 or 1216 before the systems, methods, and devices of the present disclosure are ever put to use by a user. However, regardless of whether one or more of the information/operations disclosed are identified and set prior to or during operation, any and all such variants are intended to fall within the scope of the present disclosure, as one of ordinary skill in the art will appreciate upon studying this disclosure.

Referring now to FIG. 13C, at operation 1362 a heart rate profile is identified for a particular user. The heart rate profile may include or be based, in part, upon a range or selection of one or more heart rate values detected by biosensor 1210; or, it may include or be based, in part, upon input from a user to wearable device 1202 or computing device 1208 (e.g. via a GUI displayed on computing device 1208). In other embodiments, the heart rate profile may be selected from one or more preset profiles that are based on information (e.g. human averages based on empirical data) preloaded into storage 1226 or 1216 to predict or approximate a profile for a user based on a user's inputted height, weight, activity levels, etc. In other embodiments, the heart rate profile may be created using a combination of information detected by biosensor 1210 and information provided by the user via computing device 1208. In still further embodiments, the heart rate profile may initially be provided by the user via computing device 1208, but then gradually modified as biosensor 1210 of wearable device 1202 learns more about the user's heart rate patterns from the detected biometric information. In still further embodiments, the heart rate profile may be preset to a standard profile based on a statistical analysis (e.g. average) of other humans. At operation 1364, an exercise intensity model is created based on the heart rate profile identified at operation 1362. Again, as indicated earlier, the exercise intensity model may similarly be predetermined and/or predefined and/or preselected in some embodiments of the present disclosure; or, it may be created and updated periodically using the most up-to-date biometric data detected by biosensor 1210 of wearable device 1202. In either case, taken together with FIGS. 13A-B, the exercise intensity model created at operation 1364 may be implemented at operation 1360 to determine exercise intensity values corresponding to heart rate measurements detected at operation 1350, which can then be used to determine exertion (e.g. exertion load and/or exertion index) at operation 1330 of method 1300.

Before moving on to a discussion of operation 1370 and 1380, example embodiments are now provided to illustrate various implementations of operation 1360, and related operations, in accordance with the technology disclosed herein.

For example, in some embodiments the heart rate profile identified for a particular user at operation 1362 is simply the user's maximum heart rate (or maximum heart rate achieved to date). This may be entered by the user via computing device 1208, detected by biosensor 1210 and/or motion sensor 1212, or the like. In such embodiments, the exercise intensity model may be created by generating data points that associate multiples or percentages (or other functions) of the user's maximum heart rate with values on a standardized scale representing exercise intensity (e.g. 1-10). Using the data points, an algebraic expression may be derived that represents a best fit for those data points (e.g. a regression line). The algebraic expression may be the exercise intensity model, and may be used at operation 1360 to map heart rate measures to exercise intensity values on the scale desired. For example, a user's heart rate profile may be given simply by their maximum heart rate (MHR) of 200 beats per minute (BPM). Data points may be generated based on one or more percentage(s) of the heart rate profile (e.g. a percentage of the maximum heart rate). For instance, in embodiments that employ an exercise intensity scale from 0-10, the data points may be generated by setting, for example, 50% of the MHR equal to 0, 75% of MHR=5, and 100% of MHR=10. In this example, the exercise intensity model may be given by a linear regression formula of the familiar form, y=m·x+b, and may be used to approximate/extrapolate exercise intensity values for any heart rate detected. In some embodiments, in this example, the exercise intensity model may be given by:

$$y(x)=0.1x-10 \quad (1)$$

where y is the exercise intensity value at heart rate measure of interest, x. In such an embodiment, the exercise intensity values determined at operation 1360 and maintained or stored at operation 1370 may be provided by the expression defining the exercise intensity model. For instance, in the example provided above, if a user's heart rate was detected once each second, and for a five second timeframe measured 120, 122, 124, 124 and 125, the exercise intensity values computed by the exercise intensity model and/or maintained at operation 1370 may be given as shown below in Table 1.0.

TABLE 1.0

| Time (t) | Heart rate at time (t) | Exercise Intensity Value (y) |
|---|---|---|
| 1 second ago | 125 BPM | 2.5 (e.g. y = 0.1 · 125 BPM − 10 = 2.5) |
| 2 seconds ago | 124 BPM | 2.4 |
| 3 seconds ago | 124 BPM | 2.4 |
| 4 seconds ago | 122 BPM | 2.2 |
| 5 seconds ago | 123 BPM | 2.3 |

In other embodiments, the exercise intensity model may be more complex, and may further account for a weighting of heart rate measures in accordance with empirical data and scientific information. For example, in some embodiments the exercise intensity model may be exponential in nature, and accord a greater difference in the exercise intensity value—and ultimately in the exertion determination—to an increase in heart rate on the higher end than for a similar increase in heart rate at the lower end. Indeed, as reflected in such examples, a user typically must exert more effort to increase their heart rate from 180 BPM to 185 BPM than is needed to increase their heart rate from 100 BPM to 105 BPM, even though the difference in both scenarios is the same, 5 BPM. Embodiments of the technology disclosed herein may account for these differences by employing, at operation 1360, an exercise intensity model that is weighted to account for the same. Such an approach may be employed to provide a more precise and personalized measure of exercise intensity—and ultimately exertion—and those of ordinary skill in the art will appreciate that various forms of empirical and scientific data known in the art may be implemented in accordance with the present disclosure without departing from the technology disclosed herein.

In an example of the above, in some such embodiments a more complex exercise intensity profile may be created using data points that reflect a weighted and/or nonlinear relationship between heart rate and exercise intensity—whether predetermined for a category of users (e.g. a statistical average), or empirically determined for a particular user—as noted above. The model may be more complex as noted above even though the user input may be simplistic. Indeed, even the more complex exercise intensity model may be based on one or more of (semi-) predetermined/preloaded/standardized information, and/or a single input from the user (e.g. the user's max heart rate serving as the heart rate profile). For example, a data point determination structure may be preloaded onto storage 1216 or 1226, or implemented in logic circuits of processor 1214 or 1224, in accordance with the following Table 2.0.

TABLE 2.0

| % of Maximum Heart Rate (% MHR) | Exercise Intensity Value (sometime referred to herein as a weighting value) |
|---|---|
| 0.5 (e.g. 50% of MHR) | 1 |
| 0.6 | 1.25 |
| 0.65 | 1.75 |
| 0.7 | 2.75 |
| 0.75 | 4 |
| 0.8 | 5.75 |
| 0.85 | 7.75 |
| 0.9 | 10 |

As shown in Table 2.0, the data points may include predetermined percentages of maximum heart rate corresponding to the appropriate exercise intensity values (scaled to reflect a desired weighting relationship). An algebraic expression may be derived based strictly on the percentages (instead of HR information directly), which may then be used to define the exercise intensity model. To use such a model, each heart rate detected at 1350 may simply be converted into a percentage of a user's maximum heart rate (previously inputted), which may then be used in connection with the exercise intensity expression/model, at operation 1360, to map the corresponding heart rate measures to exercise intensity values in a weighted manner, e.g., in accordance with the weighting reflected in the data points of Table 2.0. In sum, the exercise intensity model expression may approximate a weighted relationship between exercise intensity values and the particular user's heart rate measures. In some embodiments, an n-th order polynomial or exponential function may be used to approximate a best fit for the data points. Using the data in Table 2.0, the following exemplary 4th-order polynomial expression, or the like, may provide best fit for the data points.

$$y=(-266.52 \ldots)x^4+(746.74 \ldots)x^3-(704.13 \ldots)x^2+(276.21 \ldots)(746.74 \ldots)x-(37.75 \ldots) \quad (2)$$

where y is the exercise intensity value and x is the percentage of the user's max heart rate.

As noted, the examples provided in connection with Table 1.0 and Table 2.0 provide data points based on different quantities. In particular, the x in Table 1.0 is given by the actual heart rate measurements (in BPM), where the x in Table 2.0 represent multipliers (decimal values corresponding to percentages) of the MRH. However each corresponds to an exercise intensity value in a similar manner. One of ordinary skill in the art will appreciate that either of these approaches, along with various other quantities, multiples, metrics or other variables may be employed in connection with a user heart rate profile without departing from the scope of the technology disclosed herein. Indeed, in the examples above, either form may be converted into the other by a simple algebraic operation (e.g. [%]=[HR]/[MRH] or [HR]=[MRH]·[%]). For example, the information in Table 2.0 may be converted to reflect heart rate (HR) instead of the percent of max heart rate (% MHR) as shown below in Table 2.1.

TABLE 2.1

| % MRH (as a decimal) | Heart Rate (given in BPM) based on MRH of 200 BPM | Exercise Intensity Value |
|---|---|---|
| 0.5 | 100 BPM (e.g. 0.5 · 200 = 100) | 1 |
| 0.6 | 120 BPM | 1.25 |
| 0.65 | 130 BPM | 1.75 |
| 0.7 | 140 BPM | 2.75 |
| 0.75 | 150 BPM | 4 |
| 0.8 | 160 BPM | 5.75 |
| 0.85 | 170 BPM | 7.75 |
| 0.9 | 180 BPM | 10 |

*Based on a user maximum heart rate of 200 BPM

In either case, as well as in other embodiments in accordance with aspects of the presently disclosed technology, the data points and resultant expression derived from the data points reflect a weighted linear or weighted nonlinear relationship between heart rate and exercise intensity, or the like. This weighting, in accordance with embodiments of the present disclosure, may be observed by looking briefly at Tables 2.0 and 2.1, for example. As shown in Table 2.1, increasing one's heart rate 10 BPM from 170 BPM to 180 BPM corresponds to a difference of 2.25 on the exercise intensity scale, while increasing one's heart rate 10 BPM from 120 BPM to 130 BPM only corresponds to a difference of 0.5 on the exercise intensity scale. Similarly, in Table 2.1, increasing one's heart rate (viewed as a percentage of the MHR) from 85% of MHR to 90% of MHR corresponds to a difference of 2.25 on the exercise intensity scale, while increasing one's heart rate from 60% of the MHR to 65% of the MHR only corresponds to a difference of 0.5 on the exercise intensity scale. This reflects the weighting notion described above, and accords a greater difference in the exercise intensity value—and ultimately in the exertion determination—to an increase in heart rate on the higher end than for a similar increase in heart rate at the lower end.

In still further embodiments, the weighting reflected in the exercise intensity model/expression is at least partially defined by a range. For example the exercise intensity model employed in some embodiments may recognize the practical reality that most user's will not exceed an aerobic threshold for a sustained period, and thereby set a certain range of HRs or PMHRs to a particular exercise intensity value. For instance, all HRs detected that are greater than or equal to 90% MHR will be given a value of 10, while all HRs detected that are below 50% MHR will be given a value of zero. Accordingly, the exercise intensity profile may be given by a series of expressions reflecting the same. To extend the foregoing example, such expressions may include the following, or the like:

One of ordinary skill in the art will appreciate that variants of the foregoing expressions and/or series of expressions are intended to and will fall within the scope of the technology disclosed herein. As further depicted in FIG. 13C, at sub-operation 1366 operation 1360 determines an exercise intensity value for one or more detected heart rate measures using the exercise intensity model.

Moving now to a discussion of (sub-)operation 1380, FIG. 13D provides an operation flow diagram of exemplary embodiments of operation 1380 that may be implemented in accordance with operation 1330 of method 1300. Operation 1380 aggregates a set or subset of exercise intensity values determined at operation 1360, and aggregates them in a weighted/decaying manner based on their proximity in time to the present (i.e. the weight of earlier exercise intensities decaying with passing time) to compute an exertion value (also referred to herein as exertion level). As one of ordinary skill in the art will appreciate upon studying this disclosure, a user's exertion level and exercise intensity values are directly related, and a user's current exertion level may be determined by aggregating exercise intensity values over a critical period prior to the present. The critical period is typically a period of time near enough to the present within which it may be said that a given exercise intensity value (measured during that period) has at least some effect on the present exertion measure. For instance, exercise intensity from an activity performed last year will have little to no bearing a person's present exertion level, but exercise intensity from an activity performed just one minute ago will likely have a significant effect on the user's current exertion level. In other words, the effect of a singular exercise intensity measured during an activity performed in the past will have less and less an influence on the present as time progresses. The critical period may be predetermined and/or preprogrammed into one or more components of wearable device 1202, or computing device 1208, or in some embodiments the critical period may be entered by a user via computing device 1202. In still further embodiments, the critical period may be provided by and regularly updated via server 1206 based on empirical data, archived biometrics for the particular user, or the like.

At (sub-) operation 1384, the current (i.e. the most recent time measured) exercise intensity value is determined based on the current heart rate measure. In some embodiments, operation 1384 simply identifies the most recent exercise intensity value determined at 1360. In other embodiments it makes a separate determination. However, because a user's exertion during an exercise session or other activity cannot adequately be represented by the instantaneous exercise intensity value detected at the current moment during or at the end of an activity, the exertion measures provided by the systems and methods of the present disclosure are based on an aggregate measure of both the current and certain prior exercise intensity values. As discussed earlier, for example, the effort required for a weight-lifter to bench press their twentieth repetition is effected to some degree by the effort already expended during the first through nineteenth reps $$y(x) = \begin{cases} 0, & x < 0.5 \\ (-266.52 \ldots )x^4 + (746.74 \ldots )x^3 - (704.13 \ldots )x^2 + (276.21 \ldots )(746.74 \ldots )x - (37.75 \ldots ), & 0.5 \leq x \leq 0.9 \\ 10, & x > 0.9 \end{cases} \quad (3)$$

already performed. Accordingly, by way of example, the weight lifter's current exertion level not precise and/or accurate if it is based solely on the current exercise intensity value. However, it is more precisely and accurately represented when it reflects a measure of not only his current exercise intensity value during the twentieth rep, but also of his prior exercise intensity values (as an accumulated and weighted over a critical time period leading up to the twentieth rep, e.g. during the first through nineteenth reps).

Aggregating a user's current exercise intensity value with certain prior exercise intensity values can enable a more complete view of the user's actual exertion levels. Indeed, a scientific aggregation of these values provide a user with an intelligent way to evaluate their exertion during an activity, and make better fitness decisions to achieve their objectives. By way of example and not by of limitation, at operation 1380 some embodiments of the present technology compute the user's exertion using the following aggregation expressions, and/or variants thereof:

$$EV_t = EV_{t-1} + (I_t - EV_{t-1})*D \quad (4)$$

$$EV_0 = 0 \quad (5)$$

$$I_t = y(x_t) \quad (6)$$

$$x_t = HR_t * z \quad (7)$$

$$D = 1/p \quad (8)$$

where t is the amount of time that has elapsed since the exercise activity commenced (given in increments based on the interval between measurements, e.g., seconds); $EV_t$ is the Exertion Value as of the present moment (or most recent time segment measured), where the initial exertion value is set to zero, $EV_o=0$; $EV_{t-1}$ is the exertion value computed at the time segment just prior to the most recent time segment, e.g., if 35.4 seconds have passed, $EV_{t-1}$ would be the exertion value measured at the 34 second marker; $I_t$ is the exercise intensity value measured at the present moment, (or most recent time segment measured), e.g., if 35.4 seconds have passed, $I_t$ would be the exercise intensity value measured at the 35 second marker.

As indicated in equation (6), $I_t$ may be represented by an expression y(x) (e.g. a regression line represented by, for example, equations (1), (2) or (3) disclosed herein or variants thereof) that computes a normalized exercise intensity value scaled in a manner comprehensible to a user (e.g. scaled from 0-10, or 0-100, etc.). As further indicated, the normalized exercise intensity value for a given time segment may be based upon an input, x, that is directly related to user's detected heart rate during the time segment of interest, $HR_t$. As may be observed, variable z of equation (7) may be used to operate on the $HR_t$ value, to provide the $x_t$ measurement of interest as may be appropriate. In some embodiments (see discussion in connection with Table 1.0) the heart rate measure itself may be the desired $x_t$ for the expression $y(x_t)$ to produce the desired result. In such cases, z may simply be set to a value of 1. In other embodiments (see discussion in connection with Table 2.0), a percentage of the maximum heart rate may be required as the $x_t$ value for the expression $y(x_t)$ to produce the correct result. In such cases z may be set equal to 1/MHR such that $x_t = HR_t/MHR$ provides a percentage of the maximum heart rate as the input to the exercise intensity model/expression. One of ordinary skill in the art will recognize that variants of the foregoing may be implemented without departing from the scope of the technology disclosed herein.

Finally, D in equation (8) may be a constant, a variable or a function representing the decay component of the expression, which is based on the exercise intensity critical period, p, discussed above. As explained, the critical period may be thought of as the window of time up to the present during which the user's prior exercise intensity measures are expected to have a significant effect on their present exertion levels. Said differently, the critical period is the time period before which the user's prior exercise intensity measures are not expected to have a significant effect on the user's present exertion levels.

For instance, during a particular exercise session such as running, the runner's exercise intensity value from 5 minutes ago may have little to no bearing on their exertion level at the present, but the runner's exercise intensity value from 30 seconds ago will have an effect. In such an embodiment, the critical period may be determined to be 4 minutes (i.e. 240 seconds), for example. In other words, it may be determined that the current exertion measures for the user are most significantly affected by the user's exercise intensity during the last 4 minutes (e.g. 240 seconds). Thus, p=240 seconds, and so in the example above, D=1/240. Accordingly, D may apply an element of decay to the overall exertion value determination. Further, using the decay component, D, taken together with the foregoing expression, the systems, methods, and devices of the present disclosure may determine and provide a precise measure of exertion, $EV_t$, to a user based on a weighted accumulation of certain exercise intensity values and/or exertion values up to the present time t. In this manner, as discussed above, the exertion value computed at operation 1380 may attribute a lesser weight to earlier exercise intensity values as they are accumulated with each subsequent exertion value determination (which in some embodiments, occurs every second).

In some embodiments of the present technology, as indicated above, $x_t$ may be an actual heart rate measure (e.g. in BPM), and in other embodiments $x_t$ may be given as a percentage of a heart rate quantity (e.g. percentage of maximum heart rate, minimum heart rate, resting heart rate, etc.). In still further embodiments $x_t$ may be given as any other quantity based on the user's heart rate or heart rate profile. In any case, y(x) returns an exercise intensity value on a normalized or standardized scale (e.g. 1-10, 0-10, 1-100, 0-50, etc.). Although not required to implement the disclosed technology, one of ordinary skill in the art will recognize from the examples provided above that—since in some embodiments $EV_0$ is set to zero—the $EV_t$ values will reflect the same or similar scaling/normalization scheme used to compute exercise intensity values, $I_t$, at operation 1360. For example, the heart rate profile-to-exercise intensity scaling expression used in equation (6), in some embodiments, may ultimately dictate the scaling/normalization scheme reflected in the Exertion Values computed by equation (1). In this connection, it should be noted that y(x) may in some instances be a linear expression, an n-degree polynomial expression, an exponential expression, a non-linear expression, or otherwise.

As one of ordinary skill in the art will appreciate, the technology disclosed herein is not limited to the specific foregoing algebraic expressions and/or the foregoing examples. Instead, the foregoing expressions and examples are provided to illustrate by way of example how embodiments of the present technology may be implemented. Indeed, alternative expressions including various regression formulae may be employed without departing from the scope of the technology disclosed herein. Indeed, the notation used above and the formulae and/or examples may be modified and/or tailored to accommodate specific embodiments based on a variety of factors including a particular users capacity, activities, or otherwise. For example, y(x), p(t), z, etc. may be set to any variable or function that best approximates the exercise intensity value and/or exertion value for a particular category of user (e.g. children, professional athletes, elderly, etc.), an individual user, etc.

In any case, the exertion value at a given moment may be determined from a series of heart rates by converting or scaling those heart rate measurements to normalized and/or standardized exercise intensity values, then accumulating those exercise intensity values in a weighted manner over a select period of time. The exertion values determined and/or provided by the present disclosure may give user's a more granular, precise, and in some embodiments a real-time or near-real-time view of their exertion during/after an activity or exercise session.

What's more, as depicted at operation 1390 and operation 1395 in FIG. 13B, in some embodiments the systems, methods, and devices of the present technology provide a user with an Exertion Index and/or an Exertion Load based on the Exertion Values described above. FIGS. 13E and 13F provide operation flow diagrams including details of an exemplary implementation of operation 1390 and 1395 respectively.

Exertion Index is a score (e.g. 1-10) that describes the peak accumulated intensity a user achieved during a particular exercise session, activity, or time frame of interest. The Exertion Index is given by the maximum exertion value achieved during an exercise session, or up to a particular point in an exercise session if the session is not yet complete. As depicted in FIG. 13E, operation 1390 of method 1300 may in some embodiments, at sub operation 1391 collect and compare each prior exertion value determined over an identified time frame, exercise session, or other activity. The time frame is typically longer than the critical time period discussed herein. At sub operation 1392, operation 1390 may compute one or more statistics based on the collection of prior exertion value determinations from operation 1391, including at least the maximum exertion value measured over the identified time frame. At operation 1393, operation 1390 may generate an Exertion Index based on the maximum exertion value determined. In some embodiments, the Exertion Index is the maximum exertion value determined for a particular time frame, exercise session, or activity.

Exertion Load is a value that describes the overall (i.e. total) load/demand of the session based on both duration and accumulated exercise intensity. As depicted in FIG. 13F, exemplary operation 1395 of method 1300 may in some embodiments, at sub operation 1396, collect each prior exertion value determined over an identified time frame, exercise session, or other activity. At sub operation 1397, operation 1390 may compute the sum (i.e. total) of the collection of prior exertion values from operation 1396. At operation 1398, operation 1390 may generate an Exertion Load based on the sum computed in 1397. In some embodiments, the Exertion load is the sum computed in 1397. In other embodiments, the Exertion Load is given by a multiple or percentage of the sum computed in 1397. For example, the Exertion Load in some embodiments may be expressed by:

$$EL = x \cdot \sum_{0}^{t} EV_t$$

where EL is the Exertion Load, $EV_t$ is the Exertion Value at time t, t is the present time (or other time based on the interval or time frame desired), and x represents a variable or function that may be utilized to provide the Exertion Load on the scale of interest. For example, in some embodiments $$x = \frac{1}{100}$$

to scale down the Exertion Load determination by a factor of 100 for better user readability and comprehension. In some instances, x may be decreased as the total time frame, t, being assessed increases.

Finally, it should be noted that the systems, methods, and devices of the present technology may be used to provide a user with any one or more of an exercise intensity, exertion value (exertion level), exertion index, or exertion load in accordance with this disclosure. Any one or more of these may be displayed (and updated in real-time or near-real time) on a display, e.g., display 1030, display 1230, to enable a user to intelligently monitor, track, and meet their fitness objectives.

Figure 14A:
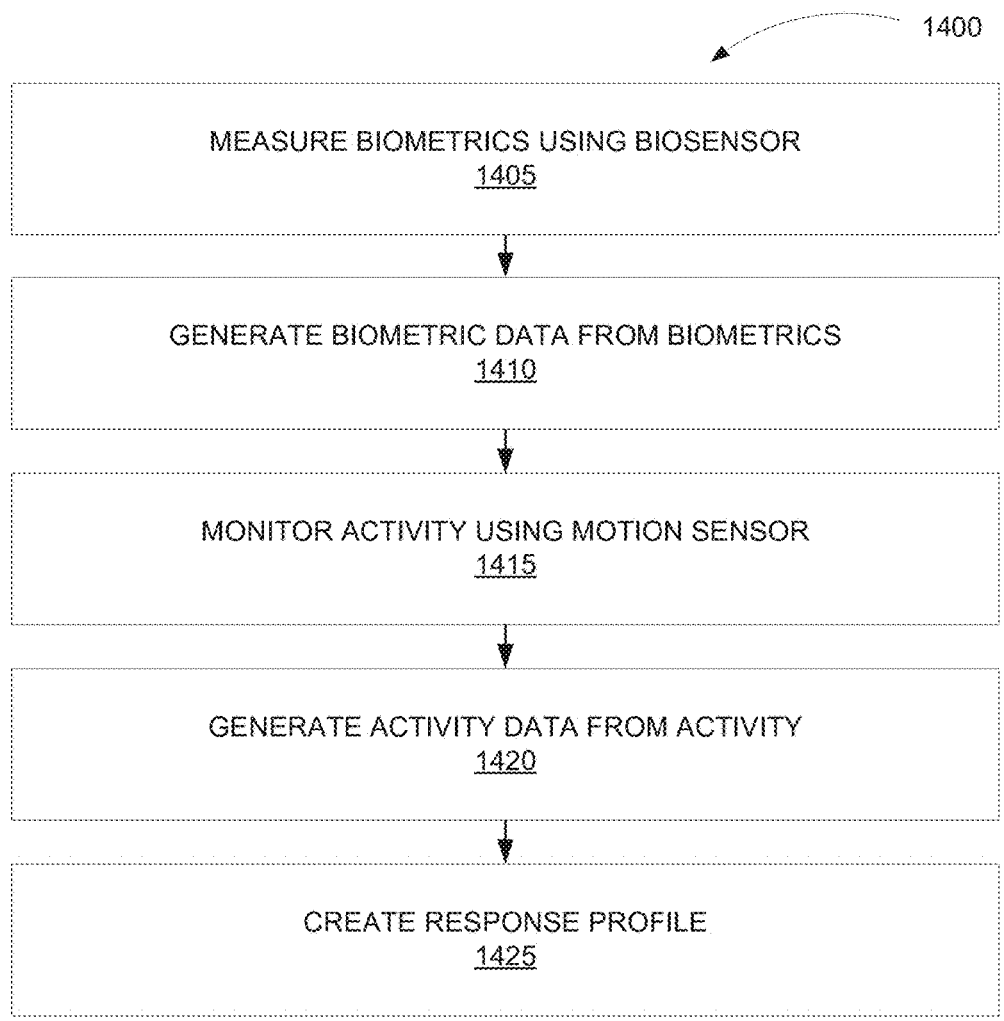
FIG. 14A is an example operational flow diagram illustrating various operations that may be performed to determine performance capacity in accordance with various embodiments of the present disclosure.

Referring now to FIG. 14A, at operation 1405, method 1400 entails measuring biometrics using a biosensor (e.g., biosensor 1210). The biosensor may be embedded in a wearable device (e.g., wearable device 1202). Measuring biometrics may include measuring a user's heart rate and calculating or estimating the user's HRV, for example. Biometrics may also include the user's temperature, blood pressure, and other physical characteristics of the user. Biometrics may be measured continuously or periodically. For example, in some cases, it may be desirable to determine the user's HRV on a daily basis. At operation 1410, method 1400 includes generating biometric data from the biometrics. This may involve circuits 1220 converting electrical signals from biosensor 1210 to a format that processor 1214 may process, store in storage 1216, and/or transmit by transmitter 1218. For example, biometric data may be generated from biometrics through analog-to-digital conversion, filtering of the biometrics, and/or encoding of the biometrics or data indicative thereof. Additionally, operation 1420 may also be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to generate biometric data from the biometrics monitored by biosensor 1210, including using circuits 1220.

Method 1400 also includes, at operation 1415, monitoring activity using a motion sensor (e.g., motion sensor 1212) embedded in the wearable device (e.g., wearable device 1202). Activity may include a user's movement, such as the type of movement (e.g., running, biking, swimming, etc.) and the intensity and duration thereof, the user's location and altitude, etc. Wearable device 1202 may include additional sensors, such as a temperature sensor, altimeter, hygrometer, and the like, to measure the user's environmental conditions. Alternatively, such conditions may be determined from external sources (e.g., weather conditions or location information available via data connection to the Internet).

At operation 1420, method 1400 includes generating activity data from the activity measured by the motion sensor. In a fashion similar to operation 1410, this may entail circuits 1220 converting electrical signals from motion sensor 1212 to a format that processor 1214 may process, store in storage 1216, and/or transmit by transmitter 1218. Operation 1420 may also be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to generate activity data from the activity measured by motion sensor 1212, including using circuits 1220.

At operation 1425, method 1400 involves creating a performance response profile. The response profile generally indicates how a user is likely to respond to a given training load or other activity. Often, a user's response to a given training load will depend on many factors, including, for example, how fatigued the user is, or the user's relative amounts of activity and rest over a recent time period, fitness level, diet, environmental conditions, stress level, amount of sleep, mood, and so on. The user's HRV may act as a robust indicator of the user's capacity to exercise, need for rest, overall energy, stress levels, and other health/physical conditions. The user's HRV may be determined using biosensors, as described herein. The HRV, however, is not always available for the current day (e.g., if the user fails to enable a measurement by not wearing the wearable device, etc.). Another potentially useful indicator of the user's performance capacity is the use's recent activity levels, which may generally be referred to herein as fatigue. As mentioned above, the user's movement and hence activity may be monitored using a motion sensor and in some cases, additional hardware as described herein.

In light of the usefulness of both fatigue and HRV, and the occurrence that one or the other, or both, may in some cases not be available, the response profile is based on one or more of an HRV score, a fatigue score, a predicted HRV score, and a predicted fatigue score. As will be described in further detail, the HRV score is based on biometrics (including the user's HRV, in some cases) but is personalized to the user. Likewise, the fatigue score is based on the user's fatigue (e.g., past activity levels) but is personalized to the user. The fatigue score may be used to generate a fatigue model for the user, and the HRV score can be used to create an HRV model for the user. The fatigue model may then be used in some embodiments to generate a predicted fatigue score absent recent fatigue data, and the predicted fatigue score is based on one or more of the biometric data and the activity data. Likewise, the HRV model may be used to generate a predicted HRV score absent recent HRV measurements, and the predicted HRV score is based on one or more of the biometric data and the activity data. This will be described in detail with reference to FIGS. 14B and 14C.

Figure 14B:
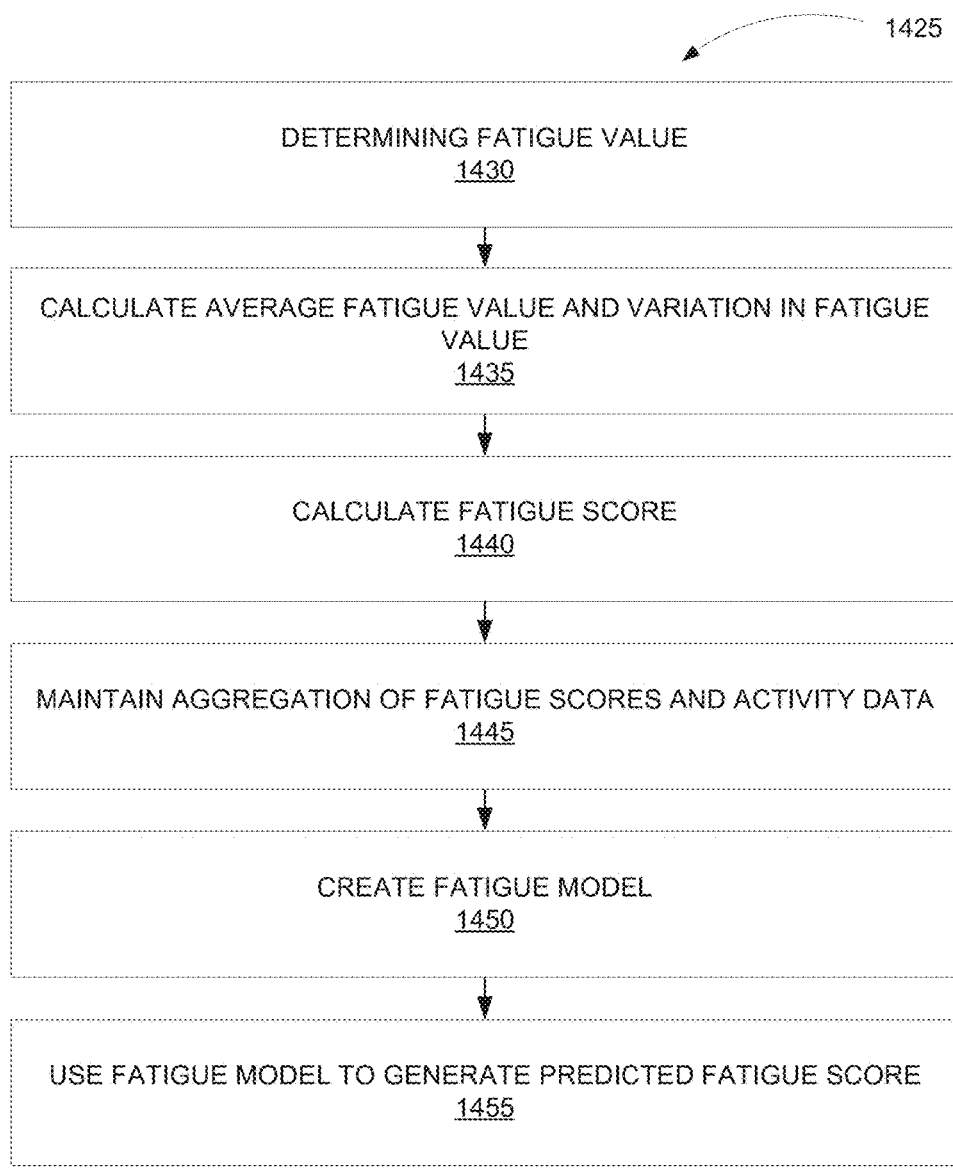
FIG. 14B is an example operational flow diagram illustrating various operations that may be performed to determine performance capacity in accordance with various embodiments of the present disclosure.

Turning now to FIG. 14B, an operation flow diagram of embodiments of method 1400 and in particular of operation 1425 is provided. At operation 1430, creating the response profile (operation 1425) includes determining a fatigue value. The fatigue value is determined based on the combination of a previous fatigue value with a first difference calculated by a processor (e.g., processor 1214 or 1224). The first difference is between the previous activity value and the previous fatigue value. Further, the first difference is scaled by a fatigue decay. Equation (9), below, illustrates an example of how the fatigue value may be determined.

$$\text{fatigue}(n) = \text{fatigue}(n-m) + \frac{\text{activity value}(n-k) - \text{fatigue}(n-m)}{\text{fatigue decay}} \quad (9)$$

In equation (9), fatigue (n) represents the fatigue value at a present time/day, where n=0, while fatigue (n–m) represents the previous fatigue value from m days or units of time ago. For example, if m=1, the previous fatigue value may represent yesterday's fatigue value. Likewise, activity value (n–k) represents the previous activity value, where k=1 may correspond to yesterday's activity value. The activity value may represent a numerical count (e.g. points) based on the user's activity, including activity type, duration, intensity, and so on. If the previous fatigue value is not available, the user's average activity level may be used in equation (9) in lieu of the previous fatigue value. Fatigue decay is typically represented as a constant (e.g., 7), but may be selected from any range of numbers. In other instances, fatigue decay may be particular to the user, for example, by being derived via the HRV model that will be described herein. In short, in such instances, the fatigue decay may be based on the user's actual response to/recovery from various types of activity. Operation 1430 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to determine the fatigue value, including by calculating the first difference, scaling the first difference by the fatigue value, and combining the scaled first difference with the previous fatigue value.

In one embodiment, a fitness value is determined. The fitness value may be determined based on the combination of a previous fitness value with a difference calculated by a processor (e.g., processor 1214 or 1224). With respect to fitness value, in example implementations, the difference is between the previous activity value and the previous fitness value. Further, the difference is scaled by a fitness decay. Equation (10), below, illustrates an example of how the fitness value may be determined.

$$\text{fitness}(n) = \text{fitness}(n-m) + \frac{\text{activity value}(n-k) - \text{fitness}(n-m)}{\text{fitness decay}} \quad (10)$$

In equation (10), fitness (n) represents the fitness value at a present time/day, where n=0, while fitness (n–m) represents the previous fitness value from m days or units of time ago. For example, if m=1, the previous fitness value may represent yesterday's fitness value. Likewise, activity value (n–k) represents the previous activity value, where k=1 may correspond to yesterday's activity value. The activity value may represent a numerical count (e.g. points) based on the user's activity, including activity type, duration, intensity, and so on. If the previous fitness value is not available, the user's average activity level may be used in equation (10) in lieu of the previous fitness value. Fitness decay is typically represented as a constant (e.g., 42), but may be selected from any range of numbers. In other instances, fitness decay may be particular to the user, for example, by being derived from characteristics of how the user recovers over time, e.g., via the HRV model that will be described herein. In short, in such instances, the fitness decay may be based on the user's actual response to/recovery from various types of activity. Operation 1430 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to determine the fitness value, including by calculating the difference, scaling the difference by the fitness value, and combining the scaled difference with the previous fitness value.

At operation 1435, creating the response profile includes calculating an average fatigue value and a variation in the fatigue value. This calculation is based on a set of the fatigue values previous determined. The average fatigue value may be the mean, median, or mode of previously determined fatigue values (e.g., determined in previous time periods using operation 1430). In some cases, the average fatigue value includes the fatigue value determined for the present day. The variation in the fatigue value may in some cases be the standard deviation of the previously determined fatigue values determined in previous time periods, e.g., fatigue levels determined for past days. In some cases, the variation in the fatigue value includes the fatigue value determined for the present day. Operation 1435 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the average fatigue value and the fatigue value variation.

Continuing the example, operation 1425 of method 1400 may include operation 1440, calculating the fatigue score based on a second difference. The second difference is between the average fatigue value (e.g., calculated at operation 1435) and the fatigue value (e.g., determined at operation 1430). The second difference is scaled by the variation in the fatigue value (e.g., calculated at operation 1435). Equation (11), below, illustrates an example of how the fatigue score may be calculated.

$$\text{fatigue score} = \frac{1}{\sigma} * \left\{ \left( \frac{1}{k} * \sum_{i=0}^{k} \text{fatigue value}(n-i) \right) - \text{fatigue}(n) \right\}$$

In equation (11), fatigue value (n−i) represents the previous fatigue value from i days or units of time ago. Thus, the summation is taken over k number of days or units of time for which previous fatigue values have been determined. The summation is then divided by k to obtain the average previous fatigue value. The starting value of i, as well as the value of k, may be changed to shift the time period over which the fatigue value is averaged. The fatigue value variation is represented in equation (11) by σ. In this manner, the fatigue score is normalized for the user, and may thus represent statistically how the user's fatigue value stacks up against the user's typical or baseline fatigue values measured over time. In this regard, the fatigue score may be normalized so as to range an upper bound to a lower bound. The upper and lower bounds may be set to be two standard deviations from the mean fatigue score. Additionally, the upper and lower bounds may be capped respectively at 100 and 0. Of course, any range of numbers may be used, depending on the circumstance. In other scenarios, the fatigue score may be scaled by an additional constant (e.g., 25, or a constant ranging from 0 to 100 or any number), and may be added to an offset (e.g., 50, or an offset ranging from 0 to 100 or any number). Operation 1440 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the various values in equation (11) and thus the fatigue score.

Referring again to FIG. 14B, method 1400, and specifically operation 1425 thereof, in some example implementations, includes operation 1445. Operation 1445 involves maintaining, for a previous measuring period, an aggregation of the calculated fatigue scores (e.g., from operation 1440) and an aggregation of the activity data. The aggregation of the calculated fatigue scores may include fatigue scores calculated for each of a series of days that occurred during the previous measuring period. Likewise, the activity data may also correspond to activity monitored during the series of days occurring during the past measuring period. The past measuring period may be of programmable length, and may be defined in time units other than days (e.g., months, weeks, hours, etc.). The aggregation of calculated fatigue scores and the activity data may be maintained in storage 1216 and/or storage 1226, or in cloud storage (e.g., in server 1206). Operation 1445 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to maintain the aggregation of the calculated fatigue scores and activity data.

According to various embodiments, at operation 1450, operation 1425 includes creating a fatigue model. The fatigue model is derived from a correlation of the aggregation of the calculated fatigue scores with the aggregation of the activity data. In example implementations, the fatigue model may be represented as a distribution or table of fatigue scores corresponding to ranges of activity values or other input parameters. The fatigue model may be presented to the user (e.g., via display 1030 of computing device 120). In such cases, the user may be able to tweak the model, adapt the weighting of parameters therein, and so on. Essentially, the fatigue model may be created by mapping the fatigue scores to corresponding activity data to determine the relationship between the user's activity level and the user's fatigue scores. In this manner, provided with an expected level of activity (or activity value), the fatigue model may be used to generate a predicted fatigue score, based on the correlation of previous fatigue scores to previous activity levels. This is represented at operation 1455 in FIG. 14B. The predicted fatigue score may be used to gauge what a user's response will be to a particular training load, in terms of fatigue. The fatigue model may be presented to the user (e.g., via display 1030 of computing device 120). In such cases, the user may be able to tweak the model, adapt the weighting of parameters therein, and so on. Operation 1455 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to create the fatigue model and use the fatigue model to generate a predicted fatigue score.

Figure 14C:
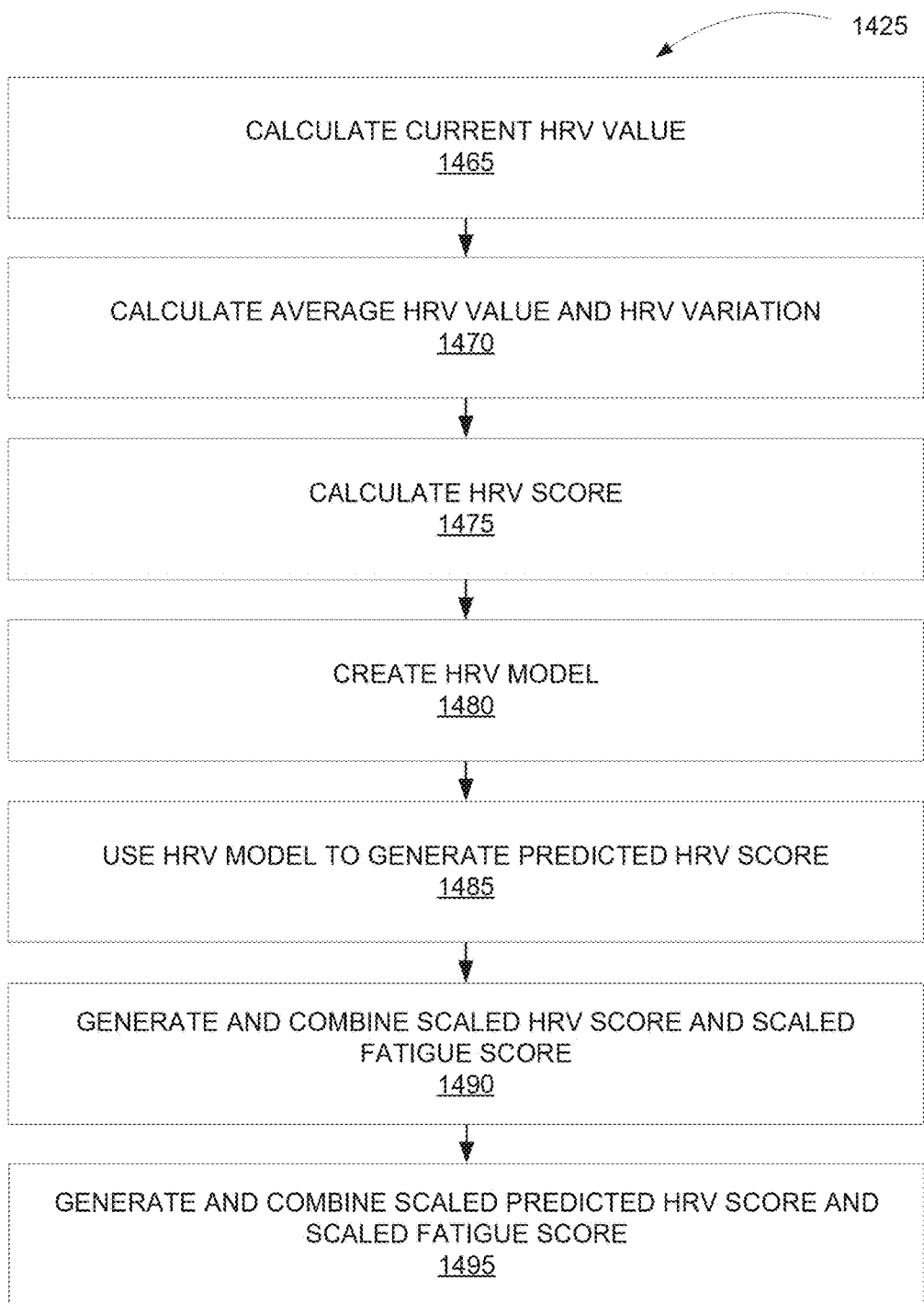
FIG. 14C is an example operational flow diagram illustrating various operations that may be performed to determine performance capacity in accordance with various embodiments of the present disclosure.

FIG. 14C provides an operational flow diagram for embodiments of method 1400 and in particular in connection with operation 1425. The operations shown in FIG. 14C relate to calculating the user's HRV and an HRV score that is personalized for the user, and creating an HRV model that correlates various environmental/external conditions, such as the user's sleep, activity, rest, geographic information, and stress levels, with the user's HRV. The HRV model may be used to predict the user's HRV score in instances where the user's HRV information is not available, or in instances in which the user wishes to get a sense for the user's response to a particular training load or set of conditions.

At operation 1465, creating the response profile (operation 1425) includes calculating a current HRV value from the biometric data. The biometric data may be related to the user's heart activity, e.g., electro-cardio signals from the user's heart, and may be used to calculate HRV, as described above with reference to FIGS. 2 and 3. Operation 1465 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the HRV value from the biometric data.

At operation 1470, creating the response profile includes calculating an average HRV value and an HRV variation. This may be done in a fashion similar to operation 1435. Here, the calculation is based on an a set of HRV values previously calculated based on the biometric data. The average HRV value may be the mean, median, or mode of previously calculated HRV values (e.g., the current HRV values calculated for previous time periods using operation 1465). In some cases, the average HRV value includes the HRV value determined for the present day. The variation in the HRV value, or the HRV variation, may in some cases be the standard deviation of the previously calculated HRV values determined in previous time periods, e.g., HRV values determined for past days. In some cases, the HRV variation includes the HRV value determined for the present day. Operation 1470 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the average HRV value and to calculate the variation in the HRV value.

As illustrated in FIG. 14C, operation 1425 may also include calculating an HRV score, at operation 1475. The HRV score is calculated based on a difference between the average HRV value (e.g., calculated at operation 1470) and the current HRV value (e.g., calculated at operation 1465). Moreover, the difference is scaled by the HRV variation (e.g., calculated at operation 1470). Equation (12), below, illustrates an example of how the HRV score may be calculated.

$$HRVscore = \frac{1}{\sigma} * \left\{ \left( \frac{1}{k} * \sum_{i=0}^{k} HRVvalue(n-i) \right) - HRV(n) \right\} \quad (12)$$

In equation (12), HRV value (n−i) represents a previously calculated HRV value from i days or units of time ago. Thus, the summation is taken over k number of days or units of time for which previous fatigue values have been determined. The summation is then divided by k to obtain the average of the previously calculated HRV values. The starting value of i, as well as the value of k, may be changed to shift the time period over which the HRV value is averaged. The HRV variation is represented in equation (12) by σ. In this manner, the HRV score is normalized for the user, and may thus represent statistically how the user's current HRV value stacks up against the user's typical or baseline HRV values measured over time. In this regard, the HRV score may be normalized so as to range between an upper bound to a lower bound. The upper and lower bounds may be set to be two standard deviations from the mean HRV score. Additionally, the upper and lower bounds may be capped respectively at 100 and 0. Of course, any range of numbers may be used, depending on the circumstance. In other scenarios, the HRV score may be scaled by an additional constants, and may be added to an offset. Operation 1475 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to calculate the difference and scale the same by the HRV variation.

According to various embodiments, at operation 1480, operation 1425 includes creating an HRV model. The HRV model is based on a correlation of calculated HRV scores, which may be aggregated over time and stored with the activity data, which likewise may be aggregated and stored. Essentially, the HRV model may be created by mapping the HRV scores to corresponding activity data to determine the relationship between the user's activity level and the user's fatigue scores. In some cases, the HRV score may further be mapped to aggregated biometric data other than HRV (e.g., the user's temperature and so on), or to aggregated environmental data indicative of environmental conditions described above. In this manner, provided with an expected level of activity (or activity value) or expected environmental conditions or biometrics, the HRV model may be used to generate a predicted HRV score. This is represented at operation 1485 in FIG. 14C.

The HRV model may be used to gauge what a user's response will be to a particular training load and/or environmental conditions and/or biometrics, in terms of HRV. In example implementations, the HRV model may be represented as a distribution or table of HRV scores corresponding to ranges of activity values or other input parameters (e.g., biometrics or environmental conditions). The HRV model may be presented to the user (e.g., via display 1030 of computing device 120). In such cases, the user may be able to tweak the model, adapt the weighting of parameters therein, and so on. Operations 1480 and 1485 may be performed by processor 1214 or 1224. For example, storage 1216 or 1226 may include a non-transitory computer readable medium operatively coupled to processor 1214 or 1224 and storing instructions thereon that, when executed, cause processor 1214 or 1224 to create the HRV model and use the HRV model to generate the predicted HRV score based on the activity data.

Referring again to FIG. 14C, embodiments of operation 1425 include, at operation 1490, generating a scaled HRV score from the HRV score, and generating a scaled fatigue score from the fatigue score. The HRV score and the fatigue score may be scaled by respective scaling factors. For example, the scaling factors may be fractions less than 1, thus decreasing the value of the HRV score or fatigue score, or may be greater than 1 in order to increase the value of the scores. In other cases, the scaling factors may be negative. Referring again to operation 1490, the scaled HRV score and the scaled fatigue score may be combined. As shown below in equation (13), the respective scaling factors may be used to determine the mix that the HRV score and the fatigue score contribute to the combination. The combination, in one instance, may represent the response profile.

$$\text{response profile} = \alpha * \text{fatigue score} + \beta * \text{HRV score} \quad (13)$$

In equation (13), α corresponds to the scaling factor for the fatigue score, and β corresponds to the scaling factor for the HRV score. In some cases, α may be set to zero, such that only the HRV score contributes to the response profile. Typically, β will be set to 1 in such cases. In other cases, β may be set to zero, such that only the fatigue score contributes to the response profile. Typically, α will be set to 1 in such cases. In one embodiment α and β are both set to 0.5, such that the fatigue score and the HRV score contribute equally to the response profile. In another embodiment, β is set to 0.75 and α is set to 0.25, such that the HRV score contributes more to the response profile. This weighting may emphasize the user's holistic response to all environmental and other inputs besides, as captured by the user's tailored HRV score, as opposed to emphasizing contribution from the user's activity, as captured by the fatigue score.

At operation 1495, operation 1425 of method 1400 includes generating a scaled predicted HRV score from the predicted HRV score, and generating a scaled fatigue score from the fatigue score. The scaled predicted HRV score may be scaled by a scaling factor, in a fashion similar to that described above in connection with operation 1490. Referring again to operation 1495, the scaled predicted HRV score and the scaled fatigue score may be combined. As shown below in equation (14), the respective scaling factors may be used to determine the mix that the predicted HRV score and the fatigue score contribute to the combination. The combination, in one instance, may represent the response profile.

$$\text{response profile}=\alpha*\text{fatigue score}+\gamma*\text{predicted HRV score} \quad (14)$$

In equation (14), α corresponds to the scaling factor for the fatigue score, and γ corresponds to the scaling factor for the predicted HRV score. In some cases, α may be set to zero, such that only the predicted HRV score contributes to the response profile. Typically, γ will be set to 1 in such cases. In other cases, γ may be set to zero, such that only the fatigue score contributes to the response profile. Typically, α will be set to 1 in such cases. For example, such cases may occur where it is desired for the response profile to focus only on the user's activity and to diminish the user's response to other factors such as, by way of illustration, the user's physical response to activity, which may generally be accounted for using HRV. Additionally, γ may be set to zero if there is simply no HRV information available (e.g., if the user has never measured HRV). In one embodiment α and γ are both set to 0.5, such that the fatigue score and the predicted HRV score contribute equally to the response profile. In another embodiments, α and γ may be varied or programmed, such that the predicted HRV score or the fatigue score contributes more to the response profile. The predicted fatigue score may be substituted in equations (13) or (14) and scaled and combined with either the HRV score or the predicted HRV score as described above with regard to the fatigue score.

An accurate and personalized response profile of the above-described nature may allow the user to make informed decisions regarding the user's training load and/or lifestyle, thus achieving maximum performance and balance. Referring again to FIG. 14A, and as indicated above, the response profile created at operation 1425 may generally indicate how a user is likely to respond to a given training load or other activity or set of conditions. This indication, in some embodiments, represents the user's performance capacity (e.g. the user's capacity to undertake a given training load, perform a given activity, etc.). Such an indication may be provided to a user in one or more of an audio, visual, numerical, descriptive, or graphical representation (e.g. via display 1230 of computing device 1208, etc.). For instance, if the indication is given on a scale from 0 to 100, and for a given training load or other activity the response profile indicates a 75 on this scale, this indication may be provided to a user in a bar graph, a scale, a numeral, a digital gauge, a textual description, or the like (e.g. a bar graph depicted as being filled ¾ of the way). In some such embodiments, a 0 on the response profile scale may represent little to no capacity to perform the activity (e.g. the user's biometrics reflect that they have been working for 24 hours straight with no sleep, and they need rest immediately), and a 100 on the response profile scale may represent full capacity (e.g. the user's biometrics reflect that they are well-rested and otherwise ready for activity). Of course, any scale may be implemented without departing from the scope of the present disclosure, as indicated previously. Thus, the response profile created and provided by the systems, methods, and devices of the present disclosure enable a user to intelligently assess their capacity to perform an activity.

Moreover, each of the measurements, operations, computations, etc. described in connection with the exertion measures detailed earlier (with reference to FIGS. 13A-13F) may be performed in conjunction/parallel with the measurements, operations, computations, etc. described in connection with the response profile indications/measures detailed above (with reference to FIGS. 14A-14C). In various embodiments, one or more of the response profile measures/indication and the exertion measures/indications are used to further provide a user with an exertion recommendation for an impending/anticipated exercise session. The details of some such embodiments are provided in connection with FIGS. 15A-15B below.

It is noted here that the operations/methods described below in connection with FIGS. 15A-15B may be informed by and build upon the operations/methods discussed in connection with FIGS. 13A-14C. It is further noted that one or more operations and/or sub-operations discussed in connection with method 1300, 1400 and 1500 may inform, be used in place of, or be use in parallel with one or more of the other operations of these methods. For instance, operation 1305 and 1405 may in some embodiments be the same operation, and may performed using the same instructions stored on the same non-transitory computer readable medium operatively coupled to one or more of the same processors 1214 or 1224, and the biometric measured therefrom may inform both operation 1320 and 1410 of methods 1300 and 1400, which may further inform and provide the data forming the basis for method 1500 to provide an exertion recommendation. One of ordinary skill in the art will appreciate that the operations and sub-operations of methods 1300, 1400, and 1500 may be deduplicated in many such ways (often to reduce processing load, power consumption, etc.) without departing from the spirit and scope of the present disclosure.

It is further noted here that the operations and sub-operations of method 1500 may be carried out, in some cases, by one or more of the components/elements/devices/modules of communication environment 100, earphones 110, wristband 105, computing device 120, tracking application 1015, and/or system 1200—described above with reference to FIGS. 1-12B—as well as sub-components/elements/devices/modules depicted therein or described with respect thereto. It will be appreciated by one of skill in the art that aspects and features described above in connection with (sub-) components/elements/devices/modules, including variations thereof, may be applied to the various operations described in connection with method 1500. It will further be appreciated by one of skill in the art, consistent with the foregoing disclosures of methods 1300 and 1400, that use of the terms operation and sub-operation with respect to method 1500 may in some instances be used interchangeably.

Figure 15A:
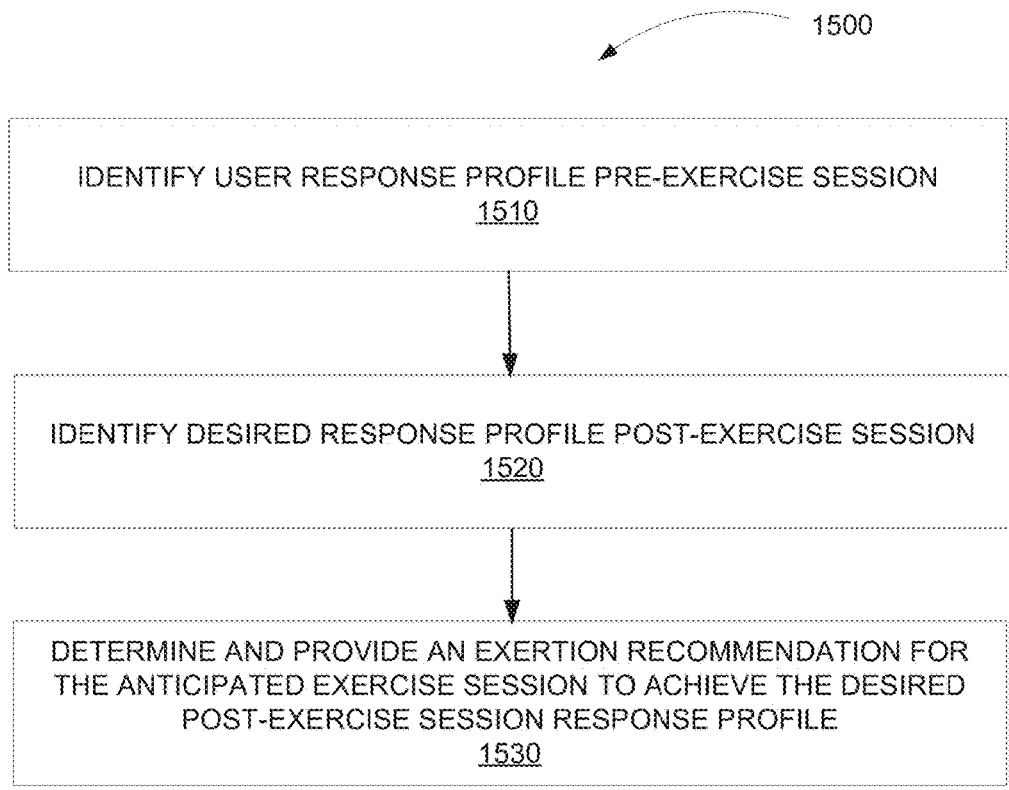
FIG. 15A is an example operational flow diagram illustrating various operations that may be performed to determine an exertion recommendation in accordance with various embodiments of the present disclosure.
Figure 15B:
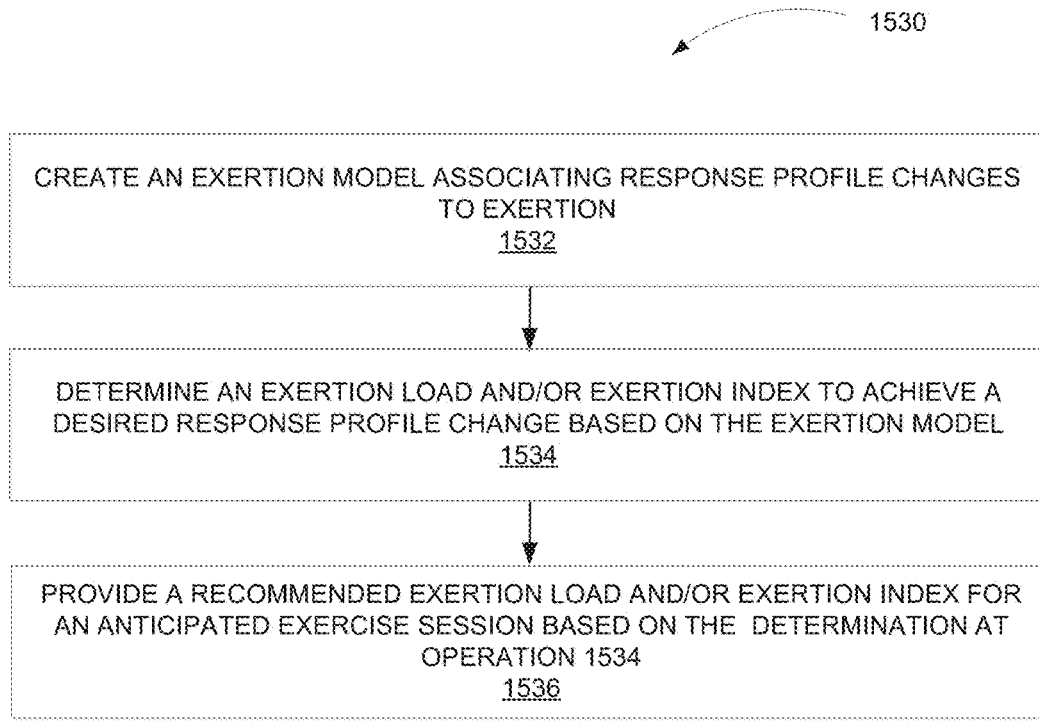
FIG. 15B is an example operational flow diagram illustrating various operations that may be performed to determine an exertion recommendation in accordance with various embodiments of the present disclosure.

FIGS. 15A-15B illustrate flow charts depicting various operations of an exemplary computer-implemented method 1500 and accompanying embodiments for determining and providing an exertion recommendation in accordance with the present disclosure. In particular, method 1500 entails determining and providing an exertion recommendation for an anticipated exercise session, activity, or time period of interest. Although the exemplary figures and description that follow are provided and described with respect to an exertion recommendation for an exercise session in particular, these are non-limiting examples provided for clarity, and it should be understood that the technology of the present disclosure also extends to exertion recommendation in connection with other activities and/or time periods of interest to the user.

The exertion recommendations provided by the systems, methods and devices of the present disclosure may include one or more of a recommended exertion load, a recommended exertion index, or other intelligent exertion recommendation reflecting a combination of both.

Referring now to FIG. 15A, at operation 1510, method 1500 entails identifying the user's current (or most recent) response profile (e.g. before an exercise session). At operation 1520, method 1500 entails identifying what the user would like their response profile to be at some point in the future (e.g. after the exercise session). At operation 1530, method 1500 calculates/determines/provides an exertion recommendation for a user's upcoming exercise session, that, if achieved, would allow the user to realize their desired post-exercise session response profile (e.g. identified at operation 1520). Various embodiments of method 1500 are further detailed below.

At operation 1510, method 1500 identifies the user's current response profile (e.g. before an exercise session). In some embodiments, the identified current response profile is obtained or informed by one or more outputs/operations described above in connection with method 1400. For example, in some embodiments of the present technology, the pre-exercise session response profile identified at operation 1510 is the most recent response profile (or an indication thereof)—as computed prior to commencing an exercise session—created at operation 1425 of method 1400.

At operation 1520, method 1500 identifies a desired post-exercise session response profile (or an indication thereof). This may occur in a variety of ways, including but not limited to prompting the user to input such information (e.g. a number on a scale) via a GUI on a display (e.g. display 1030, 1230, etc.); estimating such information based on a historical archive of the user's preferred post-exercise response profile (or a pattern detected therefrom); estimating such information based on other information collected from other modules/components/applications of a computing device 1208 (e.g. activities scheduled in a user's electronic calendar in computing device); or the like. In embodiments that entail making an estimate of a user's desired post-exercise response profile, one of ordinary skill in the art will appreciate that any one or more of the data/information/computations/determinations/operation outputs may be stored on one or more of the storage/memory components (e.g., memory 840, memory 855, storage 1010, storage 1226, or the like), and further used to make such an estimate. One of ordinary skill in the art will further recognize that an archive of such data may be maintained in such storage/memory components, the archive being a collection of any one or more of the data/information/computation/determinations provided by any one or more of the methods/operations/sub-operations disclosed herein. Data from the archive (including patterns detected therefrom) may be used, as indicated above, at operation 1520 to estimate a desired response profile for a user.

For example, operation 1520 may estimate a user's desired post-exercise session response profile based on the average/median of the user's previously inputted desired post-exercise session response profiles (over a week, a month, year, etc.). In another example, operation 1520 may identify a desirable post-exercise response profile based on a combination of the foregoing (e.g. archival patterns detected, direct input from a user), as well as information gleaned from other sources (e.g. sensors, applications, etc.) accessible to computing device 1208. For example, the desired post-exercise response profile identified may be based, in whole or in part, on information obtained from an electronic clock, thermometer, altimeter, an electronic calendar, etc. accessible to the systems and methods of the present disclosure via one or more of computing device 120, wearable device 1202, server 1206, or the like.

For instance, the user's current response profile at 9:00 am may indicate a numeric representation of 95 on a scale from 0 to 100, indicating, for example, that the user is fairly well-rested and prepared for an intense exercise session (i.e. involving high levels of exertion) anticipated between 9:15 am and 10:15 am. The user may have previously inputted the same desired post-exercise session profile (e.g. 55 for example) before the same or similar exercise session for five prior days, so operation 1520 may automatically predict and set the desired post-exercise session response profile at the same level (e.g. at 55) for the instant exercise session on that basis. In some embodiments, such a prediction may be subject to the user's acceptance and or modification via GUI of display 1030, display 1230, or the like.

In another scenario, to expand the example, the user's calendar may inform method 1500 at operation 1520 that the user is participating in a scheduled boxing match that evening at 5:00 pm (which may be unusual based on the user's typical daily pattern). Accordingly, operation 1520 may adjust the post-exercise session response profile to a higher level (e.g. 75 instead of 55) to help/suggest to the user to preserve more energy for his/her upcoming boxing match. Again, such a suggestion/prediction may be subject to the user's acceptance and or modification via GUI of display 1030, display 1230, or the like. One of ordinary skill in the art will appreciate that these examples are merely exemplary for purposes of discussion, and that variants thereof may be used—as indicated above—without departing form the scope of the present technology. While in many embodiments the systems, methods, and devices of the present disclosure will automatically predict or identify a desirable post-exercise session response profile, in some such embodiments the desired post-exercise session response profile predicted is provided in a prompt to a user allowing the user to optionally adjust the prediction to the user's actual desired post-exercise session response profile. It is also recognized that in typical embodiments, the desired post-exercise session response profile identified at operation 1520 is provided and defined entirely by direct input from a user. For instance, the user may enter their desired post-exercise response profile (e.g. 65) into a GUI via a touchscreen display of a computing device (e.g. computing device 1200).

Once the desired post-exercise session response profile is identified at operation 1520—whether by automatic prediction, direct input from the user, or the like—method 1500 computes, at operation 1530, an exertion recommendation for the anticipated/impending exercise session. As explained, the exertion recommendation provides a basis from which a user may intelligently gauge/plan their exercise intensity objectives during the exercise session to best achieve the desired post-exercise session response profile. Details for this determination are further described in connection with FIG. 15B below.

As shown in FIG. 15B, at suboperation 1532 method 1500 creates an exertion model by, in some embodiments, associating response profile and exertion measures from prior exercise sessions in one or more expressions. As noted above, because response profile information (see, e.g., FIGS. 14A-14C) and exertion information (see, e.g., FIGS. 13A-13F) may be computed/determined in parallel, the systems, methods, and devices of the present disclosure may identify, store, update, and/or utilize the same to create an intelligent and scientific relationship between them. This relationship may be represented in one or more exertion models (e.g. algebraic expressions, a data structures, matrices, etc.) that associate a user's exertion during a given exercise session with the change in the user's response profile before and after the given exercise session. It should be noted that operation 1532 depicted in FIG. 15B is not intended to required that a new exertion model is produced each time an exertion recommendation is provided in the systems, methods, and devices of the present technology. While this may occur in some embodiment, it need not. For example, a single exertion model may be created and utilized for all exercise sessions, the exertion model may be updated/recreated periodically (e.g. weekly), and the like.

In some embodiments, an exertion model may be configured using predefined parameters and conditions. For example, a user's response profile (i.e. performance capacity) may be indicated on a scale from 0-100, where 0 represents an entirely exhausted condition and 100 represents an entirely rested and able condition. Additionally, the user's exertion load during a particular exercise session may be measured as the sum (or weighted sum) of all exertion values computed at each interval (e.g. second) during that exercise session, where individual exertion values range from 0-10 for any given moment. The user may have used the systems, methods, and devices of the present disclosure in seven prior exercise sessions where the following data (shown in Table 3.0) was computed/processed/determined for each.

TABLE 3.0

| Exercise Session (ES) | ES $\Delta$Time ($\Delta$T) | Pre-ES Response Profile ($RP_{pre}$) | Post-ES Response Profile ($RP_{post}$) | $RP_{post}$ − $RP_{pre}$ ($\Delta$RP) | Exertion Load (EL) | Exertion Index (EI) |
|---|---|---|---|---|---|---|
| 1 | 30 min | 95 | 85 | −10 | 1052 | 7.5 |
| 2 | 60 min | 95 | 60 | −35 | 2250 | 10 |
| 3 | 45 min | 80 | 60 | 20 | 1765 | 9.3 |
| 4 | 35 min | 90 | 77 | 13 | 1268 | 8.2 |
| 5 | 20 min | 50 | 30 | 20 | 640 | 4.3 |
| 6 | 45 min | 63 | 30 | 33 | 1503 | 9.0 |
| 7 | 60 min | 75 | 38 | 37 | 2164 | 9.5 |

Thus, using the data from previous exercise sessions, such as the example data in Table 3.0, operation 1532 of method 1500 may create an exertion model intelligently associating this data. In particular, the actual data from previous exercise sessions may be used to extrapolate an estimate and/or derive an expression (i.e. an exertion model) that provides an estimate of exertion that is typical when other conditions are present, e.g. for a particular change in the user's response profile from before and after an exercise session. For example, the exertion model may be (1) a function of multiple variables (e.g. a multi-dimensional expression that may be represented as a surface in three dimensional space), (2) a multi-dimensional matrix (e.g. 2D, 3D, 4D, etc.), or (3) other data structures relating exertion measures to response profiles as indicated above, or the like. For example, an exertion model may be represented by a best fit expression that maps a change in response profile in a given time interval to a particular exertion load experienced during that time interval, given as some form or variant of the equation (15) below.

$$EL(\Delta T, \Delta RP) = a(\Delta T) + b(\Delta RP) \qquad (15)$$

The exertion model may then be used to determine and provide an exertion recommendation for an anticipated exercise session that is tailored to the particular user based on performance during prior exercise sessions. Equation (15) represents an exemplary form exertion model/expression that may be used, in some embodiments, to estimate and recommend an exertion load (EL) for the user to achieve during an anticipated/imminent exercise session. As shown in equation (15), an exemplary exertion model may compute an exertion load as a function of the length of time ($\Delta$T) the session is intended to last, and the target change in performance capacity given by the desired change in response profile ($\Delta$RP). The exertion recommendation may be provided such that, if the appropriate level of exertion is achieved, the user might attain their desired post-exercise session response profile.

It is noted that the expression representing the exertion model may be derived (using methods commonly known in the art) to provide best fit regression line(s), best fit surface/multivariable expression, or other expression representing a best fit of the data. Further, it will be recognized that the data used to derive the exertion model may include one or more of (1) data collected/computed from the particular user during past exercise sessions (as explained earlier in connection with system 1200, method 1300, and method 1400), (2) data preloaded in the system (e.g. storage 1226 of computing device 1208) representing averages or estimates from other users, (3) data inputted directly by a user via a user interface of a computing device, (4) a weighted combination of (1) and/or (2) and/or (3), or the like.

Of course, it is further noted that equation (15) and the form thereof is not limiting, and merely illustrates one example exertion model that may be used in accordance with the technology disclosed herein. For example, instead of representing a relationship between exertion load and response profile changes, the exertion model may represent a relationship between exertion index and response profile changes, or a combination of both. In other embodiments, the exertion model is represented by more than one expression defining the relationship. And indeed, in some embodiments multiple exertion models may be created at operation 1532 and employed at operation 1534. One of ordinary skill in the art will appreciate that many expressions/models/formula/data structures may be derived/used—using any derivation methods known in the art—establishing a relationship between exertion measures (e.g. any and all exertion measures described in connection with FIGS. 13A-13F), response profiles (e.g., any and all response profile computations described in connection with FIGS. 14A-14C), and other factors (e.g. time intervals, altitude, etc.).

At operation 1534, method 1500 determines an exertion (i.e. exertion load and/or exertion index) for an upcoming exercise session using the exertion model (or an output therefrom) and/or other data; the exertion corresponds to the exertion load and/or exertion index that, if achieved, will allow the a to attain the performance capacity changes (e.g. the changes in the user's response profile) they desire post-exercise session. The user may provide certain information as an input (either directly, or via one or more of biosensor 1210 or motion sensor 1212), and the exertion model may operate on this information to provide an output/determination as noted above. For instance, before an exercise session a user may be provided with their current response profile (i.e. as an indication of current performance capacity), and then input their preferred or desired post-exercise session response profile. In some embodiments, the user may further input an estimated amount of time they expect the exercise session to take (thereby adding more precision to the exertion determined via the exertion model).

For example, the system 1200 may indicate to the user that their response profile (i.e. performance capacity) is 95% and then prompt the user (via GUI of display 1230) to input their desired post-exercise session response profile. The user may then consider their schedule for the day, decide that don't have much else going on that day, for example, and that they can afford to expend a lot of energy in their upcoming exercise session. The user may further input that they want their post-exercise response profile to be 50%, and that they'd like to exercise for 60 minutes. In some such embodiments, with this information as an input, method 1500 at operation 1534 may determine an exertion load and/or exertion index that would correspond to such a change in the user's response profile.

At operation 1536, method 1500 provides a recommended exertion load and/or exertion index for an anticipated exercise session based on the exertion load and/or exertion index determined at operation 1534. In some embodiments, the recommended exertion load may be the same as the exertion load determined at operation 1534. Similarly, in some such embodiments, the recommended exertion index may be the same as the exertion index determined at operation 1534. In other embodiments, the recommended exertion load is a function of (e.g. multiple, percentage) of the exertion load determined at operation 1534, and/or the recommended exertion index is a function of (e.g. multiple, percentage) the exertion index determined at operation 1534. At operation 1536, method 1500 provides and/or stores the exertion recommendation for the upcoming exercise session to one or more of the system, a user, a wearable device, a computing device, and/or a server.

To extend the previous example, computing device 1208 may display to the user a recommended exertion load of 2700, and/or display recommended exertion index of 10 for the upcoming exercise session. Based on this information, a user may then make an informed and intelligent assessment of how they approach and perform the various exercises that comprise their exercise session. Indeed, it may even enable the user to more intelligently decide upon the exercise activity they chooses for the given exercise session (e.g. running, swimming, biking, etc.). Accordingly, the systems, methods, and devices of the present disclosure can enable a user to achieve their exercise goals and lifestyle objectives with more precision, accuracy, and effectiveness.

It should further be noted that, in some embodiments, once the user has completed a given exercise session (or at any time throughout the exercise session), the systems and methods of the present disclosure may further provide an updated/current response profile indication so that the user can obtain a further understanding of their performance capacity going forward. This may enable a user to assess the actual result of their exercise session, in terms of response profile, and reassess the way they approach the remainder of their day and/or when the will retire for the evening, etc.

Additionally, it should further be noted that in embodiments that employ previously collected user exercise session data in creating an exertion model, the systems and methods of the present technology may further utilize any new data collected from each additional exercise session to make an update to (i.e. modify) the existing exertion model to hone the fit of the expression/model to more accurately reflect the user's individual fitness profile. In this manner, in various embodiments, the exertion model may learn the user's typical responses to various exercise sessions (as a function of exercise intensity, exertion load, exertion index, HRV, fatigue, HR, etc.) and evolve/change as the user's fitness levels and performance capacity evolves/changes (e.g. as a user becomes more fit, the recommended exertion load may be greater for the same desired post-exercise session response profile entered by the user).

Figure 16:
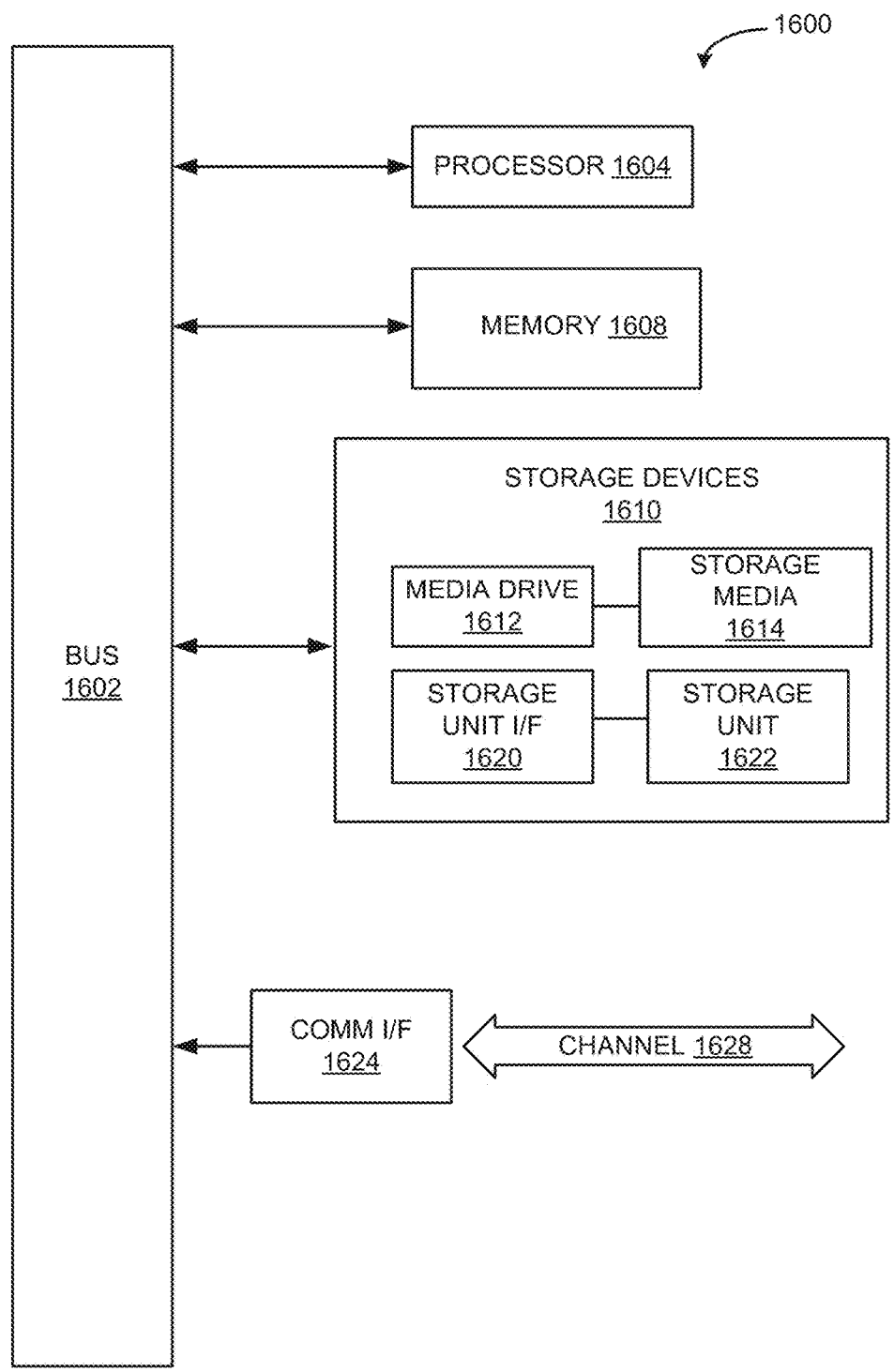
FIG. 16 illustrates an example computing module that may be used to implement features of various embodiments of the present disclosure.

FIG. 16 illustrates example computing module 1600, which may in some instances include a processor/controller resident on a computer system (e.g., computing device 120 or wearable device 1202). Computing module 1600 may be used to implement various features and/or functionality of embodiments of the systems and methods disclosed herein. With regard to the above-described embodiments of computing module 1600, computing device 120, and wearable device 1202, one of skill in the art will appreciate additional variations and details regarding the functionality of the embodiments, as set forth herein in the context of systems and method described with reference to FIGS. 1 through 16. In this connection, it will also be appreciated by one of skill in the art that features and aspects of the various embodiments (e.g., systems) described herein may be implemented with respected to other embodiments (e.g., methods) described herein without departing from the scope and spirit of this disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In implementation, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 16. Various embodiments are described in terms of example computing module 1600. After reading this description, it will become apparent to a person skilled in the relevant art how to implement the application using other computing modules or architectures.

Referring now to FIG. 16, computing module 1600 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); or the like, depending on the application and/or environment for which computing module 1600 is specifically purposed.

Computing module 1600 may include, for example, one or more processors, controllers, control modules, or other processing devices, such as a processor 1604. Processor 1604 may be implemented using a special-purpose processing engine such as, for example, a microprocessor, controller, or other control logic. In the illustrated example, processor 1604 is connected to bus 1602, although any communication medium may be used to facilitate interaction with other components of computing module 1600 or to communicate externally.

Computing module 1600 may also include one or more memory modules, simply referred to herein as main memory 1608. For example, random access memory (RAM) or other dynamic memory may be used for storing information and instructions to be executed by processor 1604. Main memory 1608 may also be used for storing temporary variables or other intermediate information during execution of instructions to be executed by processor 1604. Computing module 1600 may likewise include a read only memory (ROM) or other static storage device coupled to bus 1602 for storing static information and instructions for processor 1604.

Computing module 1600 may also include one or more various forms of information storage devices 1610, which may include, for example, media drive 1612 and storage unit interface 1620. Media drive 1612 may include a drive or other mechanism to support fixed or removable storage media 1614. For example, a hard disk drive, a floppy disk drive, a magnetic tape drive, an optical disk drive, a CD or DVD drive (R or RW), or other removable or fixed media drive may be provided. Accordingly, removable storage media 1614 may include, for example, a hard disk, a floppy disk, magnetic tape, cartridge, optical disk, a CD or DVD, or other fixed or removable medium that is read by, written to or accessed by media drive 1612. As these examples illustrate, removable storage media 1614 may include a computer usable storage medium having stored therein computer software or data.

In alternative embodiments, information storage devices 1610 may include other similar instrumentalities for allowing computer programs or other instructions or data to be loaded into computing module 1600. Such instrumentalities may include, for example, fixed or removable storage unit 1622 and storage unit interface 1620. Examples of such removable storage units 1622 and storage unit interfaces 1620 may include a program cartridge and cartridge interface, a removable memory (for example, a flash memory or other removable memory module) and memory slot, a PCMCIA slot and card, and other fixed or removable storage units 1622 and storage unit interfaces 1620 that allow software and data to be transferred from removable storage unit 1622 to computing module 1600.

Computing module 1600 may also include a communications interface 1624. Communications interface 1624 may be used to allow software and data to be transferred between computing module 1600 and external devices. Examples of communications interface 1624 include a modem or soft-modem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1624 may typically be carried on signals, which may be electronic, electromagnetic (which includes optical) or other signals capable of being exchanged by a given communications interface 1624. These signals may be provided to communications interface 1624 via channel 1628. Channel 1628 may carry signals and may be implemented using a wired or wireless communication medium. Some non-limiting examples of channel 1628 include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, main memory 1608, storage unit interface 1620, removable storage media 1614, and channel 1628. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing module 1600 or a processor to perform features or functions of the present application as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard,"

"known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for providing an exertion recommendation, the system comprising:
   a wearable device, comprising:
      a heart rate sensor that is configured to monitor a heart rate of a user wearing the wearable device;
      a motion sensor that is configured to monitor activity of the user wearing the wearable device;
   a processor operatively coupled to the heart rate sensor and the motion sensor, the processor configured to process electronic signals generated by the heart rate sensor and the motion sensor and generate one or more of heart rate data and activity data therefrom; and
   a non-transitory computer-readable medium operatively coupled to the processor and storing instructions that, when executed, cause the processor to:
      generate an exertion load recommendation for an exercise session based on a targeted performance capacity, wherein the exertion load recommendation provides the user with a plan to attain the targeted performance capacity that is based on the user's capacity to perform exercise after completing the exercise session, wherein
         the exertion load recommendation is generated from an exertion model that associates the user's exertion load to the user's performance capacity based on heart rate data and activity data collected from the wearable device during a plurality of previous exercise sessions when the wearable device was worn by the user, and
         the exertion model is based on data from the heart rate monitored by the heart rate sensor and the activity monitored by the motion sensor;
      determine the exertion load during the exercise session based on accumulating exercise intensity of the user during the exercise session, wherein the exercise intensity of the user is based on the heart rate data; and
      provide the determined exertion load to the user during the exercise session.

2. The system of claim 1, wherein the wearable device comprises one or more of an earphone and a wristband.

3. The system of claim 1, wherein the heart rate sensor comprises one or more of a finger heart rate sensor, a wrist heart rate sensor, and an optical heartrate sensor.

4. The system of claim 1, wherein the heart rate data includes one or more of a heart rate and a heart rate variability.

5. The system of claim 1, wherein the exertion recommendation is further based on the amount of time the exercise session is anticipated to take.

6. The system of claim 1, further comprising:
   a first wireless transceiver embedded in the wearable device;
   a computing device; and
   a second wireless transceiver embedded in the computing device operatively coupled to the wearable device, wherein the first and second wireless transceivers are configured to receive and send one or more of the heart rate data and the activity data.

7. The system of claim 1, wherein the exertion model associates the user's exertion load to changes in the user's performance capacity over a duration of each exercise session.

8. A system for providing an exertion recommendation, the system comprising:
   an electronic clock configured to monitor time;
   a wearable device, comprising:
      a heart rate sensor that is configured to monitor a heart rate of a user wearing the wearable device;
      a motion sensor that is configured to monitor activity of the user wearing the wearable device;
   a processor operatively coupled to the heart rate sensor and the motion sensor, the processor configured to process electronic signals generated by the heart rate sensor and the motion sensor and generate one or more of heart rate data and activity data therefrom; and
   a non-transitory computer-readable medium operatively coupled to the processor and storing instructions that, when executed, cause the processor to:
      generate an exertion load recommendation for a future exercise session based on a targeted performance capacity that represents the user's capacity to perform exercise after completing the future exercise session, wherein the exertion load recommendation provides the user with a plan to attain the targeted performance capacity,
         wherein the exertion load recommendation for the future exercise session is generated from an exertion model that associates the user's exertion load to the user's performance capacity based on heart rate data and activity data collected from the wearable device during a plurality of previous exercise sessions when the wearable device was worn by the user, and
         the exertion model is based on data from the heart rate monitored by the heart rate sensor and the activity monitored by the motion sensor;
      determine the exertion load during the future exercise session based on accumulating exercise intensity of the user during the future exercise session, wherein the exercise intensity of the user is based on the heart rate data; and provide the determined exertion load to the user during the future exercise session.

9. The system of claim 8, wherein the wearable device comprises one or more of an earphone and a wristband.

10. The system of claim 8, wherein the heart rate sensor comprises one or more of a finger heart rate sensor, a wrist heart rate sensor, and an optical heartrate sensor.

11. The system of claim 8, wherein the heart rate data includes one or more of a heart rate and a heart rate variability.

12. The system of claim 8, wherein: the exertion model is further based on the amount of time taken to complete a previous exercise session as monitored by the electronic clock; and the exertion recommendation is further based on the amount of time the exercise session is anticipated to take.

13. The system of claim 8, wherein the exertion model associates the user's exertion load to changes in the user's performance capacity over a duration of each exercise session.

14. The system of claim 8, further comprising:
a first wireless transceiver embedded in the wearable device;
a computing device; and
a second wireless transceiver embedded in the computing device operatively coupled to the wearable device, wherein, the first and second wireless transceivers are configured to receive and send one or more of the heart rate data and the activity data.

15. A computer-implemented method for determining an exertion recommendation for an anticipated exercise session, the method comprising:
measuring a heart rate of a user during a plurality of exercise sessions using a heart rate sensor embedded in a wearable device;
measuring activity of a user during the plurality of exercise sessions using a motion sensor embedded in the wearable device;
generating heart rate data from the measured heart rate;
generating activity data from the measured activity;
generating a plurality of exercise intensity values during each exercise session based on the heart rate measured by the heart rate sensor and the activity measured by the motion sensor during that exercise session;
generating an exertion load value for each exercise session based on accumulating the plurality of exercise intensity values generated during that exercise session;
determining a change in performance capacity of the user that occurs as a result of the user performing each exercise session, wherein the performance capacity is the user's capacity to perform exercise;
generating an exertion model that associates the user's exertion load to the user's change in performance capacity based on the heart rate data and the activity data collected from the wearable device during the plurality of exercise sessions when the wearable device was worn by the user; and
generating an exertion load recommendation for a future exercise session based on a targeted performance capacity that represents the user's capacity to perform exercise after completing the future exercise session, wherein the exertion load recommendation provides the user with a plan to attain the targeted performance capacity,
wherein the exertion load recommendation for the future exercise session is generated from the exertion model.

16. The computer-implemented method of claim 15, wherein generating the exertion load value for a given exercise session comprises:
weighting each of a plurality of exercise intensity values based on each exercise intensity value's proximity in time to the most recent exercise intensity value generated during that exercise session;
aggregating the weighted plurality of exercise intensity values over a measuring period; and
generating the exertion load value for that exercise session based on the aggregation of the weighted plurality of exercise intensity values for the measuring period.

17. The computer-implemented method of claim 15, wherein generating the exertion model comprises:
calculating a current HRV value from the heart rate data;
calculating, based on a set of HRV values previously calculated using the heart rate data, an average HRV value and an HRV variation;
calculating an HRV score based on a difference between the average HRV value and the current HRV value, the difference being scaled by the HRV variation; and
creating the exertion model based on one or more a heart rate variability (HRV) score based on the heart rate data, a fatigue score based on the activity data, a predicted HRV score based on the heart rate data and the activity data, and a predicted fatigue score based on one or more of the heart rate data and the activity data.

18. The computer-implemented method of claim 15, wherein the wearable device comprises one or more of an earphone and a wristband.

19. The computer-implemented method of claim 15, wherein the heart rate sensor comprises one or more of a finger heart rate sensor, a wrist heart rate sensor, and an optical heartrate sensor.

20. The computer-implemented method of claim 15, wherein the heart rate data includes one or more of a heart rate and a heart rate variability.

21. The computer-implemented method of claim 15, wherein:
the exertion model is further based on an amount of time taken to complete the plurality of the exercise sessions; and
the exertion load recommendation is further based on an amount of time the future exercise session is anticipated to take.

22. The computer-implemented method of claim 15, further comprising: receiving one or more of heart rate data and activity data at a computing device having a wireless receiver.

23. The computer-implemented method of claim 15, further comprising
determining the exertion load during the future exercise session based on accumulating exercise intensity of the user during the future exercise session, wherein the exercise intensity of the user is based on the heart rate data; and
providing the determined exertion load to the user during the future exercise session.

* * * * *